(12) United States Patent
Falco et al.

(10) Patent No.: US 7,741,537 B2
(45) Date of Patent: Jun. 22, 2010

(54) S-ADENOSYL-L-METHIONINE SYNTHETASE PROMOTER AND ITS USE IN EXPRESSION OF TRANSGENIC GENES IN PLANTS

(75) Inventors: Saverio Carl Falco, Wilmington, DE (US); Zhongsen Li, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 610 days.

(21) Appl. No.: 11/746,708

(22) Filed: May 10, 2007

(65) Prior Publication Data

US 2008/0229457 A1 Sep. 18, 2008

Related U.S. Application Data

(62) Division of application No. 10/431,252, filed on May 7, 2003, now Pat. No. 7,217,858.

(51) Int. Cl.
*C12N 15/82* (2006.01)
*A01H 5/00* (2006.01)
*A01H 5/10* (2006.01)

(52) U.S. Cl. .................. 800/298; 435/419; 800/312; 800/306; 800/314; 800/317.3; 800/317.4; 800/317.2

(58) Field of Classification Search .................. None
See application file for complete search history.

(56) References Cited

FOREIGN PATENT DOCUMENTS

| EP | 0559603 A2 | 9/1993 |
|---|---|---|
| WO | 9305160 A1 | 3/1993 |
| WO | 9535386 A1 | 12/1995 |
| WO | 9705260 A2 | 2/1997 |
| WO | 9855601 A2 | 12/1998 |
| WO | 9931258 A1 | 6/1999 |

OTHER PUBLICATIONS

Vander Mijnsbrugge K. et al. Tissue-specific expression conferred by the S-adenosyl-L-methionine synthetase promoter of *Arabidopsis thaliana* in transgenic poplar. Plant Cell Physiol. 1996, 37(8): 1108-1115.*
C. K. Chong et al., Amino Acid Residues Conferring Herbicide Tolerance in Tobacco Acetolactate Synthase. Biochem. Biophys. Res. Commun., vol. 279(2):462-467, 2000.
Y. Kim et al., A 20 Nucleotide Upstream Element is Essential for the Nopaline Synthase (NOS) Promoter Activity. Plant Mol. Biol., vol. 24(1):105-117, 1994.
Johan Peleman et al., Strong Cellular Preference in the Expression of a Housekeeping Gene of *Arabidopsis thaliana* Encoding S-Adenosylmethionine Synthetase, The Plant Cell, vol. 1:81-93, 1989.
Kristine Vander Mijnsbrugge et al., Tissue-Specific Expression Conferred by the S-Adenosyl-L-Methionine Synthetase Promoter of *Arabidopsis thaliana* in Transgenic Poplar, Plant Cell Phyisol., vol. 37(8):1108-1115, 1996.
Lourdes Gomez-Gomez et al., Differential Expression of the S-Adenosyl-L-Methionine Synthase Genes During Pea Development, Plant Physiol., vol. 117:397-405, 1998.
Dae Gun Kim et al., Purification and Characterization of S-Adenosylmethionine Synthetase From Soybean (Glycine Max) Axes, Database Biosis, Journal of Biochemistry and Molecular Biology, vol. 28(2), 1995.
Lourdes Gomez-Gomez et al., Hormonal Regulation of S-Adenosylmethionine Synthase Transcripts in Pea Ovaries, Plant Molecular Biology, vol. 30:821-832, 1996.
J. Feng et al., *Arabidopsis thaliana* Genomic Clone F6L 16 Genomic Survey Sequence, EMBL Accession No. B09084, University of Pennsylvania, May 15, 1997.
Puchta Holger, Gene Replacement by Homologous Recombination in Plants, Plant Mol. Biol., vol. 48:173-182, 2002.
Philip N. Benfey et al., The Cauliflower Mosaic Virus 35S Promoter: Combinatorial Regulation of Transcription in Plants, Science, vol. 250:959-966, 1990.
Alexander R. Van Der Krol et al., Inhibition of Flower Pigmentation by Antisense CHS Genes: Promoter and Minimal Sequence Requirements for the Antisense Effect, Plant Mol. Biol., vol. 14:457-466, 1990.
Gudrun Schroder et al., Three Differentially Expressed S-Adenosylmethionine Synthetases From *Catharanthus roseus*:Molecular and Functional Characterization, Plant Molecular Biology, vol. 33:211-222, 1997.

* cited by examiner

*Primary Examiner*—Cynthia Collins

(57) ABSTRACT

A constitutive plant S-adenosyl-L-methionine synthetase (SAMS) promoter and subfragments thereof and their use in promoting the expression of one or more heterologous nucleic acid fragments in plants are described.

8 Claims, 16 Drawing Sheets

```
TTAGTTTTATTAGAAATATTAATTAGAAAATTTGAATCCCGATTTCTCCTCCTTTTCTTCGCTATTCATCATTTCTA
ACCAAACCAATCTTATATGTTCTTCAAATTTCACAAAACCATAATATAATTATAATTAAACTGAAAACAATTGTATCAA
ATCGATAGACATGTTATTCACAAAACCATAATGGCTAAAATGATGGAACGATATCGTTTATTATGA
TTTCAGGGCGCAAAATGCGAGTACTTAATAAATTTTACATTTAAATTAGAATTTTTTTATCAATAAATATTAATTTA
TCATATACATGCTTAGTAATAAAATGCGATAATTAATTGATAAATCTGCAAAAGATTTTACAAATATCTTTCAGAAAAA
ATTAATAACAAATTTTGTCGTTTCATGGTCGTTGTTGGGTCTCGAGGAGGATTTGGCACTATAGAATCTCCTACGGACCATTCT
TTGCACTTCAACTAAACGATGGTCAGAATTGGTGGGAATTTTATATTCAAGACATATCCCTTCAAAACTTCCTACTTACT
TCGTGCGTTCGGTAATCGGTAACATTAGACTTTCAAAATCATTTTTAACCCCTAAACAGTAAATTTGAAGGACAAAAATA
ATATTTCAAATTGATAGAATATTTATTTATTTATTTGTAATTGACGAACAAAACCAGATTATCCTGAATTTAGGAACC
ACAGATGTAACTAAACCAATATATTATTATTTATTTCTAAACAAAATTTCATGGCAGCATGCCTCAGCCTCAAACTCAATCCAAACATAA
TTATAAAATATCTACACATTGACCATTGAAAAGTTCGTTCTCCATGGTCTAAATAATTAATCATTATTTTAAGATATTAATTAAGAAAT
CATGGATATCTCCTTACCAATCATACTAATTTATAAAAATGTATAAAATTATTCATGATTTTCATACATTGATTTTGATAATAATATTT
TAAAAGATTTTTTAAAAATTCTTAAAAAATGTTGCAAGACACTTATTAGACACTTAATTAAAAGCATTCATCATTTAAT
ACATTAAAAAATATTTAATACTAACAGTAGAATCTTCTTGTGTGGAGTGGCAACCTGGCATTGGAAACGAGA
GAAAGAGAGTCAGAACCAGAAGACAAATAAAAACATGCAACAAACAAATCAAAATCACTCTGACTTCCCCAATCACCCCGGGGTTGGC
TCAATTGGTTGCTACATTCAATTTCAACTCCAATCCAATCTCCTTACTTAGGGGCTTTCTCCGTCATTCACCCCTGCCACCCGGTT
CAAACGGTTGAATCTAACCACAATGCTCCCCTCCTACCTCCTCAAGTTATGCGTATCGTTTCTTCTTCCTCAACTGGGTCCATCTAGGATCCATGTGAAACTCTAC
TCCCTATAAATTGGAACTCAATCATTTGGGTATCGTTTCTTCTTCCTCAACTGGGTCCATCTAGGATCCATGTGAAACTCTAC
TTTCGGATCTTGCACTTCGGTTTGCTTTGCCTTTTTGTCCTTGCGTTTTTCCTCAGATCTAGTAGTAGTCGAAATCATTTCATAATTGCCTTTTCTTTT
TCTTTCTTTAATATCTGCGAATACATCATTTGTTTTTATTTGTAATTGTACTTGTTTGTCTTTTCAAAAATAAACTTTGGGCCTTGGTTTTGTTTTCTCATACATTCCT
AGCTTATCAGAATTTAGCGAATTTATTCGAGTATAGTTTAAAAAATCATTTTGTTTGTCTTTTCAAAAATAAACTTTGGGCCTTGGTGTTTTGTTTCTCATACATTCCT
TTACAGAATTTAGCGAATTTATTCGAGTATAGGTCACAATAGAATTCAAACTTTGAGCAGGGGGAATTAACCCTTCCTTCAAATC
TAGGCTTCAATTTGTTGTATATGTTTAAAAAATGAAACTTTTGCTTTAAATTCTATTATAACTTTTTTATGGCAAAAATTTT
CAGTCTTGTTGTTGTATATGTTTAAAAATGAAACTTTTGCTTTAAATTCTATTATAACTTTTTTATGGCAAAAATTTT
GCATGTGTCTTTGCTCTCCTGTGTTGTAAATTTACTGTTTAGGTACTAACTCTAGGCTTGTTGTGCAGTTTTGAAGTATAA
```

FIG. 2A

```
AGCCAAGCCCCACTCAACCACCACCACACTCTCTCTGCTCTTCTTCTACCTTTCAAGTTTTAAA
AGATGGCAGAGACATTCCTATTCACCTCGGAGTCAGTGAACGAGGACACCCTGATAAGCTCTGCGACCAAATCTCCGAT
: : : : : : : : : : : : : : : : : : : : : : : : : : : : : : : : : : : : : : : : : : : : : : : : : : : : : : : : : : : : : : : : : : : : : : : : : :
AGATGGCAGAGACATTCCTATTTACCTCAGAGTCAGTGAACGAGGACACCCTGACAAGCTCTGCGACCAAATCTCCGAT

GTATTAGCTGTCCTCGACGCTTGCCTCGAACAGGACCCAGACAGCAAGGTTGCCTGCGAAACATGCACCAAGACCAACTTGGTCAT
: : : : : : : : : : : : : : : : : : : : : : : : : : : : : : : : : : : : : : : : : : : : : : : : : : : : : : : : : : : : : : : : : : : : : : : : : : : : : : : : : :
GCTCTCCTCGACGCTTGCCTTGAACAGGACCCAGACACAGCACCAAGACCCAGAGACCCAGAGACAGCAAGGTTGCCTGCGAAACATGCACCAAGACCAACTTGGTCAT

GGTCTTCGGAGAGATC
: : : : : : : : : : : : : : : :
GGTCTTCGGAGAGATC
```

FIG. 2B

```
                        *  ***
SEQ ID NO:27    1   MAAAAAAPSPS----FSKTLSSSSKSSTLLPRSTFPFPHHPHKTTPPLH--LTPTHIH
SEQ ID NO:28    1   MAAAATS------SSPISLTAKPS---SKSPLPISREFSLPFSLTPQKPSSRLHR------PL
SEQ ID NO:29    1   MAAATTTTTSSSISFSTKPSPSSSKSPLPISRFSLPFSLNPNKSSSSRRRGIKSSSPS
SEQ ID NO:30    1   MAATASRTTRFSS--------SSSHPFTFPKRITRSTLPLSHQTLT--------KPNHAL
                    1                                                              60

*    *          *  **** **  *  *      ***   ***    **
SEQ ID NO:27   55   SQRRRFTISNVISTTQKVSETQKAETFVSRFFAPDEPRKGSDVLVEALEREGVTDVFAYPG
SEQ ID NO:28   47   AISAVLNSPVNVA----PEKTDKIKTFEISRYAPDEPRKGADILVEALERQGVETVFAYPG
SEQ ID NO:29   61   SISAVLNTTTNVTTTPSPTKPETFISRFAPDQPRKGADILVEALERQGVETVFAYPG
SEQ ID NO:30   44   KIKCSISKPP---TAAPFTKEAPTTEPFVSRFASGEPRKGADILVEALERQGVTTVFAYPG
                    61                                                            "A" PG

*  ****  *********  ******  *********  *****   ****
SEQ ID NO:27  115   GASMEIHQALTRSSIIRNVLPRHEQGGVFAAEGYARATGFPGVCIATSGPGATNLVSGLA
SEQ ID NO:28  103   GASMEIHQALTRSSTIRNVLPRHEQGGVFAAEGYAAEGYARSSGKPGICIATSGPGATNLVSGLA
SEQ ID NO:29  121   GASMEIHQALTRSSIRNVLPRHEQGGVFAAEGYARSSGKPGICIATSGPGATNLVSGLA
SEQ ID NO:30  102   GASMEIHQALTRSAAIRNVLPRHEQGGVFAAAEGYARSSGLPGVCIATSGPGATNLVSGLA
                    GA                                                             180

**  *****  ****  **  ***   ****    ****  ****     ****
SEQ ID NO:27  175   DALLDSVPIVAITGQVPRRMIGTDAFQETPIVEVTRSITKHNYLVMDVEDIPRVVREAFF
SEQ ID NO:28  163   DAMLDSVPIVAITGQVPRRMIGTDAFQETPIVEVTRSITKHNYLVMDVDDIPRIVQEAFF
SEQ ID NO:29  181   DALLDSVPLVAITGQVPRRMIGTDAFQETPIVEVTRSITKHNYLVMDVEDIPRITEEAFF
SEQ ID NO:30  162   DALMDSVPVVAITGQVPRRMIGTDAFQETPIVEVSRSITKHNYLILDVDDIPRVVAEAFF
                    GQVP      IGTDAFQE                                            240
                    "B"       "C"
```

FIG. 10A

| | | |
|---|---|---|
| SEQ ID NO:27 | 235 | LARSGRPGPVLIDVPKDIQQQLVIPDWDQPMRLPGYMSRLPKLPNEMLLEQIVRLISESK |
| SEQ ID NO:28 | 223 | LATSGRPGPVLVDVPEKDIQQQLAIPNWDQPMRLPGYMSRLPQPPEVSQLGQIVRLISESK |
| SEQ ID NO:29 | 241 | LATSGRPGPVLIDVPKDIQQQLAIPNWEQAMRLPGYMSRMPKPPEDSHLEQIVRLISESK |
| SEQ ID NO:30 | 222 | VATSGRPGPVLIDIPKDVQQQLAVPNWDEPVNLPGYLARLPRPPAEAQLEHIVRLIMEAQ 300 |
| | | PKD |
| | | "D" |

| | | |
|---|---|---|
| SEQ ID NO:27 | 295 | KPVLYVGGGCSQSSEELRRFVELTGIPVASTLMGLGAFPTGDELSLSMLGMHGTVYANYA |
| SEQ ID NO:28 | 283 | RPVLYVGGGSLNSSEELGRFVELTGIPVASTLMGLGSYPCNDELSLQMLGMHGTVYANYA |
| SEQ ID NO:29 | 301 | KPVLYVGGGCLNSSDELGRFVELTGIPVASTLMGLGSYPCDDELSLHMLGMHGTVYANYA |
| SEQ ID NO:30 | 282 | KPVLYVGGGSLNSSAELRRFVELTGIPVASTLMGLGTFPIGDEYSLQMLGMHGTVYANYA |
| | | 301 MLGMHG 360 |
| | | "G" |

| | | |
|---|---|---|
| SEQ ID NO:27 | 355 | VDSSDLLAFGVRFDDRVTGKLEAFASRAKIVHIDIDSAEIGKNKQPHVSICADIKLALQ |
| SEQ ID NO:28 | 343 | VEHSDLLAFGVRFDDRVTGKLEAFASRAKIVHIDIDSAEIGKNKTPHVSVCGDVKLALQ |
| SEQ ID NO:29 | 361 | VEHSDLLAFGVRFDDRVTGKLEAFASRAKIVHIDIDSAEIGKNKTPHVSVCGDVKLALQ |
| SEQ ID NO:30 | 342 | VDNSDLLAFGVRFDDRVTGKLEAFASRAKIVHIDIDSAEIGKNKQAHVSVCADLKLALK 420 |
| | | 361 RFDDR |
| | | "F" |

| | | |
|---|---|---|
| SEQ ID NO:27 | 415 | GLNSILESKEGKIKLDFSAWRQELTVQKVKYPLNFKTFGDAIPPQYAIQVLDELTNGSAI |
| SEQ ID NO:28 | 403 | GMNKVLENRAEELKLDFGVWRSELSEQKQKFPLSEKTFGEAIPPQYAIQVLDELTQGKAI |
| SEQ ID NO:29 | 421 | GMNKVLENRAEELKLDFGVWRNELNVQKQKFPLSEKTFGEAIPPQYAIKVLDELTDGKAI |
| SEQ ID NO:30 | 402 | GINMILEEKGVEGKFDLGGWREEINVQKHKFPLGYKTFQDAISPQHAIEVLDELTNGDAI 480 |

FIG. 10B

```
SEQ ID NO:27   475                                       ISTGVGQHQMWAAQYYKYRKPRQWLTSGGLGAMGFGLPAAIGAAVGRPDEVVVDIDGDGS
SEQ ID NO:28   463                                       ISTGVGQHQMWAAQFYKYRKPRQWLSSSGLGAMGFGLPAAIGASVANPDAIVVDIDGDGS
SEQ ID NO:29   481                                       ISTGVGQHQMWAAQFYNYKKPRQWLSSGGLGAMGFGLPAAIGASVANPDAIVVDIDGDGS
SEQ ID NO:30   462                                       VSTGVGQHQMWAAQFYKYKRPRQWLTSGGLGAMGFGLPAAIGAAVANPGAVVVDIDGDGS
                                                         481                                                       540

SEQ ID NO:27   535                                       FIMNVQELATIKVENLPVKIMLLNNQHLGMVVQWEDRFYKANRAHTYLGNPSNEAEIFPN
SEQ ID NO:28   523                                       FIMNVQELATIRVENLPVKILLLLNNQHLGMVMQWEDRFYKANRAHTYLGDPARENEIFPN
SEQ ID NO:29   541                                       FIMNVQELATIRVENLPVKVLLLNNQHLGMVMQWEDRFYKANRAHTFLGDPAQEDEIFPN
SEQ ID NO:30   522                                       FIMNVQELATIRVENLPVKILLLNNQHLGMVVQWEDRFYKSNRAHTYLGDPSSESEIFPN
                                                                         GMVVQWEDRF                               600
                                                                            "F"

SEQ ID NO:27   595                                       MLKFAEACGVPAARVTHRDDLRAAIQKMLDTPGPYLLDVIVPHQEHVLPMIPSGGAFKDV
SEQ ID NO:28   583                                       MLQFAGACGIPAARVTKKEELREAIQTMLDTPGPYLLDVICPHQEHVLPMIPSGGTFKDV
SEQ ID NO:29   601                                       MLLFAAACGIPAARVTKKADIREAIQTMLDTPGPYLLDVICPHQEHVLPMIPSGGTFNDV
SEQ ID NO:30   582                                       MLKFADACGIPAARVTKKEELRAAIQRMLDTPGPYLLDVIVPHQEHVLPMIPSNGSFKDV
                                                         601                                                       660

SEQ ID NO:27   655   ITEGDGRSSY   664
SEQ ID NO:28   643   ITEGDGRTKY   652
SEQ ID NO:29   661   ITEGDGRIKY   670
SEQ ID NO:30   642   ITEGDGRTRY   651
                     661       670
```

FIG. 10C pZSL11 pZSL12

Suspension Culture

Leaf+Stem

Root

US 7,741,537 B2

S-ADENOSYL-L-METHIONINE SYNTHETASE PROMOTER AND ITS USE IN EXPRESSION OF TRANSGENIC GENES IN PLANTS

This application is a Divisional of U.S. application Ser. No. 10/431,252, filed May 7, 2003, now U.S. Pat. No. 7,217,858, the entire contents of which are herein incorporated by reference, which claims the benefit of U.S. application Ser. No. 09/464,528, filed Dec. 15, 1999, now abandoned, the entire contents of which are herein incorporated by reference, which in turn claims the benefit of U.S. Provisional Application No. 60/113,045, filed Dec. 21, 1998, now expired, the entire contents of which are herein incorporated by reference.

FIELD OF THE INVENTION

This invention relates to a plant promoter, in particular, to an S-adenosyl-L-methionine synthetase (SAMS) promoter and subfragments thereof and their use in regulating the expression of at least one heterologous nucleic acid fragment in plants.

BACKGROUND OF THE INVENTION

Recent advances in plant genetic engineering have opened new doors to engineer plants having improved characteristics or traits, such as, resistance to plant diseases, insect resistance, herbicidal resistance, enhanced stability or shelf-life of the ultimate consumer product obtained from the plants and improvement of the nutritional quality of the edible portions of the plant. Thus, a desired gene (or genes) from a source different than the plant, but engineered to impart different or improved characteristics or qualities, can be incorporated into the plant's genome. This new gene (or genes) can then be expressed in the plant cell to exhibit the new trait or characteristic.

In order to obtain expression of the newly inserted gene in the plant cell, the proper regulatory signals must be present and be in the proper location with respect to the gene. These regulatory signals include a promoter region, a 5' non-translated leader sequence and a 3' transcription termination/polyadenylation sequence.

A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce messenger RNA (mRNA) which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cells to cause termination of the RNA transcript and the addition of polyadenylate nucleotides to the 3' end of the RNA.

It has been shown that certain promoters are able to direct RNA synthesis at a higher rate than others. These are called "strong promoters". Certain other promoters have been shown to direct RNA production at higher levels only in particular types of cells or tissues and are often referred to as "tissue specific promoters". In this group, many seed storage protein genes' promoters have been well characterized and widely used, such as the phaseolin gene promoter of *Phaseolus vulgaris*, the helianthinin gene of sunflower, the β-conglycinin gene of soybean (Chen et al., (1989) *Dev. Genet.* 10, 112-122), the napin gene promoter of *Brassica napus* (Ellerstrom et al, (1996) *Plant Mol. Biol.* 32, 1019-1027), the oleosin gene promoters of *Brassica* and *Arabidopsis* (Keddie et al, (1994) *Plant Mol. Biol.* 24, 327-340; Li, (1997) Texas A&M Ph.D. dissertation, pp. 107-128; Plant et al, (1994) *Plant Mol. Biol.* 25, 193-205). Another class of tissue specific promoters is described in, U.S. Pat. No. 5,589,583, issued to Klee et al. on Dec. 31, 1996; these plant promoters are capable of conferring high levels of transcription of chimeric genes in meristematic tissues and/or rapidly dividing cells. In contrast to tissue-specific promoters, "inducible promoters" direct RNA production in response to certain environmental factors, such as heat shock, light, hormones, ion concentrations etc. (Espartero et al, (1994) *Plant Mol. Biol.* 25, 217-227; Gomez-Gomez and Carrasco, (1998) *Plant Physiol.* 117, 397-405; Holtorf et al, (1995) *Plant Mol. Biol.* 29, 637-646; MacDowell et al, (1996) *Plant Physiol.* 111, 699-711; Mathur et al, (1992) *Biochem. Biophys. Acta* 1137, 338-348; Mett et al, (1996) *Transgenic Res.* 5, 105-113; Schoffl et al, (1989) *Mol. Gen. Genet.* 217, 246-253; Ulmasov et al, (1995) *Plant Physiol.* 108, 919-927).

Promoters that are capable of directing RNA production in many or all tissues of a plant are called "constitutive promoters". The ideal constitutive promoter should be able to drive gene expression in all cells of the organism throughout its development. Expression of many so-called constitutive genes, such as actin (McDowell et al., (1996) *Plant Physiol.* 111, 699-711; Wang et al., (1992) *Mol. Cell Biol.* 12, 3399-3406), and ubiquitin (Callis et al, (1990) *J. Biol. Chem.* 265, 12486-12493; Rollfinke et al, (1998) *Gene* 211, 267-276) varies depending on the tissue types and developmental stages of the plant. The most widely used constitutive promoter, the cauliflower mosaic virus 35S promoter, also shows variations in activity in different plants and in different tissues of the same plant (Atanassova et al., (1998) *Plant Mol. Biol.* 37, 275-285; Battraw and Hall, (1990) *Plant Mol. Biol.* 15, 527-538; Holtorf et al., (1995) *Plant Mol. Biol.* 29, 637-646; Jefferson et al., (1987) *EMBO J.* 6, 3901-3907; Wilmink et al., (1995) *Plant Mol. Biol.* 28, 949-955). The cauliflower mosaic virus 35S promoter is also described in U.S. Pat. No. 5,106,739. The tissue-specific expression and synergistic interactions of sub-domains of the promoter of cauliflower mosaic virus are discussed in U.S. Pat. No. 5,097,025, which issued to Benfey et al. on Mar. 17, 1992. A *Brassica* promoter (hsp80) that provides for constitutive expression of heterologous genes in a wide range of tissues and organs is discussed in U.S. Pat. No. 5,612,472 which issued to Wilson et al. on Mar. 18, 1997.

Some constitutive promoters have been used to drive expression of selectable marker genes to facilitate isolation of transformed plant cells. U.S. Pat. No. 6,174,724 B1, issued to Rogers et al. on Jan. 16, 2001, describes chimeric genes which can be used to create antibiotic or herbicide-resistant plants.

Since the patterns of expression of a chimeric gene (or genes) introduced into a plant are controlled using promoters, there is an ongoing interest in the isolation and identification of novel promoters which are capable of controlling expression of a chimeric gene (or genes).

SUMMARY OF THE INVENTION

This invention concerns an isolated nucleic acid fragment comprising a promoter wherein said promoter consists essentially of the nucleotide sequence set forth in SEQ ID NOs:6, 14, 15, or 16 or said promoter consists essentially of a fragment or subfragment that is substantially similar and functionally equivalent to the nucleotide sequence set forth in SEQ ID NOs:6, 14, 15, or 16.

In a second embodiment, this invention concerns a chimeric gene comprising at least one heterologous nucleic acid fragment operably linked to the promoter of the invention.

In a third embodiment, this invention concerns plants containing this chimeric gene and seeds obtained from such plants.

In a fourth embodiment, this invention concerns a method of increasing or decreasing the expression of at least one heterologous nucleic acid fragment in a plant cell which comprises:
 (a) transforming a plant cell with the chimeric gene described above;
 (b) growing fertile plants from the transformed plant cell of step (a);
 (c) selecting plants containing the transformed plant cell wherein the expression of the heterologous nucleic acid fragment is increased or decreased.

In a fifth embodiment, this invention concerns an isolated nucleic acid fragment comprising a constitutive plant SAMS promoter.

In a sixth embodiment, this invention concerns a recombinant DNA construct comprising a first isolated nucleic acid fragment encoding a polypeptide with acetolactate synthase activity, wherein said polypeptide has one or both of the following mutations, an amino acid other than proline in a conserved amino acid region G-Q-V—P (SEQ ID NO:31) and an amino acid other than tryptophan in a conserved amino acid region G-M-V—V/M-Q-W-E-D-R—F (SEQ ID NO:32), and said polypeptide is resistant to at least one inhibitor of acetolactate synthase, operably linked to a second isolated nucleic acid fragment, having constitutive promoter activity in a plant, selected from the group consisting of:
 a) an isolated nucleic acid fragment comprising the nucleic acid sequence of SEQ ID NO:6;
 b) an isolated nucleic acid fragment comprising the nucleic acid sequence of SEQ ID NO:14;
 c) an isolated nucleic acid fragment comprising nucleotides 4-644 of SEQ ID NO:6;
 d) an isolated nucleic acid fragment comprising nucleotides 1-1496 of SEQ ID NO:14;
 e) an isolated nucleic acid fragment comprising a subfragment of SEQ ID NO:6, wherein the subfragment has constitutive promoter activity in a plant;
 f) an isolated nucleic acid fragment comprising a subfragment of SEQ ID NO:14, wherein the subfragment has constitutive promoter activity in a plant; and
 g) an isolated nucleic acid fragment, having constitutive promoter activity in a plant, which can hybridize under stringent conditions with any of the isolated nucleic acid fragments set forth in (a) through (f).

In a seventh embodiment, this invention concerns a method for selection of a transformed plant cell having resistance to at least one inhibitor of acetolactate synthase which comprises:
 (a) transforming a plant cell with the recombinant DNA construct of the sixth embodiment;
 (b) growing the transformed plant cell of step (a) in the presence of an effective amount of at least one inhibitor of acetolactate synthase; and
 (c) selecting a transformed plant cell wherein said transformed plant cell is resistant to at least one inhibitor of acetolactate synthase.

In an eighth embodiment, this invention concerns a method for producing a plant having resistance to at least one inhibitor of acetolactate synthase which comprises:
 (a) transforming a plant cell with the recombinant DNA construct of the sixth embodiment;
 (b) growing at least one fertile transformed plant from the transformed plant cell of step (a); and
 (c) selecting a transformed plant wherein said transformed plant is resistant to at least one inhibitor of acetolactate synthase.

BRIEF DESCRIPTION OF THE DRAWINGS AND SEQUENCES

The invention can be more fully understood from the following detailed description, the drawings and the Sequence Descriptions that form a part of this application. The Sequence Descriptions contain the three letter codes for amino acids as defined in 37 C.F.R. §§1.821-1.825, which are incorporated herein by reference.

SEQ ID NO:1 is the nucleotide sequence comprising the entire cDNA insert in clone s2.12b06 which encodes a soybean S-adenosyl-L-methionine synthetase protein.

SEQ ID NO:2 is the nucleotide sequence comprising a soybean S-adenosyl-L-methionine synthetase genomic DNA fragment.

SEQ ID NO:3 is the nucleotide sequence of a portion of the cDNA insert in clone srr1c.pk002.b21 encoding a portion of a soybean S-adenosyl-L-methionine synthetase protein.

SEQ ID NO:4 is a 32 base oligonucleotide primer, designated sam-5, used to amplify the soybean S-adenosyl-L-methionine synthetase promoter region via PCR.

SEQ ID NO:5 is a 24 base oligonucleotide primer, designated sam-6, used to amplify the soybean S-adenosyl-L-methionine synthetase promoter region via PCR.

SEQ ID NO:6 is the nucleotide sequence comprising a soybean S-adenosyl-L-methionine synthetase promoter fragment produced via PCR using primers sam-5 (SEQ ID NO:4) and sam-6 (SEQ ID NO:5).

SEQ ID NO:7 is a 22 base oligonucleotide primer, designated sam-9, used to amplify the soybean S-adenosyl-L-methionine synthetase promoter region via PCR.

SEQ ID NO:8 is a 19 base oligonucleotide primer, designated atps-9, used to amplify a chimeric gene comprising a SAMS promoter fragment and a portion of the ATP sulfurylase (ATPS) gene via PCR.

SEQ ID NO:9 is a 21 base oligonucleotide primer, designated cgs-8, used to amplify a chimeric gene comprising a SAMS promoter and a portion of the cystathionine-γ-synthase 1 (CGS1) gene via PCR.

SEQ ID NO:10 is a 20 base oligonucleotide antisense primer, designated atps-4, used to amplify the ATP sulfurylase transcript via RT-PCR.

SEQ ID NO:11 is a 21 base oligonucleotide antisense primer, designated cgs-10, used to amplify the cystathionine-γ-synthase 1 transcript via RT-PCR.

SEQ ID NO:12 is a 20 base oligonucleotide primer, designated atps-3, used to amplify an ATP sulfurylase cDNA via PCR.

SEQ ID NO:13 is a 23 base oligonucleotide primer, designated cgs-9, used to amplify a cystathionine-γ-synthase 1 cDNA via PCR.

SEQ ID NO:14 is a 2165 nucleotide sequence comprising a soybean S-adenosyl-L-methionine synthetase genomic DNA fragment which starts at the 5' end of SEQ ID NO:2, and ends at the ATG translation start codon of the S-adenosyl-L-methionine synthetase.

SEQ ID NO:15 is a 1574 nucleotide sequence comprising a DNA fragment which starts at the 5' end of SEQ ID NO:2, and ends at the ATG translation start codon of the S-adenosyl-L-methionine synthetase, and wherein a 591 nucleotide intron sequence has been removed.

SEQ ID NO:16 is a 719 nucleotide sequence comprising a DNA fragment which starts at nucleotide 4 of SEQ ID NO:6, and ends at the ATG translation start codon of the S-adenosyl-L-methionine synthetase, and wherein a 591 nucleotide intron sequence has been removed.

SEQ ID NO:17 is a 6975 nucleotide sequence comprising plasmid pMH40Δ.

SEQ ID NO:18 is a 3985 nucleotide sequence comprising a SAMS promoter::GUS::3' Nos DNA fragment present in plasmid pZSL11.

SEQ ID NO:19 is a 3684 nucleotide sequence comprising a SAMS promoter::ATPS::3' Nos DNA fragment.

SEQ ID NO:20 is a 3963 nucleotide sequence comprising a SAMS promoter::CGS1::3' Nos DNA fragment.

SEQ ID NO:21 is a 4827 nucleotide sequence from pZSL12 comprising a 2.1-kb SAMS promoter::GUS::3' Nos DNA fragment.

SEQ ID NO:22 is a 3939 nucleotide sequence from pZSL13 comprising a 1.3-kb SAMS promoter::herbicide-resistant soybean acetolactate synthase (ALS) coding region::3' soybean ALS DNA fragment.

SEQ ID NO:23 is the amino acid sequence of the herbicide-resistant soybean ALS protein encoded by SEQ ID NO:22.

SEQ ID NO:24 is a 5408 nucleotide sequence from pZSL14 comprising a 2.1-kb SAMS promoter::herbicide-resistant Arabidopsis ALS coding region::3' Arabidopsis ALS DNA fragment.

SEQ ID NO:25 is the amino acid sequence of the herbicide-resistant Arabidopsis ALS protein encoded by SEQ ID NO:24.

SEQ ID NO:26 is the amino acid sequence of the tobacco herbicide-sensitive SURA (ALS I) acetolactate synthase protein (NCBI General Identifier No. 124367).

SEQ ID NO:27 is the amino acid sequence of the tobacco herbicide-sensitive SURB (ALS II) acetolactate synthase protein (NCBI General Identifier No. 124369).

SEQ ID NO:28 is the amino acid sequence of the *Brassica napus* herbicide-sensitive acetolactate synthase 3 protein (NCBI General Identifier No. 320131).

SEQ ID NO:29 is the amino acid sequence of the *Arabidopsis thaliana* herbicide-sensitive acetolactate synthase protein (NCBI General Identifier No. 124372).

SEQ ID NO:30 is the amino acid sequence of the soybean herbicide-sensitive acetolactate synthase protein.

FIGS. 1A and 1B depict Southern hybridization analyses of SAMS genes. Soybean genomic DNA was digested with BamHI, EcoRI, HindIII, KpnI, and SacI, and then the blot was hybridized with a full length SAMS cDNA (SEQ ID NO:1) probe in FIG. 1A or with a SAMS promoter fragment (SEQ ID NO:6) probe in FIG. 1B.

FIG. 2 depicts a SAMS genomic DNA sequence (SEQ ID NO:2) and the alignment of the overlapping region with SAMS cDNA sequence (SEQ ID NO:1). The 2336 bp SAMS genomic DNA sequence has a 191 bp region aligned with the 5' end sequence of the SAMS cDNA with six mismatches. The region used to make the SAMS promoter by adding the NcoI site at its 3' end is underlined. The translation start codon is in bold.

FIG. 3 depicts the structure of the SAMS::GUS expression cassette. The SAMS promoter was cloned into pMH40A to replace its 35S promoter. The structure of the resulted SAMS::GUS construct was generated by Vector NTI™ software (InforMax, Inc., North Bethesda, Md.).

FIG. 4 depicts a histochemical GUS expression analysis of transgenic *Arabidopsis* plants harboring the SAMS::GUS expression cassette. *Arabidopsis* tissues were incubated at 37° C. with X-Gluc overnight and dehydrated with ethanol. (A) Flower buds; (B) leaf; (C) Inflorescence stem and a cauline leaf; (D, E, F) developing siliques; (G) Developing seeds and embryos. All of the seeds were derived from GUS-positive siliques. Genetic segregation of the GUS gene was demonstrated by the blue funiculus of the white seed in the right upper corner.

FIG. 5 depicts a fluorometric GUS expression assay of transgenic *Arabidopsis* plants harboring the SAMS::GUS expression cassette. Triple samples of flowers, leaves, stems, siliques coats, young seeds, medium seeds, old seeds, and dry seeds collected from SAMS::GUS transgenic *Arabidopsis* plants were assayed for GUS activity. The graph was generated by Microsoft Excel and the standard deviation is indicated by the upper part of each column.

FIG. 6 depicts a histochemical GUS transient expression analysis of SAMS promoter in corn. The pZSL11 (SAMS::GUS) or the pMH40Δ (35S::GUS) plasmid DNA was delivered into corn callus (A, C) or leaf discs (B, D), and the GUS activity was detected by incubation with X-Gluc overnight at 37° C. (A, B) Transformed with pZSL11 DNA; (C, D) Transformed with pMH40Δ DNA.

FIGS. 7(A) and 7(B) depict the presence and expression of transgenic soybean ATPS and CGS1 genes controlled by the SAMS promoter in transgenic *Arabidopsis* plants. FIG. 7(A) is a PCR analysis. Genomic DNA of ten transgenic *Arabidopsis* plants (1 to 10), wild type *Arabidopsis* (a), wild type soybean (s), and plasmid DNA of SAMS::CGS1 or SAMS::ATPS in binary vectors (p) were used as templates in PCR with gene-specific primers. PCR of ten SAMS::CGS1 transgenic plants with primer sam-9 which is specific to SAMS promoter, and primer cgs-8 which is specific to soybean CGS1 (upper). PCR of ten SAMS::ATPS transgenic plants with primer sam-9 which is specific to SAMS promoter, and primer atps-1 which is specific to soybean ATPS gene (lower). FIG. 7(B) is an RT-PCR analysis. Total leaf RNA of ten transgenic *Arabidopsis* plants (1 to 10), wild type *Arabidopsis* (a), and wild type soybean (s) were used as templates in RT-PCR with gene-specific primers. First strand cDNA was synthesized from a gene-specific antisense primer with reverse transcriptase, and then the first strand cDNA was amplified by PCR with both sense and antisense primers. RT-PCR of ten SAMS::CGS1 transgenic plants with primers, cgs-9 (sense) and cgs-10 (antisense), specific to soybean CGS1 gene (upper). RT-PCR of ten SAMS::ATPS transgenic plants with primers, atps-3 (sense) and atps-4 (antisense), specific to soybean ATPS gene (lower).

FIG. 8 depicts induction of SAMS promoter activity by methionine. Seeds of ten transgenic *Arabidopsis* lines transformed with SAMS::GUS construct were germinated on filter papers soaked with $H_2O$, 1× Murashige and Skoog salt, 0.01 mM, and 1 mM methionine. Ten days old seedlings were harvested and assayed for GUS activity. The solid bar and hollow bar indicate, respectively, the average and the standard variation of three samples for each treatment.

FIG. 9 depicts a northern hybridization. Soybean total RNAs from leaves, roots, stems, young seeds, medium seeds, old seeds, and pod coats (L, R, S, Y, M, O, and P) were used to make the RNA blot which was hybridized with a full length SAMS cDNA (SEQ ID NO:1) probe.

FIGS. 10A, 10B and 10C depict an amino acid sequence alignment of the following herbicide-sensitive acetolactate synthase (ALS) proteins: a tobacco SURB (ALS II) protein (SEQ ID NO:27; NCBI General Identifier No. 124369); a *Brassica napus* ALS3 (AHAS3) protein (SEQ ID NO:28; NCBI General Identifier No. 320131); an *Arabidopsis thaliana* ALS protein (SEQ ID NO:29; NCBI General Identifier No. 124372); and a soybean ALS protein (SEQ ID NO:30). The numbering for the consensus amino acid sequence is shown below. The numbering for each ALS sequence is shown to the left of each row and to the right of the final row. Amino acids which are conserved among all four sequences are indicated with an asterisk above the amino acid residue. Shown below the four sequences are seven conserved amino acid regions, subfragments "A" through "G" described in U.S. Pat. No. 5,013,659, in which changes in particular amino acid residues can lead to herbicide resistance. A caret below the lysine residue at consensus amino acid position 98 indicates the start of the mature ALS polypeptide. The chloroplast transit peptide for each ALS protein is within consensus amino acid region 1-97.

DETAILED DESCRIPTION OF THE INVENTION

Figures 1A, 1B:
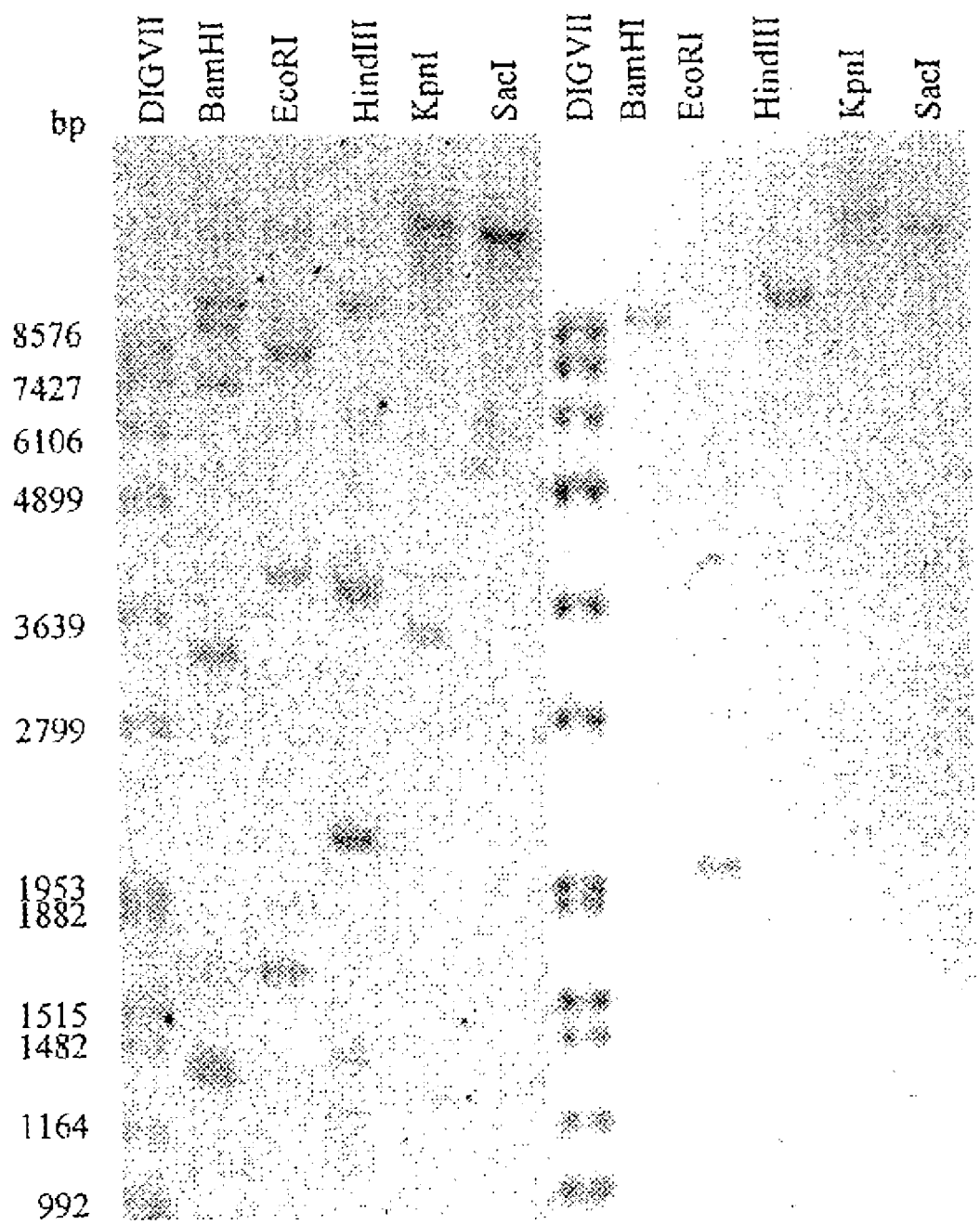

In the context of this disclosure, a number of terms shall be utilized.

As used herein, an "isolated nucleic acid fragment" is a polymer of ribonucleotides (RNA) or deoxyribonucleotides (DNA) that is single- or double-stranded, optionally containing synthetic, non-natural or altered nucleotide bases. An isolated nucleic acid fragment in the form of DNA may be comprised of one or more segments of cDNA, genomic DNA or synthetic DNA.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under stringent or moderately stringent conditions (for example, 0.5×SSC, 0.1% SDS, 60° C.) with the sequences exemplified herein, or to any portion of the nucleotide sequences reported herein and which are functionally equivalent to the promoter of the invention. Stringent hybridization conditions using 50% formamide can be found in Current Protocols in Molecular Biology, edited by F. M. Ausubel, R. Brent, R. E. Kingston, D. D. Moore, J. G. Seidman, J. A. Smith, and K. Struhl, John Wiley & Sons, New York, 1992. A formamide stringent hybridization buffer can contain the following: 50% formamide; 5×SSC; 20 mM Tris-Cl, pH 7.6; 1×Denhardt's solution; 10% dextran sulfate; and 1% SDS. Hybridization can occur at 42° C. in the above buffer with an overnight incubation. Washes can be done in 2×SSC, 0.1% SDS, for 15 minutes and then three 15 minutes washes in 0.2×SSC, 0.1% SDS, before exposure to film. A 100×Denhardt's solution can be prepared in the following manner: 2 g bovine serum albumin; 2 g Ficoll 400; 2 g Polyvinylpyrrolidone; add appoximately 50 ml of distilled water; mix to dissolve; make up to a final volume of 100 ml and store at −20° C. Alternatively, stringent hybridization conditions can use DIG Easy Hyb buffer (Roche Diagnostics Corp.). DIG Easy Hyb is non-toxic and does not contain formamide, yet the hybridization temperature should be calculated with the same equation that is used for buffer containing 50% formamide. A hybridization temperature of 45° C., 55° C., or any integer degree between 45° C. and 55° C., can be used for hybridization of homologous probes to plant genomic DNA. Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. Useful examples of preferred percent identities are any integer percentage from 80% to 100%. Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS*. 5:151-153) with the default parameters (GAP PENALTY=10, GAP LENGTH PENALTY=10). Default parameters for pairwise alignments and calculation of percent identiy of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) *J. Mol. Biol.* 215:403-410) and Gapped Blast (Altschul, S. F. et al., (1997) *Nucleic Acids Res.* 25:3389-3402).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

A "heterologous nucleic acid fragment" refers to a nucleic acid fragment comprising a nucleic acid sequence that is different from the nucleic acid sequence comprising the plant promoter of the invention.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". In particular, a constitutive promoter refers to a promoter which causes a gene to be expressed in at least the following types of plant tissue: leaf, root, stem, seed and callus. New promoters of various types useful in plant cells are constantly being discovered; numerous examples may be found in the compilation by Okamuro and Goldberg (1989, *Biochemistry of Plants* 15:1-82). It is further recognized that since in most cases the exact boundaries of regulatory sequences have not been completely defined, DNA fragments of some variation may have identical promoter activity. An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

"Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product. Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

"Altered expression" refers to the production of gene product(s) in transgenic organisms in amounts or proportions that differ significantly from the amount of the gene product(s) produced by the corresponding wild-type organisms.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transferred nucleic acid fragments are referred to as "transgenic" or "transformed" organisms. The preferred method of cell transformation of rice, corn and other monocots is the use of particle-accelerated or "gene gun" transformation technology (Klein et al, (1987) *Nature (London)* 327:70-73; U.S. Pat. No. 4,945,050), or an *Agrobacterium*-mediated method using an appropriate Ti plasmid containing the transgene (Ishida Y. et al, 1996, Nature Biotech. 14:745-750).

"Regeneration medium" (RM) promotes differentiation of totipotent embryogenic plant tissues into shoots, roots and other organized structures and eventually into plantlets that can be transferred to soil.

"Plant culture medium" is any medium used in the art for supporting viability and growth of a plant cell or tissue, or for growth of whole plant specimens. Such media commonly include, but are not limited to, macronutrient compounds providing nutritional sources of nitrogen, phosphorus, potassium, sulfur, calcium, magnesium, and iron; micronutrients, such as boron, molybdenum, manganese, cobalt, zinc, copper, chlorine, and iodine; carbohydrates; vitamins; phytohormones; selection agents; and may include undefined components, including, but not limited to, casein hydrolysate, yeast extract, and activated charcoal. The medium may be either solid or liquid.

"Plant cell" is the structural and physiological unit of plants, consisting of a protoplast and the cell wall.

"Plant tissue" is a group of plant cells organized into a structural and functional unit.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises an isolated polynucleotide operably linked to at least one regulatory sequence. The term also embraces an isolated polynucleotide comprising a region encoding all or part of a functional RNA and at least one of the naturally occurring regulatory sequences directing expression in the source (e.g., organism) from which the polynucleotide was isolated, such as, but not limited to, an isolated polynucleotide comprising a nucleotide sequence encoding a herbicide resistant target gene and the corresponding promoter and 3' end sequences directing expression in the source from which sequences were isolated. The terms "recombinant DNA construct", "recombinant construct" and "chimeric gene" are used interchangeably herein.

A "transgene" is a recombinant DNA construct that has been introduced into the genome by a transformation procedure.

"Selection agent" refers to a compound which is toxic to non-transformed plant cells and which kills non-transformed tissues when it is incorporated in the culture medium in an "effective amount", i.e., an amount equal to or greater than the minimal amount necessary to kill non-transformed tissues. Cells can be transformed with an appropriate gene, such that expression of that transgene confers resistance to the corresponding selection agent, via de-toxification or another mechanism, so that these cells continue to grow and are subsequently able to regenerate plants. The gene conferring resistance to the selection agent is termed the "selectable marker gene", "selectable marker" or "resistance gene". Transgenic cells that lack a functional selectable marker gene will be killed by the selection agent. Selectable marker genes include genes conferring resistance to herbicidal compounds. Herbicide resistance genes generally code for a modified target protein insensitive to the herbicide or for an enzyme that degrades or detoxifies the herbicide in the plant before it can act (DeBlock et al., 1987, *EMBO J.* 6:2513-2518, DeBlock et al., 1989, *Plant Physiol.*, 91: 691-704). For example, resistance to glyphosate or sulfonylurea herbicides has been obtained by using genes coding for mutant versions of the target enzymes, 5-enolpyruvylshikimate-3-phosphate synthase (EPSPS) and acetolactate synthase (ALS), respectively. Resistance to glufosinate ammonium, bromoxynil and 2,4-dichlorophenoxyacetic acid (2,4-D) has been obtained by using bacterial genes encoding phosphinothricin acetyltransferase, a nitrilase, or a 2,4-dichlorophenoxyacetate monooxygenase, respectively, which detoxify the respective herbicide. "Sulfonylurea herbicides" include but are not limited to Rimsulfuron, Nicosulfuron, Classic, and Oust. A specific selection agent may have one or more corresponding selectable marker genes. Likewise, a specific selectable marker gene may have one or more corresponding selection agents. It is appreciated by one skilled in the art that a selection agent may not be toxic to all plant species or to all cell types within a given plant. For a plant species susceptible to a given selection agent, it is also appreciated that resistance cells, tissues or whole plants may be obtained independent of the transformation process, e.g., through chemical mutagenesis of the target gene or gene amplification of the target gene during tissue culture.

Examples of suitable selection agents, include but are not limited to, cytotoxic agents such as hygromycin, sulfonylurea herbicides such as Nicosulfuron and Rimsulfuron, and other herbicides which act by inhibition of the enzyme acetolactate synthase (ALS), glyphosate, bialaphos and phosphinothricin (PPT). It is also possible to use positive selection marker systems such as phospho-mannose isomerase and similar systems which confer positive growth advantage to transgenic cells.

Any regenerable plant tissue can be used in accordance with the present invention. Regenerable plant tissue generally refers to tissue which can be regenerated into a differentiated plant. For example, such tissues can include calluses and/or somatic embryos derived from whole zygotic embryos, isolated scutella, anthers, inflorescences and leaf and meristematic tissues.

In order to identify transformed tissues, cultures may be exposed to a selection agent appropriate to a selectable marker gene included in the recombinant DNA construct used for transformation. The selection agent may be supplied during the callus induction or proliferation phases of culture, or may be supplied during culture on regeneration medium. Single, or more commonly multiple passages of selection may be applied. Even when a resistance gene is expressed in transformed tissues it is common for the application of selection to reduce the efficiency of formation of regenerable tissue from transformed cells (e.g. to reduce the frequency of somatic embryogenesis). Thus, it is preferable to supply the selection agent during the regeneration phase of culture rather than during the induction phase in order to increase the efficiency of formation of regenerable tissue from transformed cells.

Standard recombinant DNA and molecular cloning techniques used herein are well known in the art and are described more fully in Sambrook, J., Fritsch, E. F. and Maniatis, T., *Molecular Cloning: A Laboratory Manual*; Cold Spring Harbor Laboratory Press, Cold Spring Harbor, 1989 (hereinafter "Sambrook et al., 1989") or Ausubel, F. M., Brent, R., Kingston, R. E., Moore, D. D., Seidman, J. G., Smith, J. A. and Struhl, K. (eds.), *Current Protocols in Molecular Biology*, John Wiley and Sons, New York, 1990 (hereinafter "Ausubel et al., 1990").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

An "expression construct" is a plasmid vector or a subfragment thereof comprising the instant recombinant DNA construct. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis. The terms "expression construct", "expression cassette" and "recombinant expression construct" are used interchangeably herein.

Although the SAMS enzyme is present in most plant cell types, no SAMS promoter capable of driving gene expression in most or all plant cell types has been described. Previous studies indicated that plants contain multiple SAMS genes which are differentially expressed in response to various stresses (Schroder et al. (1997) Plant Mol. Biol. 33:211-222). A SAMS promoter that is preferentially active in a particular tissue type, i.e. vascular (Peleman et al., (1989) Plant Cell 1, 81-93; Mijnsbrugge et al., (1996) Plant Cell Physiol. 37, 1108-1115), was also known. However, it was not possible to predict, before the studies reported herein, whether any SAMS gene was controlled by a constitutive promoter. It is demonstrated herein that constitutive SAMS promoters do, in fact, exist in plants, and that such promoters can be readily isolated and used by one skilled in the art.

This invention concerns an isolated nucleic acid fragment comprising a constitutive plant SAMS promoter. This invention also concerns an isolated nucleic acid fragment comprising a promoter wherein said promoter consists essentially of the nucleotide sequence set forth in SEQ ID NOs:6, 14, 15 or 16 or said promoter consists essentially of a fragment or subfragment that is substantially similar and functionally equivalent to the nucleotide sequence set forth in SEQ ID NOs:6, 14, 15 or 16. A nucleic acid fragment that is functionally equivalent to the instant SAMS promoter is any nucleic acid fragment that is capable of controlling the expression of a coding sequence or functional RNA in a similar manner to the SAMS promoter. The expression patterns of the SAMS promoter are defined in the following paragraphs.

Figure 9:
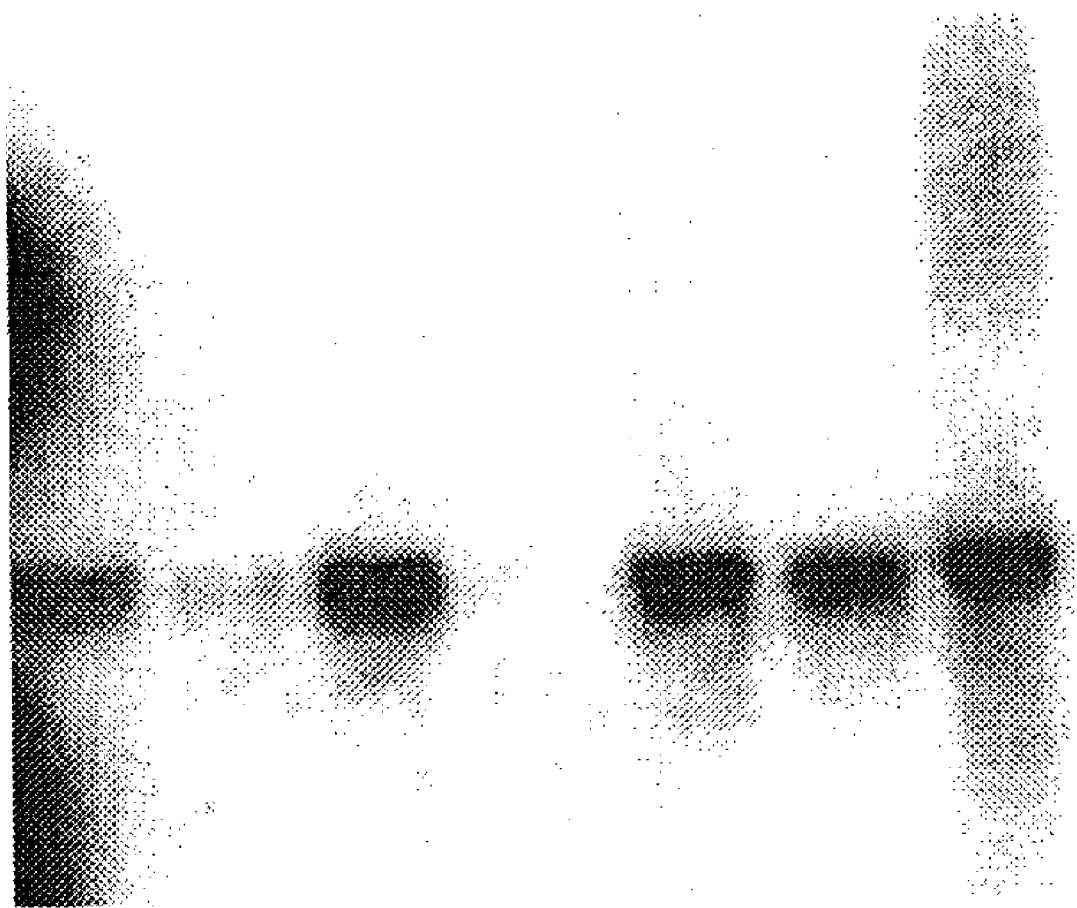

Northern-blot hybridization experiments indicated that SAMS gene transcripts are present in a variety of soybean tissues and that the abundance of SAMS gene transcripts does not differ greatly from tissue to tissue (FIG. 9 and Example 3). Strong expression of the SAMS gene was also inferred by the high frequency of occurrences of cDNA sequences with homology to SAMS (ESTs) in a soybean cDNA sequence database created by sequencing random cDNAs from libraries prepared from many different soybean tissues. ESTs encoding SAMS can be easily identified by conducting BLAST (Basic Local Alignment Search Tool; Altschul, S. F., et al., (1993) J. Mol. Biol. 215:403-410) searches for similarity to sequences contained in the BLAST "nr" database, e.g., SAMS from *Oryza sativa* (EMBL Accession No. Z26867) or SEQ ID NO:1 provided herein. SAMS homologs were among the most abundant classes of cDNAs found in the soybean libraries. This indicated that SAMS was a highly expressed gene in most soybean cell types. The data obtained from sequencing many SAMS ESTs also indicated that there were several SAMS isoforms encoded by the soybean genome.

A soybean cDNA clone designated s2.12b06 was found to encode a protein which is very similar to the protein encoded by the cDNA to *Oryza sativa* SAMS (pLog value for this match was 61.59). The soybean cDNA clone designated s2.12b06 was completely sequenced (SEQ ID NO:1) and found to contain an opening reading frame which encodes a full length SAMS polypeptide. Southern hybridization analysis of soybean genomic DNA with this full length SAMS cDNA as a probe suggested that there are approximately four related SAMS genes in the soybean genome (FIG. 1A), which is consistent with the EST sequencing data.

The soybean SAMS cDNA clone was used to isolate a soybean genomic DNA fragment containing more than 2000 nucleotides upstream (5') of the SAMS protein coding sequence by hybridization of a soybean genomic DNA library to the SAMS cDNA fragment probe. Southern hybridization analysis of soybean genomic DNA using a 1314 base pair DNA fragment from upstream of the SAMS protein coding sequence as a probe indicated that this fragment is unique in the soybean genome (FIG. 1B).

Figure 8:
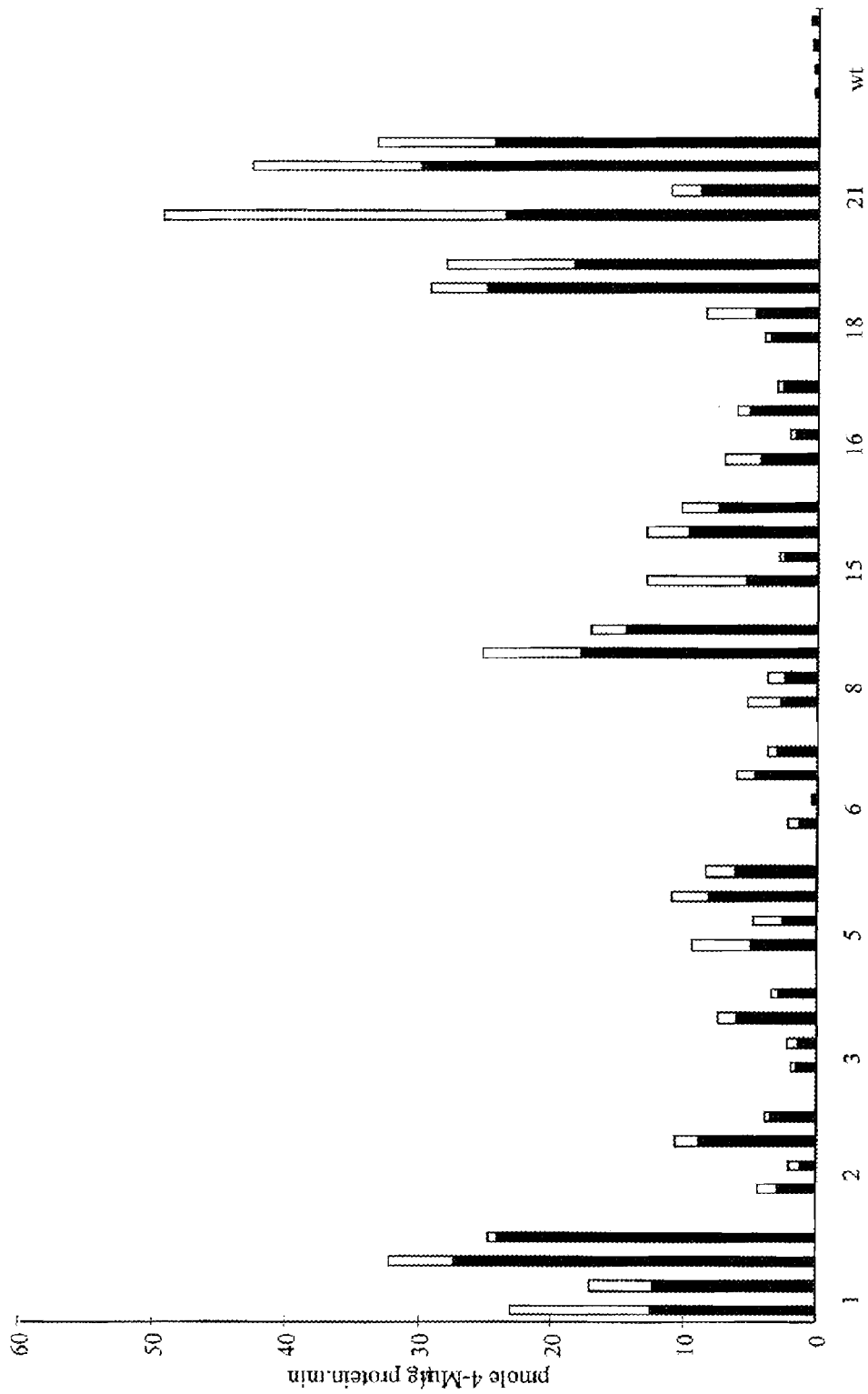

The promoter activity of the soybean genomic DNA fragment upstream of the SAMS protein coding sequence was assessed by linking the fragment to a reporter gene, the *E. coli* β-glucuronidase gene (GUS) (Jefferson (1987) Plant Mol. Biol. Rep. 5:387-405), transforming the SAMS promoter::GUS expression cassette into *Arabidopsis*, and analyzing GUS expression in various cell types of the transgenic plants. GUS expression was detected in all parts of the transgenic plants that were analyzed. These results indicated that the nucleic acid fragment contained a constitutive promoter. Since SAMS catalyzes the reaction to synthesize S-adenosyl-L-methionine from methionine and ATP, free methionine levels might regulate SAMS promoter activity. To see if the SAMS promoter is regulated by external methionine, the SAMS::GUS transgenic *Arabidopsis* seeds were germinated in the presence or absence of methionine. Ten day old seedlings were analyzed for GUS activity according to the protocol described in Example 5. Ten independent transgenic lines were tested and all of them responded similarly. GUS activity was more than two-fold higher in seedlings germinated in the presence of methionine (FIG. 8). The increased SAMS promoter activity in the presence of methionine may be particularly useful for efforts to increase methionine biosynthesis via overexpression of enzymes in the methionine biosynthetic pathway or the sulfate assimilation pathway. It is clear from the disclosure set forth herein that one of ordinary skill in the art could readily isolate a constitutive plant SAMS promoter from any plant by performing the following procedure:

1) obtaining a SAMS cDNA from a desired plant by any of a variety of methods well known to those skilled in the art including, but not limited to, (a) random sequencing of ESTs from a cDNA library and characterizing the ESTs via a BLAST search as described above; or (b) hybridizing a cDNA library to a known plant SAMS cDNA; or (c) PCR amplification using oligonucleotide primers designed from known SAMS cDNAs;

2) obtaining a genomic DNA fragment that includes approximately 500 to 3000 nucleotides from the region 5' to a SAMS protein coding sequence, which contains a SAMS promoter, by hybridization of a genomic DNA library to a SAMS cDNA fragment probe;

3) operably linking the nucleic acid fragment containing the region upstream (5') of the SAMS protein coding sequence to a suitable reporter gene; there are a variety of reporter genes that are well known to those skilled in the art, including the bacterial GUS gene, the firefly luciferase gene, and the green fluorescent protein gene; any gene for which an easy an reliable assay is available can serve as the reporter gene 4) transforming a chimeric SAMS promoter::reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm. The terms "oilseed rape" and "oilseed *Brassica*" are used interchangeably herein.

5) testing for expression of a SAMS promoter in various cell types of transgenic plants, e.g., leaves, roots, flowers, seeds, transformed with the chimeric SAMS promoter::reporter gene expression cassette by assaying for expression of the reporter gene product. A constitutive SAMS promoter will produce high level expression of the reporter in all, or nearly all, of the plant tissues tested.

In another aspect, this invention concerns a chimeric gene comprising at least one heterologous nucleic acid fragment operably linked to the promoter of the present invention. Chimeric genes can be constructed by operably linking the nucleic acid fragment of the invention, i.e., the SAMS promoter or a fragment or a subfragment that is substantially similar and functionally equivalent to any portion of the nucleotide sequence set forth in SEQ ID NOS:6, 14, 15 or 16, to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation.

Plasmid vectors comprising the instant chimeric genes can then be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

The plasmid vectors or chimeric genes can be used to transform plant cells. Transformation techniques are well known to those skilled in art as discussed above. A preferred method of plant cell transformation is the use of particle-accelerated or "gene gun" transformation technology (Klein et al. (1978) *Nature* (London) 327:70-73; U.S. Pat. No. 4,945,050). The chimeric gene will normally be joined to a marker for selection in plant cells. The particular marker employed will be one which will allow for selection of transformed cells as compared to cells lacking the heterologous nucleic acid sequence which has been introduced. Examples of plant cells which can be transformed using plant transformation techniques include, but are not limited to, monocot and dicot plant cells such as soybean, oilseed *Brassica* species, corn, peanut, rice, wheat, sunflower, safflower, cotton, cocoa, tobacco, tomato, potato, barley, palm, *Arabidopsis* and the like.

In addition to the bacterial GUS gene, two soybean genes, ATP sulfurylase (ATPS) and cystathionine-γ-synthase 1 (CGS1), were also successfully expressed by this promoter in transgenic *Arabidopsis*, as depicted in FIG. 7. This further validates the application of the SAMS promoter of the invention in plant genetic engineering practice.

The skilled artisan will also recognize that different independent transformation events will result in different levels and patterns of expression of the chimeric genes (Jones et al., (1985) *EMBO J.* 4:2411-2418; De Almeida et al., (1989) *Mol. Gen. Genetics* 218:78-86). Thus, multiple events must be screened in order to obtain lines displaying the desired expression level and pattern. Such screening may be accomplished by northern analysis of mRNA expression, western analysis of protein expression, or phenotypic analysis. Also of interest are seeds obtained from transformed plants displaying the desired expression profile.

The level of activity of the SAMS promoter is comparable to that of many known strong promoters, such as the CaMV 35S promoter (Atanassova et al., (1998) *Plant Mol. Biol.* 37:275-285; Battraw and Hall, (1990) *Plant Mol. Biol.* 15:527-538; Holtorf et al., (1995) *Plant Mol. Biol.* 29:637-646; Jefferson et al., (1987) *EMBO J.* 6:3901-3907; Wilmink et al., (1995) *Plant Mol. Biol.* 28:949-955), the *Arabidopsis* oleosin promoters (Plant et al., (1994) *Plant Mol. Biol.* 25:193-205; Li, (1997) Texas A&M University Ph.D. dissertation, pp. 107-128), the *Arabidopsis* ubiquitin extension protein promoters (Callis et al., 1990), a tomato ubiquitin gene promoter (Rollfinke et al., 1998), a soybean heat shock protein promoter (Schoffl et al., 1989), and a maize H3 histone gene promoter (Atanassova et al., 1998).

Expression of the chimeric genes in most plant cell makes the SAMS promoter of the instant invention especially useful when constitutive expression of a target heterologous nucleic acid fragment is required. Examples of suitable target heterologous nucleic acid fragments include, but are not limited to, a herbicide-resistance or pathogen-resistance nucleic acid fragment. Three classes of herbicides, the sulfonylureas, triazolo-pyrimidine sulfonamides, and imidazolinone herbicides, inhibit growth of some bacteria, yeast and higher plants by blocking acetolactate synthase [ALS, EC 4.1.3.18]. These three classes of herbicides are referred to as "inhibitors of ALS". ALS is the first common enzyme in the biosynthesis of the branched-chain amino acids valine, leucine and isoleucine. Mutations in ALS have been identified that convey resistance to some or all of these three inhibitors of ALS (U.S. Pat. No. 5,013,659; the entire contents of which are herein incorporated by reference). Sulfonylureas are described in the following U.S. Pat. Nos. 4,127,405; 4,169,719; 4,190,432; 4,214,890; 4,225,337; 4,231,784; 4,257,802; 4,310,346; 4,544,401; 4,435,206; 4,383,113; 4,394,153; 4,394,506; 4,420,325; 4,452,628; 4,481,029; 4,586,950; 4,514,212; 4,634,465; and in EP-A-204,513. Triazolopyrimidine sulfonamides are described in South African Application 84/8844, published May 14, 1985. Imidazolinones are described in U.S. Pat. No. 4,188,487; and in EP-A-41,623, published Dec. 16, 1981. Two ALS genes in tobacco have been identified and are called SURA (or ALS I) and SURB (or ALS II). A double-mutant of the SURB gene in tobacco was generated, that conveys high-level resistance to inhibitors of ALS, and was designated Hra. The corresponding mutant ALS gene, designated SURB-Hra gene, encodes a herbicide-resistant ALS with the following two mutations in the amino acid sequence of the protein: the proline at position 191, in the conserved "subsequence B", G-Q-V—P (SEQ ID NO:31), has been changed to alanine; and the tryptophan at position 568, in the conserved "subsequence F", G-M-V—V/M-Q-W-E-D-R—F (SEQ ID NO:32), has been changed to leucine (U.S. Pat. No. 5,013,659; Lee et al. (1988) EMBO J 7:1241-1248). A single mutation in a *Brassica napus* ALS gene has been identified that conveys resistance to sulfonylureas, imidazolinones and triazolopyrimidines (Hattori et al. (1995) Mol Gen Genet 246:419-425). The mutation in the ALS3 (AHAS3) gene results in a change of tryptophan to leucine in the conserved "subsequence F" region, G-M-V—V/M-Q-W-E-D-R—F (SEQ ID NO:32), which corresponds to one of the two mutations contained in the herbicide-resistant SURB-Hra gene.

Figure 4A:
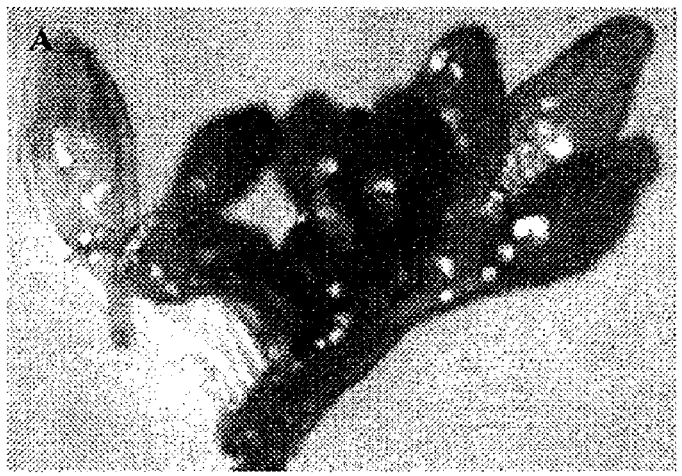
Figure 4B:
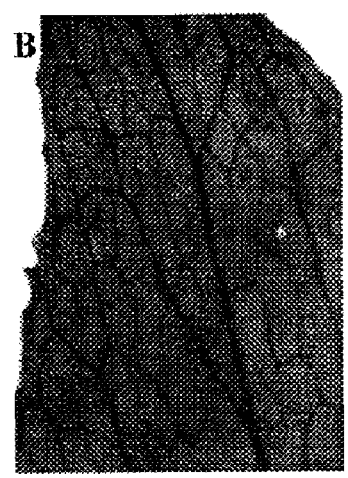
Figure 4C:
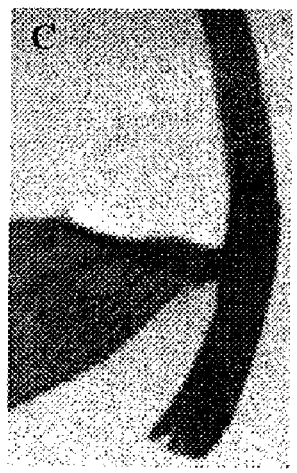
Figure 4D:
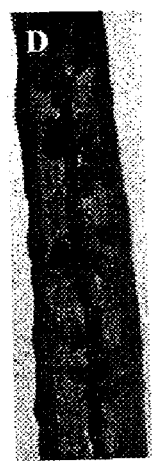
Figure 4E:
Figure 4F:
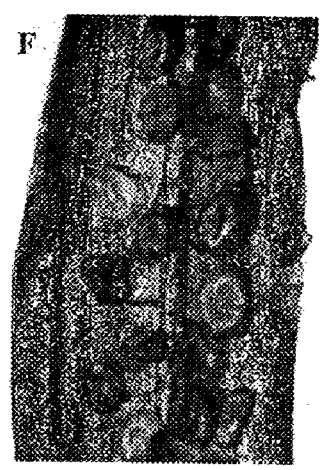
Figure 4G:
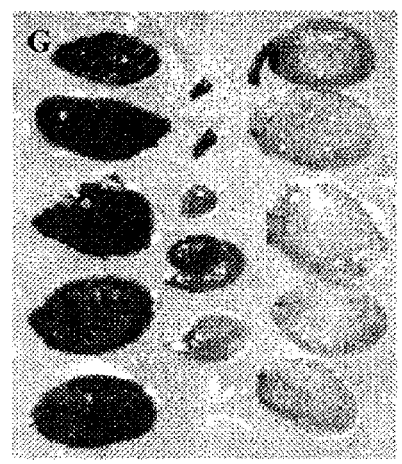
Figure 5:
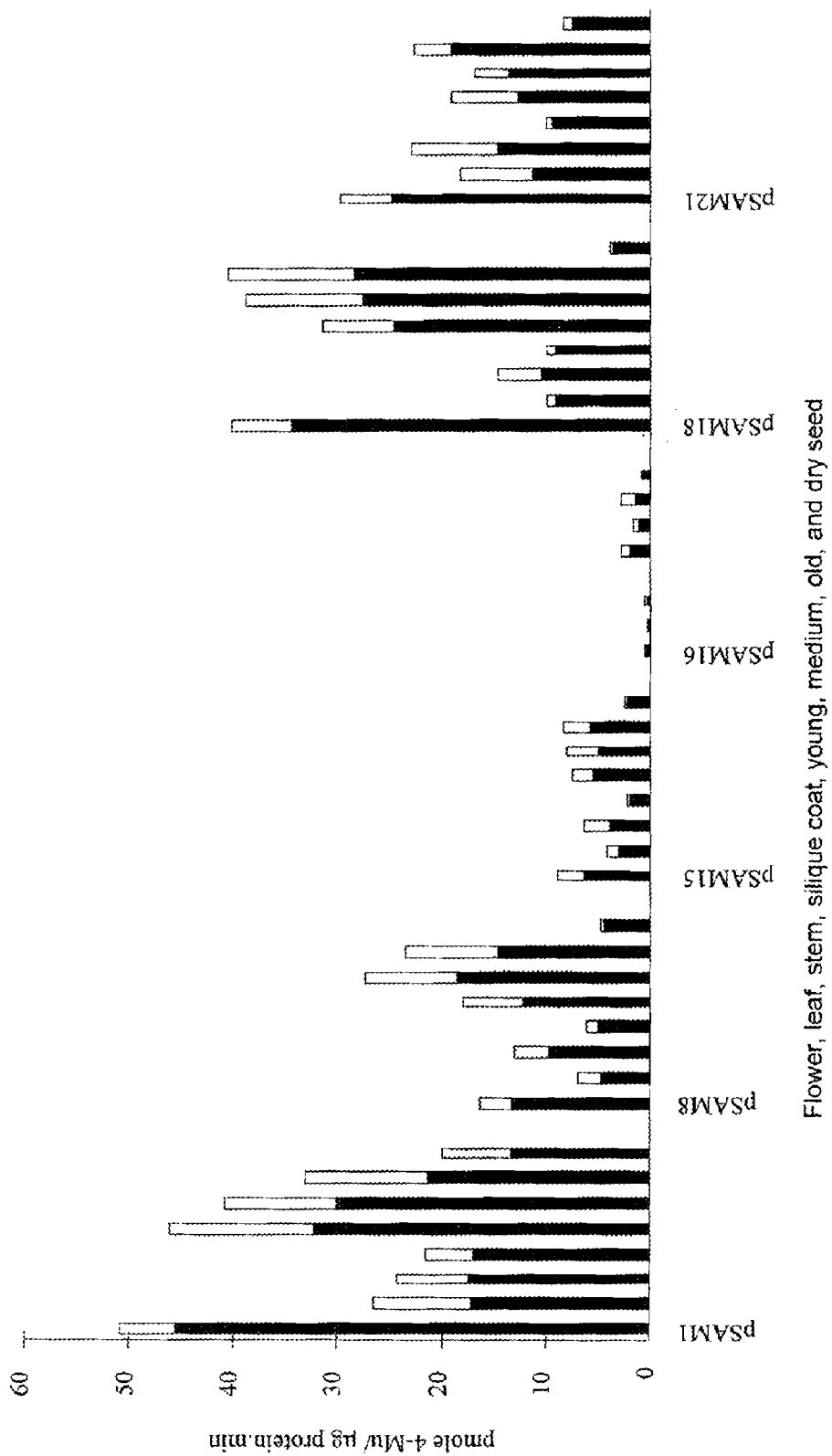

Another useful feature of the constitutive plant SAMS promoter is its expression profile in developing seeds. The SAMS promoter of the invention is most active in developing seeds at early stages and gradually turns down at later stages. Such activity is indicated by the GUS activity detected in seeds of transgenic *Arabidopsis* plants containing a SAMS::GUS expression cassette as shown in FIGS. 4 and 5. The expression profile of the claimed SAMS promoter is different from that of many seed-specific promoters, e.g., seed storage protein promoters, which often provide highest activity in later stages of development (Chen et al., (1989) *Dev. Genet.* 10:112-122; Ellerstrom et al., (1996) *Plant Mol. Biol.* 32:1019-1027; Keddie et al., (1994) *Plant Mol. Biol.* 24:327-340; Plant et al., (1994) *Plant Mol. Biol.* 25:193-205; Li, (1997) Texas A&M University Ph.D. dissertation, pp. 107-128). Thus, the SAMS promoter will be a very attractive candidate when overexpression of a gene in embryos is desired at an early developing stage. For example, it may be desirable to overexpress a gene regulating early embryo development or a gene involved in the metabolism prior to seed maturation.

One general application of the SAMS promoter of the invention is to construct chimeric genes that can be used in the selection of transgenic cell lines in plant transformation. Currently, many of the selectable marker genes for plant transformation are under the control of the cauliflower mosaic virus 35S promoter. Since the SAMS promoter of the invention is active in seedlings and callus, the appropriate selection phase for transgenic plants or cell lines, this promoter may be used as an alternative to the 35S promoter to drive the expression of selectable marker genes.

Another general application of the SAMS promoter of the invention is to construct chimeric genes that can be used to reduce expression of at least one heterologous nucleic acid fragment in a plant cell. To accomplish this a chimeric gene designed for cosuppression of a heterologous nucleic acid fragment can be constructed by linking the fragment to the SAMS promoter of the present invention. (See U.S. Pat. No. 5,231,020 for methodology to block plant gene expression via cosuppression.) Alternatively, a chimeric gene designed to express antisense RNA for a heterologous nucleic acid fragment can be constructed by linking the fragment in reverse orientation to the SAMS promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of increasing or decreasing the expression of at least one heterologous nucleic acid fragment in a plant cell which comprises:
(a) transforming a plant cell with the chimeric genes described herein;
(b) growing fertile plants from the transformed plant cell of step (a);
(c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

EXAMPLES

The present invention is further defined in the following Examples. From the above discussion and these Examples, one skilled in the art can ascertain the essential characteristics of this invention, and without departing from the spirit and scope thereof, can make various changes and modifications of the invention to adapt it to various usages and conditions.

Unless otherwise stated, all parts and percentages are by weight and degrees are Celsius. Techniques in molecular biology were typically performed as described in Ausubel, F. M., et al., (1990, Current Protocols in Molecular Biology, John Wiley and Sons, New York) or Sambrook, J. et al., (1989, Molecular cloning—A Laboratory Manual, $2^{nd}$ ed. Cold Spring Harbor Laboratory Press, Cold Spring Harbor, N.Y.).

Example 1

Composition of cDNA Libraries; Isolation and Sequencing of cDNA Clones cDNA libraries representing mRNAs from soybean tissues were prepared in Uni-ZAP XR™ vectors according to the manufacturer's protocol (Stratagene, La Jolla, Calif.). Conversion of the Uni-ZAP XR™ libraries into plasmid libraries was accomplished according to the protocol provided by Stratagene. Upon conversion, cDNA inserts were contained in the plasmid vector pBluescript™ (Stratagene). DNA was prepared for sequencing from randomly selected bacterial colonies containing recombinant pBluescript™ plasmids either by amplifying the cDNA inserts via polymerase chain reaction using primers specific for vector sequences flanking the cloning site or by preparing plasmid DNA from cultured bacterial cells. Amplified insert DNAs or plasmid DNAs were sequenced in dye-primer sequencing reactions using a Perkin Elmer Model 377 fluorescent sequencer to generate partial cDNA sequences termed expressed sequence tags or "ESTs" (see Adams, M. D. et al., (1991) *Science* 252:1651).

Example 2

Identification of SAMS cDNA Clones

ESTs encoding SAMS were identified by conducting BLAST (Basic Local Alignment Search Tool; Altschul, S. F., et al., (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266-272 and Altschul, S. F., et al. (1997) *Nucleic Acids Res.* 25:3389-3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone s2.12b06 revealed that this nucleotide sequence encoded a protein that was similar to the protein encoded by the cDNA to *Oryza sativa* (EMBL Accession No. Z26867) S-adenosylmethionine synthetase; the pLog value for this match was 61.59. This cDNA clone was completely sequenced (SEQ ID NO:1) and found to contain an opening reading frame ranging from nucleotides 74 to 1252 which is predicted to encode a full length SAMS polypeptide.

A high level of expression of the SAMS genes was inferred by the high frequency of occurrences of soybean cDNA sequences with homology to *Oryza sativa* SAMS obtained from many different cDNA libraries prepared from many different soybean cell types. SAMS homologs were the third most abundant class of ESTs found in the soybean libraries. Although the ranking might not represent a precise estimate of the relative abundance of the SAMS transcripts in vivo in all soybean libraries, due to the selective use of different cDNA libraries, it did indicate that SAMS was a highly expressed gene. The EST sequence data also revealed that there were several SAMS isoforms in the soybean genome.

Example 3

S-Adenosylmethionine Synthetase is Encoded by a Gene Family

Southern hybridization analysis of soybean genomic DNA with a full length SAMS cDNA (SEQ ID NO:1) as a probe suggested that there are at least four related SAMS genes in the soybean genome (FIG. 1A). The DNA probe for Southern hybridization was prepared as follows: plasmid DNA was prepared from an overnight bacteria culture in LB broth (GIBCO BRL, Gaithersburg, Md.) using QIAprep™ miniprep kit (Qiagen, Valencia, Calif.); cDNA inserts encoding SAMS were excised by restriction enzyme digestion and recovered from agarose gel following electrophoretic separation using QIAquick™ gel extraction kit (Qiagen). The 1518 bp SAMS cDNA fragment (SEQ ID NO:1) was labeled with digoxigenin-dUTP as a probe by random primed DNA labeling (Boehringer Mannheim). Twenty micrograms of soybean geneomic DNA was digested with different restriction enzymes and the resulted fragments were resolved on a 0.7% agarose gel. The DNA gel was depurinated in 0.25 M HCl, denatured in 0.5 M NaOH/1.5 M NaCl, neutralized in 1 m Tris-Cl, pH 8.0/1.5 M NaCl, and transferred in 20×SSC (GIBCO BRL) to nylon membrane (Boehringer Mannheim). The Southern blot was hybridized with the SAMS cDNA-specific probe at 45° C. overnight in Easy Hyb (Roche Diagnostics Corp.). The blot was washed 10 minutes in 2×SSC/0.1% SDS, and 3×10 minutes in 0.1×SSC/0.1% SDS at 65° C. The hybridized probe was detected with chemiluminescent reagent CDP-Star (Boehringer Mannheim) according to the manufacturer's protocol. Multiple bands were detected in BamHI, EcoRI, and HindIII digestions (FIG. 1A). The large band in KpnI and SacI digestions may represent more than one DNA fragment because the band is too big for good resolution. The hybridization patterns presented in FIG. 1A and the analysis of partial SAMS cDNA sequences from DuPont's EST database suggest that there are at least four copies of the SAMS gene in the soybean genome and that their sequences are conserved.

The 1314 bp SAMS promoter fragment (SEQ ID NO:6) was labeled with digoxigenin-dUTP also by random primed DNA labeling (Boehringer Mannheim). The labeled SAMS promoter probe was used to hybridize the same Southern blot as above described. The SAMS promoter-specific probe hybridized to a single band in each of the five different digestions, BamHI, EcoRI, HindIII, KpnI, and SacI (FIG. 1B). The results indicate that the SAMS promoter has only a single copy in soybean genome.

A northern hybridization experiment indicated that SAMS gene transcripts were present in a variety of soybean tissues and that the abundance of SAMS gene transcripts did not differ greatly from tissue to tissue. Total RNAs were extracted from soybean leaves, stems, young seeds, medium seeds, old seeds, and pod coats using Trizol™ Reagent according to the manufacturer's protocol (GIBCO BRL). Ten micrograms of total RNA were loaded in each well of a 1.2% agarose gel containing 7% formaldehyde in 1× MOPS buffer, 20 mM 3-[N-morpholino]propane-sulfonic acid, 5 mM sodium acetate, 1 mM EDTA, pH 6.0. RNA was transferred to nylon filters (Micron Separations Inc., Westborough, Mass.) in 10×SSC and crosslinked to the filters with UV light. Filters were hybridized with probes prepared from cDNA insert fragments in 50% deionized formamide, 5×SSPE, 1×Denhardt's solution, 0.1% SDS, and 100 µg denatured salmon sperm DNA (Sigma, St. Louis, Mo.) at 42° for 24 hours. Filters were washed in 2×SSPE and 0.1% SDS at room temperature for 10 minutes, 1×SSPE and 0.1% SDS at 65° for 10 minutes, and then in 0.1×SSPE and 0.1% SDS at 65° for 10 minutes. Filters were exposed to Kodak X-ray film at −80. The abundance of SAMS transcripts in leaves, roots, stems, young seeds, medium seeds, old seeds, and pod coats can be seen in FIG. 9. The weak signals observed in the hybridizations to RNA samples from root and young seed were attributed to underloading, because hybridizations with ribosomal RNAs that serve as internal controls were also relatively weak in those samples (data not shown). Because of the high sequence similarities among the four SAMS gene isoforms, this RNA gel blot was not able to indicate how the isoforms were distributed in any particular tissue. However, the experiment demonstrated that all examined soybean tissues contained SAMS messenger RNA.

Example 4

Cloning of the Soybean S-Adenosylmethionine Synthetase Gene Promoter

The soybean full length SAMS cDNA (SEQ ID NO:1), obtained in Example 2, was used to generate a probe to isolate a SAMS promoter. The full length SAMS cDNA sequence consisted of 1518 bp, and it had a 73 bp 5'-untranslated region and a PstI site at position 296. Because the cDNA clone was harbored in a pBluescript™ SK vector having a PstI site upstream of the EcoRI cloning site, digestion of the clone with Pst1 generated a 315 bp fragment of DNA. The resulting restriction fragment contained 19 bp of vector and cloning linker adapter sequence in addition to the 296 bp of SAMS cDNA sequence. This PstI fragment was labeled with α-$^{32}$P-dCTP, as described in Example 3, and used as a probe to screen a soybean genomic DNA library that had been constructed in a EMBL3 SP6/T7 vector (ClonTech, Palo Alto, Calif.). The library was plated with LE392 (ClonTech) cells at 50,000 plaque forming units (pfu) per 150 mm NZCYM agar plate (GIBCO BRL). Plaques were transferred to Hybond nylon membranes, and the plaque replicas were then denatured and neutralized according to the manufacturer (Amersham Life Science, Arlington Heights, Ill.). The phage DNA was fixed on the membranes by UV-crosslinking (Stratagene). After prehybridization at 65° for 1 hour in 0.5 M NaHPO$_4$, pH 7.2, 1 mM EDTA, 1% crystalline BSA (Sigma), and 7% SDS, the SAMS 315 bp Pst1 fragment probe was denatured in boiling water bath for 5 minutes and added to the same hybridization solution, and was hybridized at 65° for 24 hours. The membranes were washed in 40 mM NaHPO$_4$, pH 7.2, 1 mM EDTA, 0.5% crystalline BSA, and 5% SDS for 10 minutes at room temperature, and then 3×10 minutes at 65° in 40 mM NaHPO$_4$, pH 7.2, 1 mM EDTA, and 1% SDS. The membranes were exposed to Kodak X-ray film (Sigma) at −80°. Positive SAMS genomic DNA phage clones were suspended in SM buffer, 50 mM Tris-Cl, pH 7.5, 100 mM NaCl, 0.2% MgSO$_4$.7H$_2$O, and 0.1% gelatin, and purified by a secondary screening following the same procedure. Twenty three strongly hybridizing plaques were identified by the first screening from a total of 3×10$^5$ pfu, and fifteen were later purified. DNAs were prepared from two of the purified phage clones (Ausubel et al., (1990) pp. 1.13.4-1.13.8), they were digested with BamHI, ClaI, PstI, and NcoI and prepared for a Southern blot. The blot was hybridized with the SAMS 315 bp PstI fragment probe prepared and used as above. A single positive fragment of clone 1 was identified from the ClaI digestion. Since the ClaI restriction site in the cDNA clone is 843 bp from the 5' end of the full length cDNA, the 2.5 kb ClaI fragment was expected to include about 1.7 kb of DNA upstream of the coding sequence, which was considered sufficient to contain the SAMS promoter.

The 2.5 kb ClaI genomic DNA fragment was cloned into pBluescript™ KS and the DNA insert was sequenced. The 3' end sequence of the genomic DNA fragment was expected to match the 5' end sequence of SAMS cDNA from the 5' end to the ClaI site at position 843. However, comparison of the genomic DNA sequence and the cDNA sequence revealed that the two sequences have 192 bp of overlapping sequence starting at position 56 and ending at position 247 of the cDNA sequence (SEQ ID NO:1). The sequence of the 2.5 kb genomic DNA clone downstream of the 192 bp overlapping region was determined to be derived from the cloning vector, lambda EMBL3 SP6/T7, which contributed 257 bp of sequence to the 3' end of the 2.5 kb SAMS ClaI fragment including the ClaI cloning site. Therefore, the soybean derived DNA in the 2.5 kb ClaI fragment is described by the 2336 bp DNA sequence shown in SEQ ID NO:2.

The DNA sequence of the genomic DNA in the 192 bp region (from nucleotide 2145 to the end of the sequence) was very similar to, but did not match perfectly, the cDNA sequence; there were six base pair mismatches in this region. This was not surprising, because it was known from the experiments described in Example 3 that there is a small family of SAMS genes in soybean. It was concluded that this genomic clone is not derived from the same gene from which the cDNA used as the probe was transcribed. It was also noted that the 53 bp at the 5' end of the cDNA did not show any similarity to the genomic sequence upstream of the 191 bp overlapping region (FIG. 2).

A BLASTN search of the DuPont soybean EST database using the nucleotide sequence from the soybean SAMS genomic DNA upstream of the 192 bp region revealed many cDNA clones that matched a 60 bp region of the genomic DNA from nucleotide 1496 to 1555. The sequence of one such cDNA, designated srr1c.pk002.b21, is shown in SEQ ID NO:3.

The cDNA sequence in SEQ ID NO:3 perfectly matches the genomic sequence in SEQ ID NO:2 from nucleotide 1 to 59 of the cDNA. There follows a region of 591 nucleotides in the genomic DNA that is absent from the cDNA. Then the region from nucleotide 60 to 249 of the cDNA perfectly matches the 190 bp region at the 3' end of the genomic DNA. This indicates the presence of a 591 nucleotide intron in the genomic DNA in the 5' transcribed, but untranslated, region of the SAMS gene. The presence of consensus 5' and 3' splice junctions in the genomic DNA at the exon-intron junctions supports this conclusion. Thus, the 53 bp at the 5' end of the cDNA used as the probe (SEQ ID NO:1) did not match the genomic sequence because the genomic sequence at that position in the alignment was from the intron. However, the 53 bp at the 5' end of the cDNA of SEQ ID NO:1 is very similar to the 60 nucleotides at the 5' end of the cDNA of SEQ ID NO:3, suggesting that the gene from which SEQ ID NO:1 was transcribed also contains an intron at the analogous position.

A 1305 bp SAMS genomic DNA fragment starting at nucleotide 856 and ending at nucleotide 2160 of SEQ ID NO:2: was amplified by PCR from the 2.5 kb ClaI clone. The promoter fragment was amplified from this fragment using primers sam-5 (SEQ ID NO:4) and sam-6 (SEQ ID NO:5) and Pfu DNA polymerase (Stratagene).

```
CATGCCATGGTTATACTTCAAAAACTGCAC    (SEQ ID NO: 4)

GCTCTAGATCAAACTCACATCCAA          (SEQ ID NO: 5)
```

An XbaI site and an NcoI site were introduced to the 5' end and 3' end, respectively, of the PCR fragment by using these specifically designed primers. The NcoI site includes the ATG start codon of the SAMS coding region. The resulting 1314 bp fragment is shown in SEQ ID NO:6 and includes the SAMS promoter and the translation leader region, which is interrupted by the 591 nucleotide intron. The first three nucleotides of SEQ ID NO:6 originate from the linker DNA. The first nucleotide of the cDNA sequence presented in SEQ ID NO:3 corresponds to nucleotide number 645 in SEQ ID NO:6.

Using PCR amplification procedures and appropriate primers additional SAMS promoter fragments can be produced from the 2336 nucleotide fragment of SEQ ID NO:2. These include, but are not limited to, the three fragments provided in SEQ ID NOs:14, 15 and 16. SEQ ID NO:14 is a 2165 nucleotide sequence of a SAMS promoter DNA fragment which starts at the 5' end of the 2336 nucleotide sequence of SEQ ID NO:2 and ends at the ATG translation start codon of the SAMS protein. The first nucleotide of the cDNA sequence presented in SEQ ID NO:3 corresponds to nucleotide number 1497 in SEQ ID NO:14. SEQ ID NO:15 is a 1574 nucleotide sequence of a SAMS promoter DNA fragment which starts at the 5' end of the 2336 nucleotide sequence of SEQ ID NO:2 and ends at the ATG translation start codon of the SAMS protein, and from which the 591 nucleotide long intron sequence has been removed. SEQ ID NO:16 is a 719 nucleotide sequence of a SAMS promoter DNA fragment which starts at nucleotide 4 of SEQ ID NO:6 and ends at the ATG translation start codon of the SAMS protein, and from which the 591 nucleotide long intron sequence has been removed.

Example 5

Expression of the GUS Gene by the SAMS Promoter in *Arabidopsis*

Figure 3:
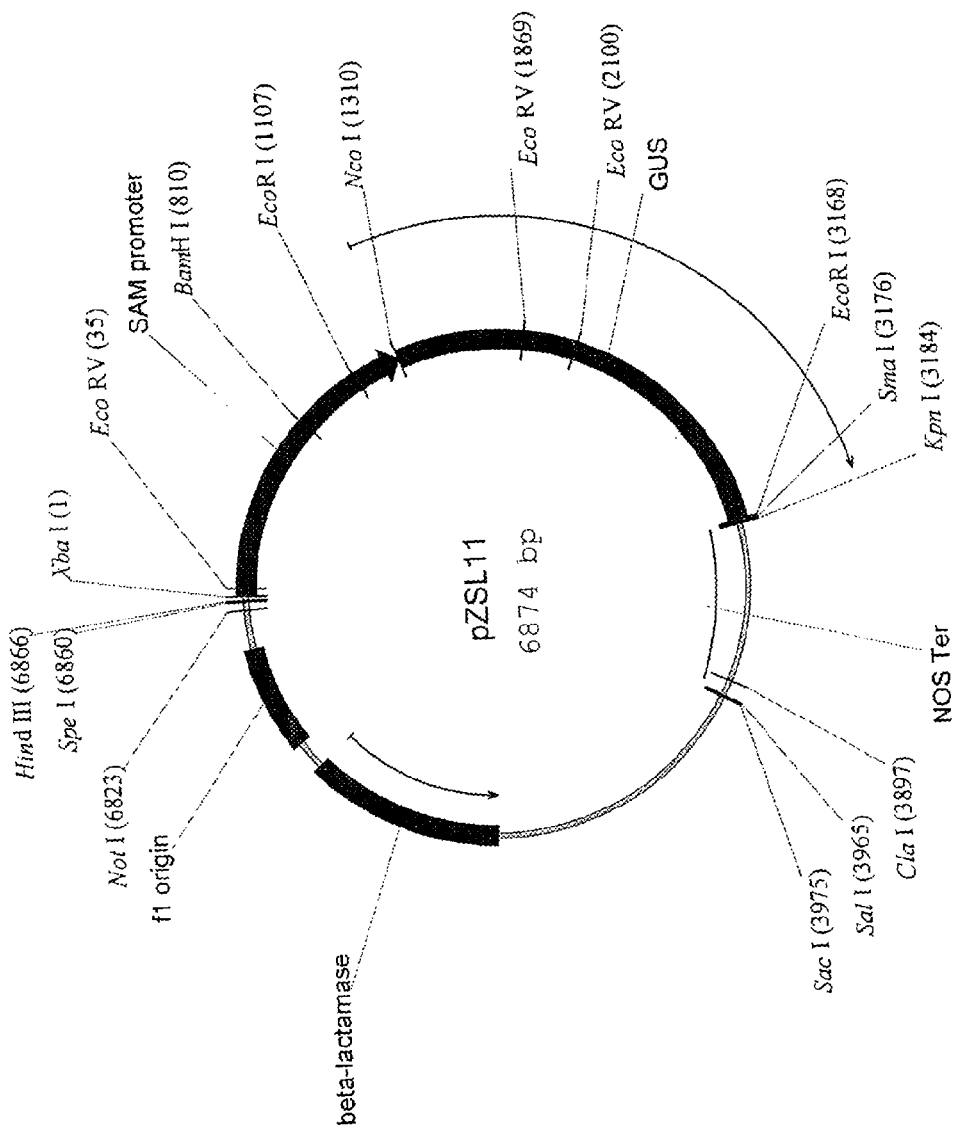

The activity of the soybean SAMS promoter was tested by its ability to express the GUS reporter gene in transgenic *Arabidopsis* plants carrying the SAMS promoter::GUS::3' Nos expression casstette. GUS refers to the *E. coli* β-glucuronidase gene (GUS) (Jefferson, (1987) *Plant Mol. Biol. Rep.* 5:387-405) and 3' Nos refers to the transcription termination region from the nopaline synthase (Nos) gene (Depicker et al. (1982) *J. Mol. Appl. Genet.* 1:561-570). The SAMS promoter fragment (SEQ ID NO:6) was digested with XbaI and NcoI and inserted into plasmid pMH40Δ (SEQ ID NO:17), which contained a 35S promoter::GUS::3' Nos plant expression cassette. The XbaI/NcoI SAMS promoter DNA fragment replaced the 35S promoter of pMH40Δ, to form the pZSL11 plasmid (FIG. 3). The SAMS promoter::GUS::3' Nos DNA fragment (SEQ ID NO:18) was excised from pZSL11 by HindIII and SacI digestion and transferred into the corresponding sites of pBI101 (ClonTech) binary vector. The cloned SAMS promoter was sequenced to verify that no sequence error was generated by the PCR amplification.

The SAMS::GUS expression cassette was introduced into wild type *Arabidopsis thaliana* by *Agrobacteria* mediated transformation. *A. thaliana* ecotype columbia were grown in 228 chamber with continuous light and transformed by vacuum infiltration method using GV3101 *Agrobacteria* (Bent, A. et al., (1994) *Science* 265:1856-1860). Transformed *Arabidopsis* seeds were selected by germination on Murashige and Skoog minimal salt (GIBCO BRL) plus 0.2% phytagel (Sigma), 1% sucrose, and 100 mg/ml kanamycin. The kanamycin resistant seedlings were transferred into soil and grown in 228 chamber under continuous light.

For histochemical GUS staining, plant tissues were incubated in 0.5% 5-bromo-4-chloro-3-indoxyl-β-D-glucuronic acid (X gluc, Biosynth AG, Switzerland) in 50 mM sodium phosphate, pH 7.0, 10 mM EDTA, 0.5 mM potassium ferricyanide, and 0.5 mM potassium ferrocyanide at 378 overnight, and then chlorophyll was removed with 75% ethanol. Pictures were taken using a Nikon dissecting microscope. Strong GUS expression was detected in all the parts of the transgenic *Arabidopsis* plants, including flowers (FIG. 4A), leaves (FIG. 4B), stems (bolt) (FIG. 4C), silique coats and developing seeds (FIG. 4D-F), developing embryos (FIG. 4G), and seedlings (not shown). The GUS staining on leaves and silique coats was uniform with all the veins and mesophyll tissues similarly stained, while staining on flowers and stems was not uniform. Although some seeds were not stained for GUS activity due to genetic segregation, the funiculi that connected these seeds to the silique coat stained positively for GUS activity (FIG. 4G). These results indicated that the soybean SAMS promoter was a constitutive promoter and was able to function in heterologous plant.

The GUS activities of the transgenic *Arabidopsis* plants were further analyzed by a fluorometric assay. For fluorescence analysis, plant tissues were ground in microfuge tubes with extraction buffer, 50 mM phosphate buffer, pH 7.0, 10 mM EDTA, 0.1% Triton X-100, 0.1% N-lauroyl sarcosine, and 10 mM β-mercaptoethanol, to homogeneity. The samples were centrifuged at 14,000 rpm for 10 minutes, and aliquots of the supernatant were used to determine protein concentrations by the Bradford method (Bio-Rad, Hercules, Calif.) using 96 well microtiter plates read with a kinetic microplate reader (Molecular Devices, Sunnyvale, Calif.). The β-glucuronidase activities were analyzed by standard protocol (Jefferson et al, (1987) *EMBO J.* 6:3901-3907) using 96 well microtiter plates read with Cytofluor multiwell plate reader (PerSeptive Biosystems, Framingham, Mass.). Data were entered into a Microsoft Excel spread sheet and analyzed. Triple samples of flower, leaf, stem, silique coat, young seed (white), medium seed (light green), old seed (dark green), and dry seed from six plants were analyzed. The soybean SAMS promoter was active in all the tissues analyzed (FIG. 5). Promoter activity varied among the six lines, as is typically seen among plant transformants. The basic expression patterns were similar among all the lines, and the average SAMS promoter activity was comparable to that of the 35S promoter (Battraw and Hall, (1990) *Plant Mol. Biol.* 15:527-538; Jefferson et al., (1987) *EMBO J.* 6:3901-3907; Atanassova et al., (1998) *Plant Mol. Biol.* 37:275-285; Holtorf et al., (1995) *Plant Mol. Biol.* 29:637-646; Wilmink et al., (1995) *Plant Mol. Biol.* 28:949-955). The SAMS promoter was very active in developing seeds, especially in early and medium stages of development, and the GUS specific activities are in the range of 5-40 pmole 4-Mu (4-methylumbelliferone) per microgram protein per minute, which are comparable to many strong promoters (Atanassova et al., (1998) *Plant Mol. Biol.* 37:275-285; Comai et al., (1990) *Plant Mol. Biol.* 15:373-381; Holtorf et al., (1995) *Plant Mol. Biol.* 29:637-646; Wilmink et al., (1995) *Plant Mol. Biol.* 28:949-955).

Example 6

Expression of GUS Gene by SAMS Promoter in Corn

Figure 6A:
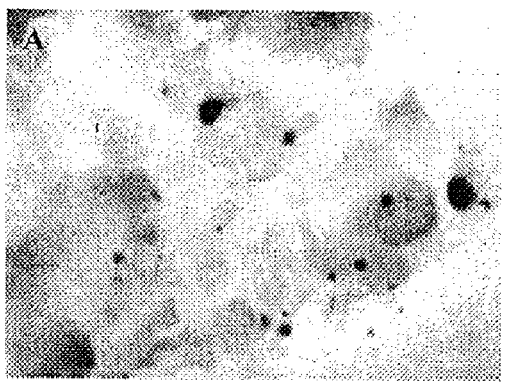
Figure 6B:
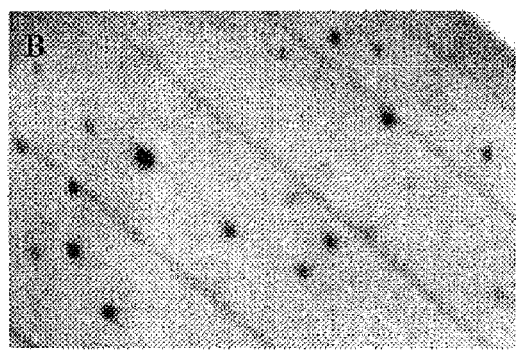
Figure 6C:
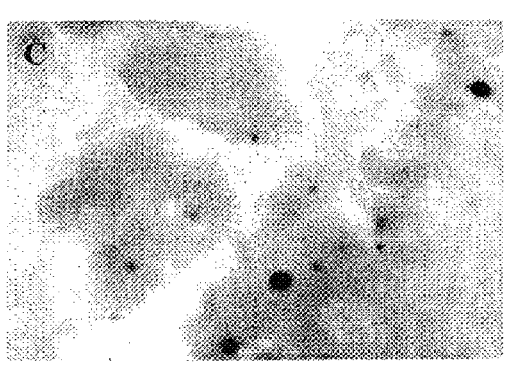
Figure 6D:
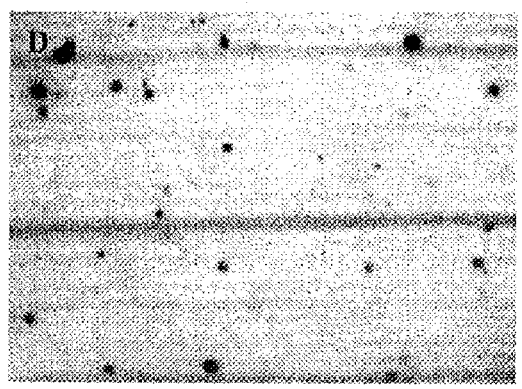

In order to test whether the dicot SAMS promoter also worked in monocot plants, pZSL11 was introduced into corn leaf discs and callus by gene bombardment for transient gene expression assay using the biolistic particle delivery system PDS-1000/He (Bio Rad, Hercules, Calif.). The pMH40Δ plasmid DNA (as set forth in SEQ ID NO:17), which contained the 35S promoter and GUS reporter gene, was also introduced into corn callus and leaf discs by gene bombardment to serve as a positive control vector. After incubation overnight at 37°, bombarded tissues were stained for GUS activity. GUS expression was demonstrated by the blue spots on both the callus (FIG. 6A) and leaf discs (FIG. 6B) bombarded with pZSL11. As expected, the positive control 35S::GUS cassette was also expressed in both callus and leaf discs (FIGS. 6C, D).

Example 7

Expression of Methionine Biosynthesis Genes by SAMS Promoter

The SAMS promoter was fused to two soybean cDNAs, one encoding ATP sulfurylase (ATPS) and a second encoding cystathionine-γ-synthase (CGS1). The soybean ATPS and CGS1 cDNAs were isolated from soybean embryo cDNA libraries using the same procedures as described in Example 1 and Example 2 for isolation of soybean SAMS cDNAs. The coding regions and the 3' untranslated region (UTR) of soybean ATPS and CGS1 genes were inserted into pZSL11 replacing the GUS gene. The resulting SAMS promoter::ATPS and SAMS promoter::CGS1 expression cassettes, SEQ ID NO:19 and SEQ ID NO:20, respectively, were inserted into binary vectors for *Arabidopsis* transformation and transformation was performed as described in Example 5. Transgenic *Arabidopsis* plants with soybean ATPS and CGS1 genes controlled by the SAMS promoter were analyzed by PCR for the presence of the transgenes and by RT-PCR for expression of the transgenes. Genomic DNA used for PCR analysis was prepared from *Arabidopsis* siliques and leaves using 7 M urea, 1.5 M NaCl, 50 mM Tris, pH 8.0, 20 mM EDTA, and 1% N-lauroyl-sarcosine, followed by phenol extraction and ethanol precipitation. Primer sam-9 (SEQ ID NO:7) which is specific to SAMS promoter, and primers specific to the target genes, atps-1 (SEQ ID NO:8) for the ATPS gene and cgs-8 (SEQ ID NO:9) for the CGS1 gene were used in PCR with Taq DNA polymerase (GIBCO BRL) to detect the existence of SAMS::ATPS and SAMS::CGS1 in transgenic *Arabidopsis* plants.

```
TTCGAGTATAGGTCACAATAGG    (SEQ ID NO: 7)

CTTCGCTGAGGACATGGAC       (SEQ ID NO: 8)

GAGTTGTCGCTGTTGTTCGAC     (SEQ ID NO: 9)
```

RNA samples used for RT-PCR were prepared with Trizol™ Reagent (GIBCO BRL). Antisense primers atps-4 (SEQ ID NO:10) and cgs-10 (SEQ ID NO:11) were used in reverse transcription reactions with SuperscriptII™ RT (GIBCO BRL) following the vendor's instruction.

```
AACACAGCATCCGCATTGCG      (SEQ ID NO: 10)

AGGAGTGCAGAATCAGATCAG     (SEQ ID NO: 11)
```

The first strand cDNAs were used in PCR with primer pairs atps-3 (SEQ ID NO:12) and atps-4 (SEQ ID NO:10) for SAMS::ATPS transgenic plants, and cgs-9 (SEQ ID NO:13) and cgs-10 for SAMS::CGS1 transgenic plants. PCR and RT-PCR products were resolved by agarose gel electrophoresis.

```
GCTGATCGAACCAGATGGAG      (SEQ ID NO: 12)

CTGTACAGTTAAACAGTAGTTCT   (SEQ ID NO: 13)
```

Figure 7A:
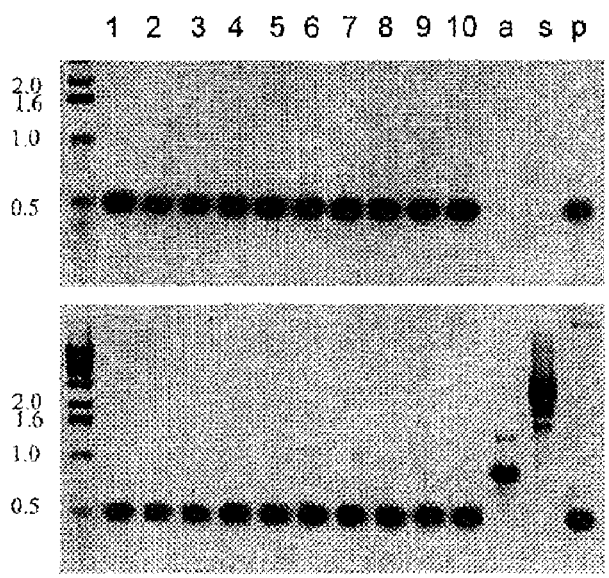
Figure 7B:
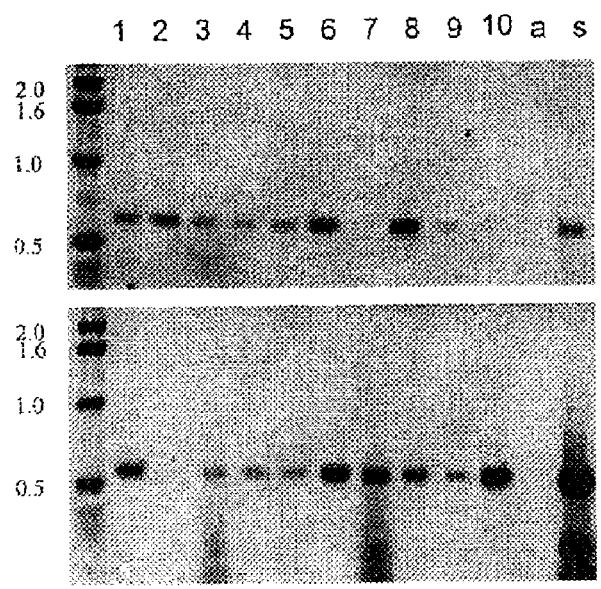

All ten SAMS::CGS1 transgenic *Arabidopsis* harbored the SAM::CGS1 expression cassette as revealed by PCR with SAMS::CGS1-specific primers (FIG. 7A). It was also revealed by the same analysis that all the ten SAMS::ATPS transgenic *Arabidopsis* plants contained the SAMS::ATPS expression cassette (FIG. 7A). RT-PCR analysis detected CGS1 transcripts and ATPS transcripts, respectively, in most of the transgenic plants (FIG. 7B). This shows that the SAMS promoter is capable of driving expression of a variety of different genes in most or all cell types in transformed plants.

Example 8

Induction of SAMS Promoter Activity by Methionine

Since SAMS catalyzes the reaction to synthesize S-adenosyl-L-methionine from methionine and ATP, free methionine levels might regulate SAMS promoter activity. To see if SAMS promoter is regulated by external methionine, the SAMS::GUS transgenic *Arabidopsis* seeds were germinated in the presence of either $H_2O$, 1× Murashige and Skoog salt (GIBCO BRL), 0.01 mM methionine (Sigma), or 1 mM methionine. Ten days old seedlings from ten independent transgenic lines were analyzed for GUS activity according to the protocol described in Example 5. GUS activity for each treatment, in the order given above, for each transgenic line is shown in FIG. 8. All lines responded similarly to the different treatments. Compared to the control of $H_2O$ treamtment, SAMS activity was induced more than two-fold by 0.01 mM free methionine and inhibited about 40% on average by 1× MS salt. The induction effect of SAMS promoter by 1 mM methionine was less than that by 0.01 mM methionine, probably due to a toxic effect of the high methionine concentration; this toxic effect was indicated by the smaller sizes and shorter roots of the seedlings grown in the presence of 1 mM methionine. The toxic effect of high levels of methionine was even more apparent at 10 mM free methionine, since only a few *Arabidopsis* seeds were able to germinate and none survived in the presence of 10 mM free methionine.

Example 9

Expression in Soybean by the SAMS Promoter of the GUS Gene and Two Herbicide-Resistant Acetolactate Synthase Genes Two different soybean SAMS DNA fragments, containing the nucleotides sequences of SEQ ID NO:6 and 14, were shown to have promoter activity in transgenic soybean cells. The plasmid DNA constructs used are described in TABLE 1.

TABLE 1

| Plasmid DNA | SAMS Promoter | Coding Region | Terminator |
|---|---|---|---|
| pZSL11 | 1.3-kb (SEQ ID NO:6) | GUS | NOS |
| pZSL12 | 2.1-kb (SEQ ID NO:14*) | GUS | NOS |
| pZSL13 | 1.3-kb (SEQ ID NO:6) | Soybean ALS** | Soybean ALS |
| pZSL14 | 2.1-kb (SEQ ID NO:14*) | *Arabidopsis* ALS** | *Arabidopsis* ALS |

*Variant of SEQ ID NO:14 with an NcoI site introduced around the start Met.
**Mutant soybean and *Arabidopsis* Acetolactate Synthase (ALS) genes were used, that encode ALS enzymes resistant to herbicidal inhibitors of ALS, such as sulfonylurea herbicides.

Plasmid pZSL11 contains the 1.3-kb SAMS promoter (SEQ ID NO:6) operably linked to the GUS reporter gene (Jefferson (1987) *Plant Mol. Biol. Rep.* 5:387-405), and the NOS terminator (Depicker et al. (1982) *J. Mol. Appl. Genet.* 1:561-570). The construction of pZSL11 is described in Example 5 of the specification. The nucleotide sequence of the {1.3-kb SAMS promoter—GUS—NOS} region corresponds to SEQ ID NO:18.

Plasmid pZSL12 was made by replacing the 5' region of the 1.3-kb SAMS promoter in pZSL11 with a longer SAMS genomic DNA from pZSL10, a plasmid DNA containing an 2335-bp SAMS genomic DNA cloned in pBluescript KS. The 1675-bp XhoI (blunt-ended with *E. coli* DNA polymerase I Klenow fragment)/BamHI fragment from pZSL10 was transferred into pZSL11, to replace the corresponding 809-bp XbaI (blunt end with *E. coli* DNA polymerase I Klenow fragment)/BamHI fragment. The resulting plasmid, pZSL12, has a 2.1-kb SAMS promoter (a variant of SEQ ID NO:14 that contains an NcoI site surrounding the start methionine) which is 869-bp longer than the 1.3-kb SAMS promoter in pZSL11. The nucleotide sequence of the {2.1-kb SAMS promoter—GUS—NOS} region from pZSL12 is shown in SEQ ID NO:21.

Plasmid pZSL13 was made by replacing the GUS gene and NOS terminator in pZSL11 with a DNA fragment containing a soybean mutant ALS coding region and its 3'-UTR (Un-Translated Region). The mutant soybean ALS gene encodes an enzyme that is resistant to inhibitors of ALS, such as sulfonylurea herbicides. The nucleotide sequence of the {1.3-kb SAMS promoter—mutant soy ALS—soy ALS 3'-UTR} region in pZSL13 is shown in SEQ ID NO:22. The corresponding amino acid sequence of the mutant soy ALS protein is shown in SEQ ID NO:23. Plasmid pZSL14 was made by linking the 2.1-kb SAMS promoter from pZSL12 to a DNA fragment containing a mutant *Arabidopsis* ALS gene and its 3'-UTR. The mutant *Arabidopsis* ALS gene encodes an enzyme that is resistant to inhibitors of ALS, such as sulfonylurea herbicides. The nucleotide sequence of the {2.1-kb SAMS promoter mutant *Arabidopsis* ALS *Arabidopsis* ALS 3'-UTR} region in pZSL14 is shown in SEQ ID NO:24. The corresponding amino acid sequence of the mutant *Arabidopsis* ALS protein is shown in SEQ ID NO:25. Mutant plant ALS genes encoding enzymes resistant to sulfonylurea herbicides are described in U.S. Pat. No. 5,013,659 (1991), "Nucleic acid fragment encoding herbicide resistant plant acetolactate synthase". One such mutant is the tobacco SURB-Hra gene, which encodes a herbicide-resistant ALS with the following two mutations in the amino acid sequence of the protein: the proline at position 191, in the conserved "subsequence B", G-Q-V—P (SEQ ID NO:31), has been changed to alanine; and the tryptophan at position 568, in the conserved "subsequence F", G-M-V—V/M-Q-W-E-D-R—F (SEQ ID NO:32), has been changed to leucine (U.S. Pat. No. 5,013,659; Lee et al. (1988) EMBO J 7:1241-1248). The mutant soy ALS gene used in pZSL13 was created by introducing the two Hra-like mutations into the wild-type soybean sequence; the proline at position 183 was changed to alanine, and the tryptophan at position 560 was changed to leucine (SEQ ID NO:23). In addition, during construction of PZSL13, the protein-coding region of the soybean ALS gene was extended at the 5'-end by five artificial codons, resulting in five amino acids, M-P—H—N-T (SEQ ID NO:33), added to the amino-terminus of the ALS protein (SEQ ID NO:23). These extra amino acids are adjacent to, and presumably removed with, the transit peptide during targeting of the mutant soy ALS protein to the plastid. The mutant *Arabidopsis* ALS gene used in pZSL13 was created by introducing the two Hra-like mutations into the wild-type *Arabidopsis* sequence; the proline at position 197 was changed to alanine, and the tryptophan at position 574 was changed to leucine (SEQ ID N 0:25). FIGS. 10A-10C show an amino acid sequence alignment of the following herbicide-sensitive wild-type ALS proteins: a tobacco SURB (ALS II) protein (SEQ ID NO:27; NOBI General Identifier No. 124369); a *Brassica napus* ALS3 (AHAS3) protein (SEQ ID NO:28; NOBI General Identifier No. 320131); an *Arabidopsis thaliana* ALS protein (SEQ ID NO:29; NOBI General Identifier No. 124372); and a soybean ALS protein (SEQ ID NO:30).

Soybean transformation was performed as follows:

Soybean embryogenic suspension cultures were transformed with the GUS-containing plasmids, pZSL11 and pZSL12, by the method of particle gun bombardment using procedures know in the art (Klein et al. (1987) *Nature* (London) 327:70-73; U.S. Pat. No. 4,945,050; Hazel, et al. (1998) *Plant Cell Rep* 17:765-772; Samoylov, et al. (1998) *In Vitro Cell Dev Biol—Plant* 34:8-13). Alternatively, one can use purified DNA restriction fragments containing only the recombinant DNA expression cassette(s) of interest, using 1-15 pg of DNA fragment per base pair of DNA fragment per 30 µl prep. Each such prep is enough to do eight transformation bombardments. The selective agent used was hygromycin (50 mg/mL). In addition, 0.6 µm gold particles were used instead of 1.0 µm particles. Soybean embryogenic suspension cultures were transformed with plasmids pZSL13 and pZSL14, each containing a mutant ALS gene, by a similar procedure with the following modifications.

Stock tissue for these experiments were obtained by initiation of soybean immature seeds. Secondary embryos were excised from explants after 6-8 weeks on media. Secondary embryos were placed on media for 7-9 days under ~80 µEm$^{-}$2s$^{-1}$ light intensity. Tissue was dried on Whatman #2 filter paper then moved to a prebombardment osmotic treatment (media containing 0.25 M mannitol and 0.25 M sorbitol) for 4 hours under ~80 µEm$^{-2}$s$^{-1}$ light intensity. After 4 hours, tissue was moved to an empty 60×15 mm petri dish for bombardment. Approximately 10 mg of tissue (10-15 clumps of 1-2 mm size) were used per plate bombarded.

After bombardment, tissue was moved to media for an overnight incubation at ~80 µEm$^{-2}$s$^{-1}$ light intensity. Tissue was divided in half and placed in liquid media for selection. For selection of transformed cells containing the mutant ALS gene (pZSL13 and pZSL14), the selective agent used was a sulfonylurea (SU) compound with the chemical name, 2-chloro-N-[(4-methoxy-6 methyl-1,3,5-triazine-2-yl)aminocarbonyl]benzenesulfonamide (common names: DPX-W4189 and chlorsulfuron). Chlorsulfuron is the active ingredient in the DuPont sulfonylurea herbicides, GLEAN®. The concentration of SU used was 90 ng/ml. SU was applied one week after bombardment and continued for six weeks, with a fresh media and SU change once a week. After six weeks, events were isolated and kept at 90 ng/ml concentration for another 4-6 weeks. Total time in SU was 8-12 weeks.

After selection, green, transformed tissue was observed growing from untransformed, necrotic embryogenic clusters. Isolated green tissue was removed and inoculated into individual flasks to generate new, clonally propagated, transformed embryogenic suspension cultures. Suspension cultures were subcultured and maintained as clusters of immature embryos and also regenerated into whole plants by maturation and germination of individual somatic embryos.

Figure 11A:
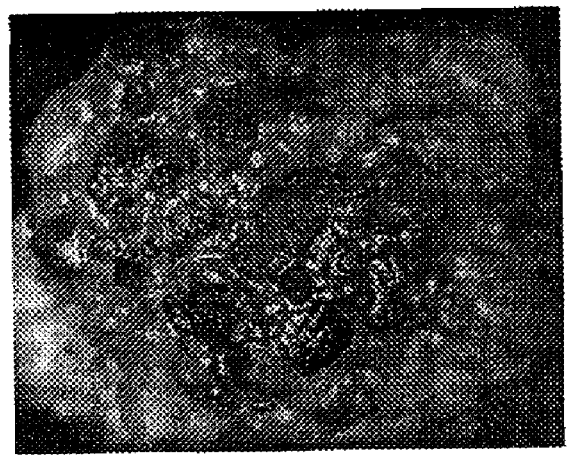
FIG. 11 depicts GUS expression in soybean embryogenic cell lines transformed with pZSL11 or pZSL12.
Figure 11B:
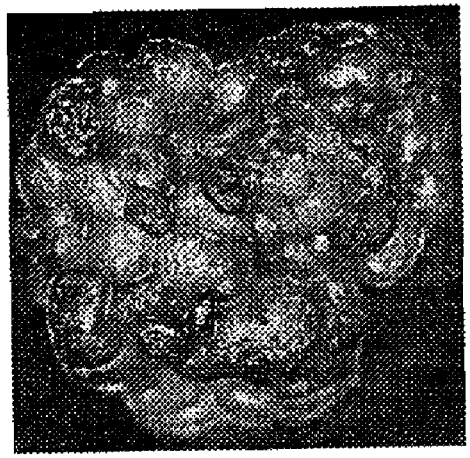

SAMS promoter activity in transgenic soybeans was determined as follows:

Soybean embryogenic suspension cells, transformed with either pZSL11 or pZSL12, were assayed for GUS activity by the histochemical staining procedure described in Example 5. From the results of this assay, it was observed that both the 1.3-kb (SEQ ID NO:6) and the 2.1-kb (SEQ ID NO:14) fragments from the SAMS gene displayed promoter activity (FIG. 11).

Figure 12A:
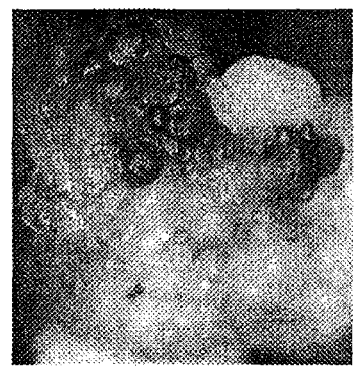
FIG. 12 depicts GUS expression in soybean tissues transformed with pZSL11.
Figure 12B:
Figure 12C:
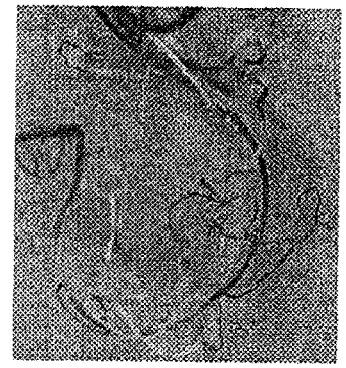

Soybean plants were regenerated from embryogenic suspension cells transformed with either pZSL11 or pZSL12. The results of GUS histochemical staining of pZSL11 transformed soybean tissues (embryogenic suspension cells, leaf, stem and root) are shown in FIG. 12. These results indicate promoter activity for the 1.3-kb (SEQ ID NO:4) fragment of pZSL11 in each of these cell types (FIG. 12). Similar results were obtained for the 2.1-kb (SEQ ID NO:14) fragment of pZSL12.

The 1.3-kb and 2.1-kb SAMS fragments in pZSL13 and pZSL14, respectively, were also used to drive expression of the SU-resistant mutant ALS genes from soybean (pZSL13) and *Arabidopsis* (pZSL14). Transformed soybean cell lines were selected using the SU herbicide, as described above. Transgenic soybean cell lines containing either plasmid DNA were obtained, demonstrating that both SAMS fragments functioned as promoters in embryogenic suspension cells.

Soybean plants, transformed with either pZSL13 or pZSL14, were tested for tolerance to SU herbicide. A spray solution was made containing 60 grams of Thifensulfuron-methyl active ingredient per hectare and 0.25% wt/wt of AL-2999 nonionic surfactant. Thifensulfuron-methyl has the chemical name, methyl 3-[[[[(4-methoxy-6-methyl-1,3,5-triazin-2-yl)amino]carbonyl]amino]sulfonyl]-2-thiophenecarboxylate, and is the active ingredient in the two DuPont sulfonylurea herbicides, HARMONY GT® and PINNACLE®. Either HARMONY GT® or PINNACLE® can be used as the source of this sulfonylurea for the spray test. AL-2999 is a nonionic surfactant, obtainable as ATPLUS UCL 1007® from Uniqema. This mixture was evenly sprayed onto the soybean plants at the 1st or 2nd trifoliate stage of development. After waiting approximately two weeks the results were scored. All wild-type plants (or plants lacking the SAMS:herbicide-resistant ALS transgene) were dead (negative control), all plants from commercially available STS® (Sulfonylurea Tolerant Soybean) seeds were alive (positive control), and plants containing the SAMS:herbicide-resistant ALS transgene from either pZSL13 or pZSL14 also survived. Consequently, either the 1.3-kb (SEQ ID NO:6) or the 2.1-kb (SEQ ID NO:14) fragment from the SAMS gene can drive expression of the mutant ALS gene at levels sufficient to provide tolerance to SU.

Both the 1.3-kb (SEQ ID NO:6) and the 2.1-kb (SEQ ID NO:14) fragments from the SAMS gene functioned as promoters in transgenic soybean. Promoter activity was observed in multiple cell types (embryonic suspension cells, leaf, stem and root). In addition, promoter activity was sufficient to drive functional expression of both a screenable marker (GUS) and a selectable marker (herbicide-resistant ALS) gene.

What is claimed is:

1. A plant, plant cell or plant tissue comprising a recombinant DNA construct comprising a first isolated nucleic acid fragment encoding a polypeptide having acetolactate synthase activity, wherein said polypeptide comprises the amino acid sequence set forth in SEQ ID NO:23 or SEQ ID NO:25, operably linked to a second isolated nucleic acid fragment, having constitutive promoter activity in a plant, wherein said second isolated nucleic acid fragment comprises a nucleotide sequence consisting essentially of the nucleotide sequence set forth in SEQ ID NO:6 or SEQ ID NO:14.

2. The plant of claim wherein said plant is a dicot.

3. The plant of claim 2 where said plant is a dicot selected from the group consisting of *Arabidopsis*, soybean, oilseed *Brassica*, peanut, sunflower, safflower, cotton, tobacco, tomato, potato, and cocoa.

4. The plant of claim 3 wherein said plant is soybean.

5. Seed comprising a recombinant DNA construct comprising a first isolated nucleic acid fragment encoding a polypeptide with acetolactate synthase activity, wherein said polypeptide comprises the amino acid sequence set forth in SEQ ID NO:23 or SEQ ID NO:25, operably linked to a second isolated nucleic acid fragment, having constitutive promoter activity in a plant, wherein said second isolated nucleic acid fragment comprises a nucleotide sequence consisting essentially of the nucleotide sequence set forth in SEQ ID NO:6 or SEQ ID NO:14.

6. Seed of claim 5 wherein said seed is from a dicot.

7. Seed of claim 5 wherein said seed is from a dicot selected from the group consisting of *Arabidopsis*, soybean, oilseed *Brassica*, peanut, sunflower, safflower, cotton, tobacco, tomato, potato, and cocoa.

8. Seed of claim 7 wherein said seed is from soybean.

* * * * *

SEQUENCE LISTING

```
<160> NUMBER OF SEQ ID NOS: 33

<210> SEQ ID NO 1
<211> LENGTH: 1518
<212> TYPE: DNA
<213> ORGANISM: Glycine max

<400> SEQUENCE: 1
agccaagccc cactcaacca ccacaccact ctctctgctc ttcttctacc tttcaagttt      60
ttaaagtatt aagatggcag agacattcct atttacctca gagtcagtga acgagggaca     120
ccctgacaag ctctgcgacc aaatctccga tgctgtcctc gacgcttgcc ttgaacagga     180
cccagacagc aaggttgcct gcgaaacatg caccaagacc aacttggtca tggtcttcgg     240
agagatcacc accaaggcca acgttgacta cgagaagatc gtgcgtgaca cctgcaggaa     300
catcggcttc gtctcaaacg atgtgggact tgatgctgac aactgcaagg tccttgtaaa     360
cattgagcag cagagccctg atattgccca gggtgtgcac ggccaccttc caaaagacc      420 cgaggaaatc ggtgctggag accagggtca catgtttggc tatgccacgg acgaaacccc     480
agaattgatg ccattgagtc atgttcttgc aactaaactc ggtgctcgtc tcaccgaggt     540
tcgcaagaac ggaacctgcc catggttgag gcctgatggg aaaacccaag tgactgttga     600
gtattacaat gacaacggtg ccatggttcc agttcgtgtc cacactgtgc ttatctccac     660
ccaacatgat gagactgtga ccaacgacga aattgcagct gacctcaagg agcatgtgat     720
caagccggtg atcccggaga agtaccttga tgagaagacc attttccact tgaacccctc     780
tggccgtttt gtcattggag gtcctcacgg tgatgctggt ctcaccggcc gcaagatcat     840
catcgatact tacggaggat ggggtgctca tggtggtggt gctttctccg ggaaggatcc     900
caccaaggtt gataggagtg gtgcttacat tgtgagacag gctgctaaga gcattgtggc     960
aagtggacta gccagaaggt gcattgtgca agtgtcttat gccattggtg tgcccgagcc    1020
tttgtctgtc tttgttgaca cctatggcac cgggaagatc catgataagg agattctcaa    1080
```

```
cattgtgaag gagaactttg atttcaggcc cggtatgatc tccatcaacc ttgatctcaa    1140
gaggggtggg aataacaggt tcttgaagac tgctgcatat ggacacttcg gcagagagga    1200
ccctgacttc acatgggaag tggtcaagcc cctcaagtgg gagaaggcct aaggccattc    1260
attccactgc aatgtgctgg gagttttta gcgttgccct ataatgtct attatccata     1320 actttccacg tcccttgctc tgtgttttc tctcgtcgtc ctcctcctat tttgtttctc    1380
ctgcctttca tttgtaattt tttacatgat caactaaaaa atgtactctc tgttttccga    1440
ccattgtgtc tcttaatatc agtatcaaaa agaatgttcc aagttaaaaa aaaaaaaaa    1500 aaaaaaaaaa aaaaaaaa                                                  1518

<210> SEQ ID NO 2
<211> LENGTH: 2336
<212> TYPE: DNA
<213> ORGANISM: Glycine max

<400> SEQUENCE: 2
atcgatagag acatgttatt cacaaaccat aaaatgatgg ctaaaattgg tgtgattgga     60
acgatatctg tttattatga tttcagggcg caaaaatgcg agtacttaat aaaatttttac   120 atttaaatta gaattttttt tatcaataaa tattaattta ttagtttat tagaaatatt     180 aattagaaaa ttttgaatcc ccgatttctc ctccttttct tcgctattca tcattttcta    240
accaaaccaa tcttatatgt tcttcaaatt agaacttgaa attattaatt ataattaaac    300
tgaaaacaat tggtatcaa tcatataca tgcttagtaa taaatgcga taattaattg      360 ataaatctgc aaaagatttt acaaatatct ttcagaaaaa attaataaca aattttgtcg    420
ttttcatggt gttggtctga ggaggatttg gcactataga actctcctac ggaccattct    480
ttgcacttca actaaacgat ggtcagaatt ggtggggatt ttatattcaa gcatatccct    540
ttcaaaactt cctacttact tcgtgcgttc ggtaatcggt aacattagac tttcaaaatc    600 attttttaacc cctaaacagt aaatttgaag acaaaaata atattttttca aatttgatag    660 actattttttt ttttgtaatt tgacgaacca aaaccagatt tatcctgaat tttaggaacc    720
acagatgtaa ctaaaccaat atttatttat tttctaaaac aaaatttcat ggcagcatgc    780
ctcagcccat gaaaaaaacc ttataaaaat atctacacat tgaccattga aaagttcgtt    840
ctcccatggg taaccagatc aaactcacat ccaaacataa catggatatc tccttaccaa    900
tcatactaat tattttgggt taaatattaa tcattatttt taagtatta attaagaaat     960 taaaagatt tttaaaaaaa tgtataaaat tatattattc atgattttttc atacatttga   1020 ttttgataat aaatatattt ttttaattt cttaaaaaat gttgcaagac acttattaga    1080
catagtcttg ttctgtttac aaaagcattc atcatttaat acattaaaaaa atattttaata  1140 ctaacagtag aatcttcttg tgagtggtgt gggagtaggc aacctggcat tgaaacgaga   1200
gaaagagagt cagaaccaga agacaaataa aagtatgca acaaacaaat caaaatcaaa   1260
gggcaaaggc tggggttggc tcaattggtt gctacattca attttcaact cagtcaacgg   1320
ttgagattca ctctgacttc cccaatctaa gccgcggatg caaacggttg aatctaaccc   1380
acaatccaat ctcgttactt aggggctttt ccgtcattaa ctcacccctg ccacccggtt    1440
tccctataaa ttggaactca atgctcccct ctaaactcgt atcgcttcag agttgagacc   1500
aagacacact cgttcatata tctctctgct cttctcttct cttctaccctc tcaaggtact    1560 tttcttctcc ctctaccaaa tcctagattc cgtggttcaa tttcggatct tgcacttctg    1620
gtttgctttg ccttgctttt tcctcaactg ggtccatcta ggatccatgt gaaactctac    1680
```

-continued

```
tctttcttta atatctgcgg aatacgcgtt ggactttcag atctagtcga aatcatttca    1740
taattgcctt tctttctttt agcttatgag aaataaaatc attttttttt atttcaaaat    1800
aaaccttggg ccttgtgctg actgagatgg ggtttggtga ttacagaatt ttagcgaatt    1860
ttgtaattgt acttgtttgt ctgtagtttt gttttgtttt cttgtttctc atacattcct    1920
taggcttcaa ttttattcga gtataggtca aataggaat tcaaactttg agcaggggaa    1980
ttaatccctt ccttcaaatc cagtttgttt gtatatatgt ttaaaaatg aaacttttgc    2040 tttaaattct attataactt tttttatggc aaaaatttt gcatgtgtct ttgctctcct    2100
gttgtaaatt tactgtttag gtactaactc taggcttgtt gtgcagtttt tgaagtataa    2160
agatggcaga gacattccta ttcacctcgg agtcagtgaa cgaggacac cctgataagc    2220 tctgcgacca aatctccgat gctgtcctcg acgcttgcct cgaacaggac ccagacagca    2280
aggttgcctg cgaaacatgc accaagacca acttggtcat ggtcttcgga gagatc       2336
```

<210> SEQ ID NO 3
<211> LENGTH: 522
<212> TYPE: DNA
<213> ORGANISM: Glycine max
<220> FEATURE:
<221> NAME/KEY: unsure
<222> LOCATION: (405)
<223> OTHER INFORMATION: n = a, c, g or t
<220> FEATURE:
<221> NAME/KEY: unsure
<222> LOCATION: (509)
<223> OTHER INFORMATION: n = a, c, g or t
<220> FEATURE:
<221> NAME/KEY: unsure
<222> LOCATION: (515)
<223> OTHER INFORMATION: n = a, c, g or t

<400> SEQUENCE: 3

```
gaccaagaca cactcgttca tatatctctc tgctcttctc ttctcttcta cctctcaagt      60
ttttgaagta taaagatggc agagacattc ctattcacct cggagtcagt gaacgaggga     120
caccctgata agctctgcga ccaaatctcc gatgctgtcc tcgacgcttg cctcgaacag     180
gacccagaca gcaaggttgc ctgcgaaaca tgcaccaaga ccaacttggt catggtcttc     240
ggagagatca ccaccaaggc caacgttgac tacgagaaga tcgtgcgtga cacctgcagg     300
agcatcggct tcatctcaaa cgatgtggga cttgatgctg acaactgcaa ggtccttgta     360
aacattgagc agcagagccc tgatattgcc cagggcgtgc acggncacct taccaaaaga     420
cctgaagaaa ttggcgctgg tgaccaaggt cacatgtttg gctatgccac tgatgaaacc     480
ccaaaattca tgccattgag tcatgttcnt gcaancaagc tc                        522
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 4

```
catgccatgg ttatacttca aaaactgcac                                       30
```

<210> SEQ ID NO 5
<211> LENGTH: 24
<212> TYPE: DNA
<213> ORGANISM: Artificial Sequence
<220> FEATURE:

<223> OTHER INFORMATION: Description of Artificial Sequence: PCR Primer

<400> SEQUENCE: 5
gctctagatc aaactcacat ccaa     24

<210> SEQ ID NO 6
<211> LENGTH: 1314
<212> TYPE: DNA
<213> ORGANISM: Glycine max

<400> SEQUENCE: 6

```
tctagatcaa actcacatcc aaacataaca tggatatctc cttaccaatc atactaatta      60
ttttgggtta atattaatc attattttta agatattaat taagaaatta aaagattttt     120
taaaaaatg tataaaatta tattattcat gattttcat acatttgatt ttgataataa      180
atatattttt tttaatttct taaaaaatgt tgcaagacac ttattagaca tagtcttgtt     240
ctgtttacaa aagcattcat catttaatac attaaaaaat atttaatact aacagtagaa     300
tcttcttgtg agtggtgtgg gagtaggcaa cctggcattg aaacgagaga agagagtca     360
gaaccagaag acaaataaaa agtatgcaac aaacaaatca aatcaaagg gcaaaggctg     420
gggttggctc aattggttgc tacattcaat tttcaactca gtcaacggtt gagattcact     480
ctgacttccc caatctaagc cgcggatgca aacggttgaa tctaacccac aatccaatct     540
cgttacttag gggcttttcc gtcattaact caccccctgcc acccggtttc cctataaatt     600
ggaactcaat gctcccctct aaactcgtat cgcttcagag ttgagaccaa gacacactcg     660
ttcatatatc tctctgctct tctcttctct tctacctctc aaggtacttt tcttctccct     720
ctaccaaatc ctagattccg tggttcaatt tcggatcttg cacttctggt ttgctttgcc     780
ttgcttttc ctcaactggg tccatctagg atccatgtga aactctactc tttctttaat     840
atctgcggaa tacgcgttgg actttcgat ctagtcgaaa tcatttcata attgcctttc     900
tttcttttag cttatgagaa ataaaatcat ttttttttat ttcaaaataa accttgggcc     960
ttgtgctgac tgagatgggg tttggtgatt acagaatttt agcgaatttt gtaattgtac    1020
ttgtttgtct gtagttttgt tttgttttct tgtttctcat acattcctta ggcttcaatt    1080
ttattcgagt ataggtcaca ataggaattc aaactttgag caggggaatt aatcccttcc    1140
ttcaaatcca gtttgtttgt atatatgttt aaaaaatgaa actttgctt taaattctat    1200
tataacttttt tttatggcaa aaattttgc atgtgtcttt gctctcctgt tgtaaattta    1260
ctgtttaggt actaactcta ggcttgttgt gcagttttg aagtataacc atgg           1314
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 7
ttcgagtata ggtcacaata gg     22

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 8

-continued cttcgctgag gacatggac                                                      19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 9
gagttgtcgc tgttgttcga c                                                   21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 10
aacacagcat ccgcattgcg                                                     20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 11
aggagtgcag aatcagatca g                                                   21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 12
gctgatcgaa ccagatggag                                                     20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 13
ctgtacagtt aaacagtagt tct                                                 23

<210> SEQ ID NO 14
<211> LENGTH: 2165
<212> TYPE: DNA
<213> ORGANISM: Glycine max

<400> SEQUENCE: 14
atcgatagag acatgttatt cacaaaccat aaaatgatgg ctaaaattgg tgtgattgga          60
acgatatctg tttattatga tttcagggcg caaaaatgcg agtacttaat aaaattttac        120
atttaaatta gaattttttt tatcaataaa tattaattta ttagttttat tagaaatatt        180
aattagaaaa ttttgaatcc ccgatttctc ctcctttct tcgctattca tcattttcta         240

| | |
|---|---:|
| accaaaccaa tcttatatgt tcttcaaatt agaacttgaa attattaatt ataattaaac | 300 |
| tgaaaacaat ttggtatcaa ttcatataca tgcttagtaa taaaatgcga taattaattg | 360 |
| ataaatctgc aaaagatttt acaaatatct ttcagaaaaa attaataaca aattttgtcg | 420 |
| ttttcatggt gttggtctga ggaggatttg gcactataga actctcctac ggaccattct | 480 |
| ttgcacttca actaaacgat ggtcagaatt ggtggggatt ttatattcaa gcatatccct | 540 |
| ttcaaaactt cctacttact tcgtgcgttc ggtaatcggt aacattagac tttcaaaatc | 600 |
| atttttaacc cctaaacagt aaatttgaag gacaaaaata atattttca aatttgatag | 660 |
| actatttttt ttttgtaatt tgacgaacca aaaccagatt tatcctgaat tttaggaacc | 720 |
| acagatgtaa ctaaaccaat atttatttat tttctaaaac aaaatttcat ggcagcatgc | 780 |
| ctcagcccat gaaaaaaacc ttataaaaat atctacacat tgaccattga aaagttcgtt | 840 |
| ctcccatggg taaccagatc aaactcacat ccaaacataa catggatatc tccttaccaa | 900 |
| tcatactaat tattttgggt taaatattaa tcattatttt taagatatta attaagaaat | 960 |
| taaaagattt tttaaaaaaa tgtataaaat tatattattc atgattttc atacatttga | 1020 |
| ttttgataat aaatatattt tttttaattt cttaaaaaat gttgcaagac acttattaga | 1080 |
| catagtcttg ttctgtttac aaaagcattc atcatttaat acattaaaaa atatttaata | 1140 |
| ctaacagtag aatcttcttg tgagtggtgt gggagtaggc aacctggcat tgaaacgaga | 1200 |
| gaaagagagt cagaaccaga agacaaataa aaagtatgca acaaacaaat caaaatcaaa | 1260 |
| gggcaaaggc tggggttggc tcaattggtt gctacattca attttcaact cagtcaacgg | 1320 |
| ttgagattca ctctgacttc cccaatctaa gccgcggatg caaacggttg aatctaaccc | 1380 |
| acaatccaat ctcgttactt aggggctttt ccgtcattaa ctcacccctg ccacccggtt | 1440 |
| tccctataaa ttggaactca atgctcccct ctaaactcgt atcgcttcag agttgagacc | 1500 |
| aagcacacact cgttcatata tctctctgct cttctcttct cttctacctc tcaaggtact | 1560 |
| tttcttctcc ctctaccaaa tcctagattc cgtggttcaa tttcggatct tgcacttctg | 1620 |
| gtttgctttg ccttgctttt tcctcaactg ggtccatcta ggatccatgt gaaactctac | 1680 |
| tctttcttta atatctgcgg aatacgcgtt ggactttcag atcagtcga aatcatttca | 1740 |
| taattgcctt tctttctttt agcttatgag aaataaaatc attttttttt atttcaaaat | 1800 |
| aaaccttggg ccttgtgctg actgagatgg ggtttggtga ttacagaatt ttagcgaatt | 1860 |
| ttgtaattgt acttgtttgt ctgtagtttt gttttgtttt cttgtttctc atacattcct | 1920 |
| taggcttcaa ttttattcga gtataggtca caataggaat tcaaactttg agcagggaa | 1980 |
| ttaatcccctt ccttcaaatc cagtttgttt gtatatatgt ttaaaaaatg aaacttttgc | 2040 |
| tttaaattct attataactt ttttttatggc aaaaatttt gcatgtgtct ttgctctcct | 2100 |
| gttgtaaatt tactgtttag gtactaactc taggcttgtt gtgcagtttt tgaagtataa | 2160 |
| agatg | 2165 |

<210> SEQ ID NO 15
<211> LENGTH: 1574
<212> TYPE: DNA
<213> ORGANISM: Glycine max

<400> SEQUENCE: 15

| | |
|---|---:|
| atcgatagag acatgttatt cacaaaccat aaaatgatgg ctaaaattgg tgtgattgga | 60 |
| acgatatctg tttattatga tttcagggcg caaaaatgcg agtacttaat aaaatttttac | 120 |
| atttaaatta gaatttttttt tatcaataaa tattaattta ttagttttat tagaaatatt | 180 |

```
aattagaaaa ttttgaatcc ccgatttctc ctcctttct tcgctattca tcattttcta     240
accaaaccaa tcttatatgt tcttcaaatt agaacttgaa attattaatt ataattaaac     300
tgaaaacaat ttggtatcaa ttcatataca tgcttagtaa taaaatgcga taattaattg     360
ataaatctgc aaaagatttt acaaatatct ttcagaaaaa attaataaca aattttgtcg     420
ttttcatggt gttggtctga ggaggatttg gcactataga actctcctac ggaccattct     480
ttgcacttca actaaacgat ggtcagaatt ggtggggatt ttatattcaa gcatatccct     540
ttcaaaactt cctacttact tcgtgcgttc ggtaatcggt aacattagac tttcaaaatc     600
atttttaacc cctaaacagt aaatttgaag acaaaaata atattttttca aatttgatag     660 actatttttt ttttgtaatt tgacgaacca aaaccagatt tatcctgaat tttaggaacc     720
acagatgtaa ctaaaccaat atttatttat tttctaaaac aaaatttcat ggcagcatgc     780
ctcagcccat gaaaaaaacc ttataaaaat atctacacat tgaccattga aaagttcgtt     840
ctcccatggg taaccagatc aaactcacat ccaaacataa catggatatc tccttaccaa     900
tcatactaat tattttgggt taaatattaa tcattttttt taagtatatta attaagaaat     960 taaaagattt tttaaaaaaa tgtataaaat tatattattc atgattttc atacatttga    1020 ttttgataat aaatatattt tttttaattt cttaaaaaat gttgcaagac acttattaga    1080
catagtcttg ttctgtttac aaaagcattc atcatttaat acattaaaaa atatttaata    1140
ctaacagtag aatcttcttg tgagtggtgt gggagtaggc aacctggcat tgaaacgaga    1200
gaaagagagt cagaaccaga agacaaataa aaagtatgca acaaacaaat caaaatcaaa    1260
gggcaaaggc tggggttggc tcaattggtt gctacattca attttcaact cagtcaacgg    1320
ttgagattca ctctgacttc cccaatctaa gccgcggatg caaacggttg aatctaaccc    1380
acaatccaat ctcgttactt aggggctttt ccgtcattaa ctcacccctg ccacccggtt    1440
tccctataaa ttggaactca atgctcccct ctaaactcgt atcgcttcag agttgagacc    1500
aagacacact cgttcatata tctctctgct cttctcttct cttctacctc tcaagttttt    1560
gaagtataaa gatg                                                     1574

<210> SEQ ID NO 16
<211> LENGTH: 719
<212> TYPE: DNA
<213> ORGANISM: Glycine max

<400> SEQUENCE: 16
agatcaaact cacatccaaa cataacatgg atatctcctt accaatcata ctaattattt      60
tgggttaaat attaatcatt ttttttaaga tattaattaa gaaattaaaa gattttttaa     120
aaaaatgtat aaaattatat tattcatgat ttttcataca tttgattttg ataataaata     180
tatttttttt aatttcttaa aaatgttgc aagacactta ttagacatag tcttgttctg     240
tttacaaaag cattcatcat ttaatacatt aaaaatatt taatactaac agtagaatct     300
tcttgtgagt ggtgtgggag taggcaacct ggcattgaaa cgagagaaag agtcagaa     360 ccagaagaca aataaaaagt atgcaacaaa caaatcaaaa tcaaagggca aggctgggg     420 ttggctcaat tggttgctac attcaatttt caactcagtc aacggttgag attcactctg     480
acttccccaa tctaagccgc ggatgcaaac ggttgaatct aacccacaat ccaatctcgt     540
tacttagggg cttttccgtc attaactcac ccctgccacc cggtttccct ataaattgga     600
actcaatgct cccctctaaa ctcgtatcgc ttcagagttg agaccaagac acactcgttc     660
```

-continued

| | |
|---|---|
| atatatctct ctgctcttct cttctcttct acctctcaag tttttgaagt ataaagatg | 719 |

<210> SEQ ID NO 17
<211> LENGTH: 6975
<212> TYPE: DNA
<213> ORGANISM: Artificial Sequence
<220> FEATURE:
<223> OTHER INFORMATION: Description of Artificial Sequence:plasmid
<220> FEATURE:
<221> NAME/KEY: unsure
<222> LOCATION: (3367)
<223> OTHER INFORMATION: n = a, c, g or t

<400> SEQUENCE: 17

| | |
|---|---|
| gaatatgcat cactagtaag ctttgctcta gaggatccaa ttccaatccc acaaaaatct | 60 |
| gagcttaaca gcacagttgc tcctctcaga gcagaatcgg gtattcaaca ccctcatatc | 120 |
| aactactacg ttgtgtataa cggtccacat gccggtatat acgatgactg gggttgtaca | 180 |
| aaggcggcaa caaacggcgt tcccggagtt gcacacaaga aatttgccac tattacagag | 240 |
| gcaagagcag cagctgacgc gtacacaaca agtcagcaaa cagacaggtt gaacttcatc | 300 |
| cccaaaggag aagctcaact caagcccaag agctttgcta aggccctaac aagcccacca | 360 |
| aagcaaaaag cccactggct cacgctagga accaaaaggc ccagcagtga tccagcccca | 420 |
| aaagagatct cctttgcccc ggagattaca atggacgatt tcctctatct ttacgatcta | 480 |
| ggaaggaagt tcgaaggtga aggtgacgac actatgttca ccactgataa tgagaaggtt | 540 |
| agcctcttca atttcagaaa gaatgctgac ccacagatgg ttagagaggc ctacgcagca | 600 |
| ggtctcatca agacgatcta cccgagtaac aatctccagg agatcaaata ccttcccaag | 660 |
| aaggttaaag atgcagtcaa aagattcagg actaattgca tcaagaacac agagaaagac | 720 |
| atatttctca agatcagaag tactattcca gtatggacga ttcaaggctt gcttcataaa | 780 |
| ccaaggcaag taatagagat tggagtctct aaaaaggtag ttcctactga atctaaggcc | 840 |
| atgcatggag tctaagattc aaatcgagga tctaacagaa ctcgccgtga agactggcga | 900 |
| acagttcata cagagtcttt tacgactcaa tgacaagaag aaaatcttcg tcaacatggt | 960 |
| ggagcacgac actctggtct actccaaaaa tgtcaaagat acagtctcag aagaccaaag | 1020 |
| ggctattgag acttttcaac aaaggataat ttcgggaaac ctcctcggat tccattgccc | 1080 |
| agctatctgt cacttcatcg aaaggacagt agaaaaggaa ggtggctcct acaaatgcca | 1140 |
| tcattgcgat aaaggaaagg ctatcattca agatgcctct gccgacagtg gtcccaaaga | 1200 |
| tggaccccca cccacgagga gcatcgtgga aaaagaagac gttccaacca cgtcttcaaa | 1260 |
| gcaagtggat tgatgtgaca tctccactga cgtaagggat gacgcacaat cccactatcc | 1320 |
| ttcgcaagac ccttcctcta tataaggaag ttcatttcat ttggagagga cacgctcgag | 1380 |
| ctcatttctc tattacttca gccataacaa aagaactctt ttctcttctt attaaaccat | 1440 |
| ggtacgtcct gtagaaaccc caacccgtga atcaaaaaaa ctcgacgccc tgtgggcatt | 1500 |
| cagtctggat cgcgaaaact gtggaattga tcagcgttgg tgggaaagcg cgttacaaga | 1560 |
| aagccgggca attgctgtgc caggcagttt taacgatcag ttcgccgatg cagatattcg | 1620 |
| taattatgcg ggcaacgtct ggtatcagcg cgaagtcttt ataccgaaag gttgggcagg | 1680 |
| ccagcgtatc gtgctgcgtt tcgatgcggt cactcattac ggcaaagtgt gggtcaataa | 1740 |
| tcaggaagtg atggagcatc agggcggcta tacgccattt gaagccgatg tcacgccgta | 1800 |
| tgttattgcc gggaaaagtg tacgtatcac cgtttgtgtg aacaacgaac tgaactggca | 1860 |
| gactatcccg ccgggaatgg tgattaccga cgaaaacggc aagaaaaagc agtcttactt | 1920 |

```
ccatgatttc tttaactatg ccggaatcca tcgcagcgta atgctctaca ccacgccgaa    1980
cacctgggtg gacgatatca ccgtggtgac gcatgtcgcg caagactgta accacgcgtc    2040
tgttgactgg caggtggtgg ccaatggtga tgtcagcgtt gaactgcgtg atgcggatca    2100
acaggtggtt gcaactggac aaggcactag cgggactttg caagtggtga atccgcacct    2160
ctggcaaccg ggtgaaggtt atctctatga actgtgcgtc acagccaaaa gccagacaga    2220
gtgtgatatc tacccgcttc gcgtcggcat ccggtcagtg gcagtgaagg ccaacagtt    2280
cctgattaac cacaaaccgt tctactttac tggctttggt cgtcatgaag atgcggactt    2340
acgtggcaaa ggattcgata acgtgctgat ggtgcacgac cacgcattaa tggactggat    2400
tggggccaac tcctaccgta cctcgcatta cccttacgct gaagagatgc tcgactgggc    2460
agatgaacat ggcatcgtgg tgattgatga aactgctgct gtcggcttta acctctcttt    2520
aggcattggt ttcgaagcgg gcaacaagcc gaaagaactg tacagcgaag aggcagtcaa    2580
cggggaaact cagcaagcgc acttacaggc gattaaagag ctgatagcgc gtgacaaaaa    2640
ccacccaagc gtggtgatgt ggagtattgc caacgaaccg gatacccgtc cgcaagtgca    2700
cgggaatatt tcgccactgg cggaagcaac gcgtaaactc gacccgacgc gtccgatcac    2760
ctgcgtcaat gtaatgttct gcgacgctca caccgatacc atcagcgatc tctttgatgt    2820
gctgtgcctg aaccgttatt acggatggta tgtccaaagc ggcgatttgg aaacggcaga    2880
gaaggtactg gaaaaagaac ttctggcctg gcaggagaaa ctgcatcagc cgattatcat    2940
caccgaatac ggcgtggata cgttagccgg gctgcactca atgtacaccg acatgtggag    3000
tgaagagtat cagtgtgcat ggctggatat gtatcaccgc gtctttgatc gcgtcagcgc    3060
cgtcgtcggt gaacaggtat ggaatttcgc cgattttgcg acctcgcaag gcatattgcg    3120
cgttggcggt aacaagaaag ggatcttcac tcgcgaccgc aaaccgaagt cggcggcttt    3180
tctgctgcaa aaacgctgga ctggcatgaa cttcggtgaa aaaccgcagc agggaggcaa    3240
acaatgaatc aacaactctc ctggcgcacc atcgtcggct acagcctcgg tggggaattc    3300
cccgggggta cctaatagtg agatccaaca cttacgtttg caacgtccaa gagcaaatag    3360
accacgnacg ccggaaggtt gccgcagcgt gtggattgcg tctcaattct ctcttgcagg    3420
aatgcaatga tgaatatgat actgactatg aaactttgag ggaatactgc ctagcaccgt    3480
cacctcataa cgtgcatcat gcatgccctg acaacatgga acatcgctat ttttctgaag    3540
aattatgctc gttggaggat gtcgcggcaa ttgcagctat tgccaacatc gaactacccc    3600
tcacgcatgc attcatcaat attattcatg cggggaaagg caagattaat ccaactggca    3660
aatcatccag cgtgattggt aacttcagtt ccagcgactt gattcgtttt ggtgctaccc    3720
acgtttttcaa taaggacgag atggtggagt aaagaaggag tgcgtcgaag cagatcgttc    3780
aaacatttgg caataaagtt tcttaagatt gaatcctgtt gccggtcttg cgatgattat    3840
catataattt ctgttgaatt acgttaagca tgtaataatt aacatgtaat gcatgacgtt    3900
atttatgaga tgggttttta tgattagagt cccgcaatta tacatttaat acgcgataga    3960
aaacaaaata tagcgcgcaa actaggataa attatcgcgc gcggtgtcat ctatgttact    4020
agatcgatca aacttcggta ctgtgtaatg acgatgagca atcgagaggc tgactaacaa    4080
aaggtacatc ggtcgacgag ctccctatag tgagtcgtat tagaggccga cttggccaaa    4140
ttcgtaatca tggtcatagc tgtttcctgt gtgaaattgt tatccgctca caattccaca    4200
caacatacga gccggaagca taaagtgtaa agcctggggt gcctaatgag tgagctaact    4260
```

```
cacattaatt gcgttgcgct cactgcccgc tttccagtcg ggaaacctgt cgtgccagct    4320
gcattaatga atcggccaac gcgcggggag aggcggtttg cgtattgggc gctcttccgc    4380
ttcctcgctc actgactcgc tgcgctcggt cgttcggctg cggcgagcgg tatcagctca    4440
ctcaaaggcg gtaatacggt tatccacaga atcaggggat aacgcaggaa agaacatgtg    4500
agcaaaaggc cagcaaaagg ccaggaaccg taaaaaggcc gcgttgctgg cgttttccca    4560
taggctccgc cccctgacg agcatcacaa aaatcgacgc tcaagtcaga ggtggcgaaa    4620
cccgacagga ctataaagat accaggcgtt tccccctgga agctccctcg tgcgctctcc    4680
tgttccgacc ctgccgctta ccggatacct gtccgccttt ctcccttcgg gaagcgtggc    4740
gctttctcat agctcacgct gtaggtatct cagttcggtg taggtcgttc gctccaagct    4800
gggctgtgtg cacgaacccc ccgttcagcc cgaccgctgc gccttatccg gtaactatcg    4860
tcttgagtcc aacccggtaa gacacgactt atcgccactg gcagcagcca ctggtaacag    4920
gattagcaga gcgaggtatg taggcggtgc tacagagttc ttgaagtggt ggcctaacta    4980
cggctacact agaaggacag tatttggtat ctgcgctctg ctgaagccag ttaccttcgg    5040
aaaaagagtt ggtagctctt gatccggcaa acaaaccacc gctggtagcg gtggtttttt    5100
tgtttgcaag cagcagatta cgcgcagaaa aaaaggatct caagaagatc ctttgatctt    5160
ttctacgggg tctgacgctc agtggaacga aaactcacgt taagggattt tggtcatgag    5220
attatcaaaa aggatcttca cctagatcct tttaaattaa aaatgaagtt ttaaatcaat    5280
ctaaagtata tatgagtaaa cttggtctga cagttaccaa tgcttaatca gtgaggcacc    5340
tatctcagcg atctgtctat ttcgttcatc catagttgcc tgactccccg tcgtgtagat    5400
aactacgata cgggagggct taccatctgg ccccagtgct gcaatgatac cgcgagaccc    5460
acgctcaccg gctccagatt tatcagcaat aaaccagcca gccggaaggg ccgagcgcag    5520
aagtggtcct gcaactttat ccgcctccat ccagtctatt aattgttgcc gggaagctag    5580
agtaagtagt tcgccagtta atagtttgcg caacgttgtt gccattgcta caggcatcgt    5640
ggtgtcacgc tcgtcgtttg gtatggcttc attcagctcc ggttcccaac gatcaaggcg    5700
agttacatga tcccccatgt tgtgcaaaaa agcggttagc tccttcggtc ctccgatcgt    5760
tgtcagaagt aagttggccg cagtgttatc actcatggtt atggcagcac tgcataattc    5820
tcttactgtc atgccatccg taagatgctt ttctgtgact ggtgagtact caaccaagtc    5880
attctgagaa tagtgtatgc ggcgaccgag ttgctcttgc ccggcgtcaa tacgggataa    5940
taccgcgcca catagcagaa ctttaaaagt gctcatcatt ggaaaacgtt cttcggggcg    6000
aaaactctca aggatcttac cgctgttgag atccagttcg atgtaaccca ctcgtgcacc    6060
caactgatct tcagcatctt ttactttcac cagcgtttct gggtgagcaa aaacaggaag    6120
gcaaaatgcc gcaaaaaagg gaataagggc gacacggaaa tgttgaatac tcatactctt    6180 ccttttcaa tattattgaa gcatttatca gggttattgt ctcatgagcg gatacatatt    6240
tgaatgtatt tagaaaaata aacaaatagg ggttccgcgc acatttcccc gaaaagtgcc    6300
acctgacgcg ccctgtagcg gcgcattaag cgcggcgggt gtggtggtta cgcgcagcgt    6360
gaccgctaca cttgccagcg ccctagcgcc cgctcctttc gctttcttcc cttcctttct    6420
cgccacgttc gccggctttc cccgtcaagc tctaaatcgg gcatcccctt tagggttccg    6480
atttagtgct ttacggcacc tcgaccccaa aaaacttgat tagggtgatg gttcacgtag    6540
tgggccatcg ccctgataga cggttttcg cccttttgacg ttggagtcca cgttctttaa    6600
tagtggactc ttgttccaaa ctggaacaac actcaaccct atctcggtct attcttttga    6660
```

-continued

```
tttataaggg attttgccga tttcggccta ttggttaaaa aatgagctga tttaacaaaa    6720
atttaacgcg aattttaaca aaatattaac aaaatattaa cgtttacaat ttcccattcg    6780
ccattcaggc tgcgcaactg ttgggaaggg cgatcggtgc gggcctcttc gctattacgc    6840
cagctggcga aaggggatg tgctgcaagg cgattaagtt gggtaacgcc agggttttcc     6900
cagtcacgac gttgtaaaac gacggccagt gccaagctga cttggtcagc ggccgcagat    6960
ttaggtgaca ctata                                                     6975
```

<210> SEQ ID NO 18
<211> LENGTH: 3985
<212> TYPE: DNA
<213> ORGANISM: Artificial Sequence
<220> FEATURE:
<223> OTHER INFORMATION: Description of Artificial Sequence:chimeric
      gene
<220> FEATURE:
<221> NAME/KEY: unsure
<222> LOCATION: (3249)
<223> OTHER INFORMATION: n = a, c, g or t

<400> SEQUENCE: 18

```
aagctttgct ctagatcaaa ctcacatcca aacataacat ggatatcttc cttaccaatc      60
atactaatta ttttgggtta aatattaatc attattttta agatattaat taagaaatta     120
aaagattttt taaaaaatg tataaaaatta tattattcat gattttcat acatttgatt     180 ttgataataa atatattttt tttaatttct taaaaaatgt tgcaagacac ttattagaca     240
tagtcttgtt ctgtttacaa aagcattcat catttaatac attaaaaaat atttaatact     300
aacagtagaa tcttcttgtg agtggtgtgg gagtaggcaa cctggcattg aaacgagaga     360
aagagagtca gaaccagaag acaaataaaa agtatgcaac aaacaaatca aaatcaaagg     420
gcaaaggctg gggttggctc aattggttgc tacattcaat tttcaactca gtcaacggtt     480
gagattcact ctgacttccc caatctaagc cgcggatgca aacggttgaa tctaacccac     540
aatccaatct cgttacttag gggcttttcc gtcattaact caccccctgcc acccggtttc     600 cctataaatt ggaactcaat gctcccctct aaactcgtat cgcttcagag ttgagaccaa     660
gacacactcg ttcatatatc tctctgctct tctcttctct tctacctctc aaggtacttt     720
tcttctccct ctaccaaatc ctagattccg tggttcaatt tcggatcttg cacttctggt     780
ttgctttgcc ttgctttttc ctcaactggg tccatctagg atccatgtga aactctactc     840
tttctttaat atctgcggaa tacgcgttgg actttcagat ctagtcgaaa tcatttcata     900
attgcctttc tttctttag cttatgagaa ataaaatcac ttttttttta tttcaaaata     960
aaccttgggc cttgtgctga ctgagatggg gttttggtgat tacagaattt tagcgaattt    1020
tgtaattgta cttgtttgtc tgtagttttg ttttgttttc ttgtttctca tacattcctt    1080
aggcttcaat tttattcgag tataggtcac aataggaatt caaactttga gcaggggaat    1140
taatcccttc cttcaaatcc agtttgtttg tatatatgtt taaaaaatga aacttttgct    1200
ttaaattcta ttataacttt tttatggct gaaattttg catgtgtctt tgctctctgt    1260
tgtaaattta ctgtttaggt actaactcta ggcttgttgt gcagtttttg aagtataacc    1320
atggtacgtc ctgtagaaac cccaacccgt gaaatcaaaa aactcgacgg cctgtgggca    1380
ttcagtctgg atcgcgaaaa ctgtggaatt gatcagcgtt ggtgggaaag cgcgttacaa    1440
gaaagccggg caattgctgt gccaggcagt tttaacgatc agttcgccga tgcagatatt    1500
cgtaattatg cgggcaacgt ctggtatcag cgcgaagtct ttataccgaa aggttgggca    1560
```

```
ggccagcgta tcgtgctgcg tttcgatgcg gtcactcatt acggcaaagt gtgggtcaat    1620
aatcaggaag tgatggagca tcagggcggc tatacgccat ttgaagccga tgtcacgccg    1680
tatgttattg ccgggaaaag tgtacgtatc accgtttgtg tgaacaacga actgaactgg    1740
cagactatcc cgccgggaat ggtgattacc gacgaaaacg gcaagaaaaa gcagtcttac    1800
ttccatgatt tctttaacta tgccggaatc catcgcagcg taatgctcta caccacgccg    1860
aacacctggg tggacgatat caccgtggtg acgcatgtcg cgcaagactg taaccacgcg    1920
tctgttgact ggcaggtggt ggccaatggt gatgtcagcg ttgaactgcg tgatgcggat    1980
caacaggtgg ttgcaactgg acaaggcact agcgggactt gcaagtggt gaatccgcac     2040 ctctggcaac cgggtgaagg ttatctctat gaactgtgcg tcacagccaa agccagaca     2100 gagtgtgata tctacccgct tcgcgtcggc atccggtcag tggcagtgaa gggccaacag    2160
ttcctgatta ccacaaaccc gttctacttt actggctttg gtcgtcatga agatgcggac    2220
ttacgtggca aaggattcga taacgtgctg atggtgcacg accacgcatt aatggactgg    2280
attggggcca actcctaccg tacctcgcat tacccttacg ctgaagagat gctcgactgg    2340
gcagatgaac atggcatcgt ggtgattgat gaaactgctg ctgtcggctt taacctctct    2400
ttaggcattg gtttcgaagc gggcaacaag ccgaaagaac tgtacagcga agaggcagtc    2460 aacgggaaa ctcagcaagc gcacttacag gcgattaaag agctgatagc gcgtgacaaa     2520
aaccacccaa gcgtggtgat gtggagtatt gccaacgaac cggatacccg tccgcaagtg    2580
cacgggaata tttcgccact ggcggaagca acgcgtaaac tcgacccgac gcgtccgatc    2640
acctgcgtca atgtaatgtt ctgcgacgct cacaccgata ccatcagcga tctctttgat    2700
gtgctgtgcc tgaaccgtta ttacggatgg tatgtccaaa gcggcgattt ggaaacggca    2760
gagaaggtac tggaaaaaga acttctggcc tggcaggaga aactgcatca gccgattatc    2820
atcaccgaat acgcgtgga tacgttagcc gggctgcact caatgtacac cgacatgtgg     2880
agtgaagagt atcagtgtgc atggctggat atgtatcacc gcgtctttga tcgcgtcagc    2940
gccgtcgtcg gtgaacaggt atggaatttc gccgattttg cgacctcgca aggcatattg    3000
cgcgttggcg gtaacaagaa agggatcttc actcgcgacc gcaaaccgaa gtcggcggct    3060
tttctgctgc aaaaacgctg gactggcatg aacttcggtg aaaaaccgca gcagggaggc    3120
aaacaatgaa tcaacaactc tcctggcgca ccatcgtcgg ctacagcctc ggtggggaat    3180
tccccggggg tacctaatag tgagatccaa cacttacgtt tgcaacgtcc aagagcaaat    3240
agaccacgna cgccggaagg ttgccgcagc gtgtggattg cgtctcaatt ctctcttgca    3300
ggaatgcaat gatgaatatg atactgacta tgaaactttg agggaatact gcctagcacc    3360
gtcacctcat aacgtgcatc atgcatgccc tgacaacatg gaacatcgct atttttctga    3420
agaattatgc tcgttggagg atgtcgcggc aattgcagct attgccaaca tcgaactacc    3480
cctcacgcat gcattcatca atattattca tgcggggaaa ggcaagatta atccaactgg    3540
caaatcatcc agcgtgattg gtaacttcag ttccagcgac ttgattcgtt ttggtgctac    3600
ccacgttttc aataaggacg agatggtgga gtaaagaagg agtgcgtcga agcagatcgt    3660
tcaaacattt ggcaataaag tttcttaaga ttgaatcctg ttgccggtct tgcgatgatt    3720
atcatataat ttctgttgaa ttacgttaag catgtaataa ttaacatgta atgcatgacg    3780
ttatttatga gatgggtttt tatgattaga gtcccgcaat tatacattta atacgcgata    3840
gaaaacaaaa tatagcgcgc aaactaggat aaattatcgc gcgcggtgtc atctatgtta    3900
```

-continued

```
ctagatcgat caaacttcgg tactgtgtaa tgacgatgag caatcgagag gctgactaac    3960
aaaaggtaca tcggtcgacg agctc                                         3985

<210> SEQ ID NO 19
<211> LENGTH: 3684
<212> TYPE: DNA
<213> ORGANISM: Artificial Sequence
<220> FEATURE:
<223> OTHER INFORMATION: Description of Artificial Sequence:chimeric
      gene
<220> FEATURE:
<221> NAME/KEY: unsure
<222> LOCATION: (2948)
<223> OTHER INFORMATION: n = a, c, g or t

<400> SEQUENCE: 19
aagctttgct ctagatcaaa ctcacatcca aacataacat ggatatcttc cttaccaatc      60
atactaatta ttttgggtta aatattaatc attatttta agatattaat taagaaatta     120
aaagattttt taaaaaatg tataaaatta tattattcat gattttcat acatttgatt      180 ttgataataa atatatttt tttaatttct taaaaaatgt tgcaagacac ttattagaca     240
tagtcttgtt ctgtttacaa aagcattcat catttaatac attaaaaat atttaatact    300 aacagtagaa tcttcttgtg agtggtgtgg gagtaggcaa cctggcattg aaacgagaga    360
aagagagtca gaaccagaag acaaataaaa agtatgcaac aaacaaatca aaatcaaagg    420
gcaaaggctg gggttggctc aattggttgc tacattcaat tttcaactca gtcaacggtt    480
gagattcact ctgacttccc caatctaagc cgcggatgca aacggttgaa tctaacccac    540
aatccaatct cgttacttag gggcttttcc gtcattaact caccctgcc acccggtttc    600 cctataaatt ggaactcaat gctccctct aaactcgtat cgcttcagag ttgagaccaa    660
gacacactcg ttcatatatc tctctgctct tctcttctct tctacctctc aaggtacttt    720
tcttctccct ctaccaaatc ctagattccg tggttcaatt tcggatcttg cacttctggt    780
ttgctttgcc ttgcttttc ctcaactggg tccatctagg atccatgtga aactctactc    840 tttcttaat atctgcggaa tacgcgttgg actttcagat ctagtcgaaa tcatttcata    900
attgcctttc tttcttttag cttatgagaa ataaaatcac ttttttta tttcaaaata    960 aaccttgggc cttgtgctga ctgagatggg gtttggtgat tacagaattt tagcgaattt   1020
tgtaattgta cttgtttgtc tgtagttttg ttttgttttc ttgtttctca tacattcctt   1080
aggcttcaat tttattcgag tataggtcac aataggaatt caaactttga gcaggggaat   1140
taatcccttc cttcaaatcc agtttgtttg tatatatgtt taaaaaatga aacttttgct   1200
ttaaattcta ttataacttt ttttatggct gaaattttg catgtgtctt tgctctctgt   1260
tgtaaattta ctgtttaggt actaactcta ggcttgttgt gcagttttg aagtataacc   1320 atggccactt tcttcgccca aacctccttc ccctcccact ctctctccaa aaccttcgat   1380
acccatttcg cccctgcccc gaaagtcaac gtctttgtga acttcagggc gaggaggcac   1440
gttggggtgc gagtttcgaa cgcgctgatc gaaccagatg gagggaagct cgtggagctt   1500
gtggtgacgg attttgagag ggatttgaag aagggtgagg ctctttcgtt gccgaggatc   1560
aagctctcaa ggattgacct tgagtgggtc catgtcctca gcgaaggatg gccacaccc   1620 ctgaaaggct tcatgagaga agccgagttc ctccaaacgc ttcatttcaa ctcgctccga   1680
ctcgatgatg ggtcggtcgt gaacatgtca gtgcccatcg tgctggctat tgatgatgcg   1740
cagaagcatc ggatcgggga taacaaaaag gttgctcttt tgattccaa gggagacccc   1800
```

-continued

```
gttgcaattc tcaataatat tgagatttat aagcatccta aagaagaaag aatagcccga    1860
acttggggaa ccattgcccc tggcctacct tatgttgaac aaactataac caatgctgga    1920
aattggttga ttgggggtga cctagaggtc attgaaccaa ttcagtacaa tgatggactt    1980
gatcattttc gtctatctcc ggcacaactc cgtgcagagt tcacaaggcg caatgcggat    2040
gctgtgtttg ccttccagct ccggaatcct gttcacaatg ccatgctttt gctaatgact    2100
gacacccgaa agcgccttct tgagatgggc tataagaatc ctgtcctctt gcttcatcca    2160
cttggaggct acaccaaagc tgatgatgtc ccacttgatt ggcgaatgaa gcaacatgag    2220
aaggtacttg aggatggtgt tcttgatcca gagacaactg tggtatccat attcccatct    2280
cccatgcact atgctggacc cacggaggtg cagtggcatg caaaggctag gatcaatgca    2340
ggggctaact tctatatcgt tggtcgtgac cccgcaggca tgagccatcc agttgagaaa    2400
agagatctgt atgatgctga ccatggaaag aaagtattga gcatggcacc gggactagag    2460
cgtctaaaca ttcttccttt cagggttgct gcatatgaca agactcaggg taaaatggca    2520
ttctttgacc cttcaaggcc tcaggacttc ctgttcatat caggcacaaa gatgcgcaca    2580
ctggcaagga acaaagaaag tcctcctgat ggatttatgt gccctggtgg atggaaggtg    2640
ctggttgatt actatgatag cttagtactc tcaagcaacg gcaaagtgca ggaagctgtt    2700
ccagcttaat cttgtatcat atcataatgt atatatctca tgattgggag aaaccttaag    2760
cttatgtatt ctcctgctaa gacatacttc acgaggatcc tctggcccaa tctaataata    2820
ataataaatt aaaactttgg ggaggcaaaa aaaaaaaaaa aaaaaaaaaa aactcgaggg    2880
ggggcccggt acctaatagt gagatccaac acttacgttt gcaacgtcca agagcaaata    2940
gaccacgnac gccggaaggt tgccgcagcg tgtggattgc gtctcaattc tctcttgcag    3000
gaatgcaatg atgaatatga tactgactat gaaactttga gggaatactg cctagcaccg    3060
tcacctcata acgtgcatca tgcatgccct gacaacatgg aacatcgcta tttttctgaa    3120
gaattatgct cgttggagga tgtcgcggca attgcagcta ttgccaacat cgaactaccc    3180
ctcacgcatg cattcatcaa tattattcat gcggggaaag gcaagattaa tccaactggc    3240
aaatcatcca gcgtgattgg taacttcagt tccagcgact tgattcgttt tggtgctacc    3300
cacgttttca ataaggacga gatggtggag taaagaagga gtgcgtcgaa gcagatcgtt    3360
caaacatttg gcaataaagt ttcttaagat tgaatcctgt tgccggtctt gcgatgatta    3420
tcatataatt tctgttgaat tacgttaagc atgtaataat taacatgtaa tgcatgacgt    3480
tatttatgag atgggttttt atgattagag tcccgcaatt atacatttaa tacgcgatag    3540
aaaacaaaat atagcgcgca aactaggata aattatcgcg cgcggtgtca tctatgttac    3600
tagatcgatc aaacttcggt actgtgtaat gacgatgagc aatcgagagg ctgactaaca    3660
aaaggtacat cggtcgacga gctc                                           3684
```

<210> SEQ ID NO 20
<211> LENGTH: 3963
<212> TYPE: DNA
<213> ORGANISM: Artificial Sequence
<220> FEATURE:
<223> OTHER INFORMATION: Description of Artificial Sequence:chimeric gene
<220> FEATURE:
<221> NAME/KEY: unsure
<222> LOCATION: (3227)
<223> OTHER INFORMATION: n = a, c, g or t

<400> SEQUENCE: 20

```
aagctttgct ctagatcaaa ctcacatcca aacataacat ggatatcttc cttaccaatc    60
atactaatta ttttgggtta aatattaatc attattttta agatattaat taagaaatta   120
aaagattttt taaaaaaatg tataaaatta tattattcat gattttttcat acatttgatt   180 ttgataataa atatatttt tttaatttct taaaaaatgt tgcaagacac ttattagaca    240
tagtcttgtt ctgtttacaa aagcattcat catttaatac attaaaaaat atttaatact   300
aacagtagaa tcttcttgtg agtggtgtgg gagtaggcaa cctggcattg aaacgagaga   360
aagagagtca gaaccagaag acaaataaaa agtatgcaac aaacaaatca aaatcaaagg   420
gcaaaggctg gggttggctc aattggttgc tacattcaat tttcaactca gtcaacggtt   480
gagattcact ctgacttccc caatctaagc cgcggatgca aacggttgaa tctaacccac   540
aatccaatct cgttacttag gggcttttcc gtcattaact caccccctgcc acccggtttc   600 cctataaatt ggaactcaat gctccctct aaactcgtat cgcttcagag ttgagaccaa   660
gacacactcg ttcatatatc tctctgctct tctcttctct tctacctctc aaggtacttt   720
tcttctccct ctaccaaatc ctagattccg tggttcaatt tcggatcttg cacttctggt   780
ttgctttgcc ttgctttttc ctcaactggg tccatctagg atccatgtga aactctactc   840
tttctttaat atctgcggaa tacgcgttgg actttcagat ctagtcgaaa tcatttcata   900
attgcctttc tttcttttag cttatgagaa ataaatcac ttttttttta tttcaaaata   960
aaccttgggc cttgtgctga ctgagatggg gtttggtgat tacagaattt tagcgaattt  1020
tgtaattgta cttgtttgtc tgtagttttg ttttgttttc ttgtttctca tacattcctt  1080
aggcttcaat tttattcgag tataggtcac aataggaatt caaactttga gcaggggaat  1140
taatcccttc cttcaaatcc agtttgtttg tatatatgtt taaaaaatga aacttttgct  1200
ttaaattcta ttataacttt ttttatggct gaaattttg catgtgtctt tgctctctgt   1260
tgtaaattta ctgtttaggt actaactcta ggcttgttgt gcagttttg aagtataacc   1320 atggccgttt cgagctcgca catgcgtttc acctttgagt gccgctccga tcccgatttc  1380 tcgcccccc cgccgtcctt cgacaacctc cgccgccgaa acttccgctc ctccgcagga   1440
tccggcgcgg cgtttcacgg catctcctcc ctcatcctcc gcttccctcc caacttccag   1500
cgccagctaa gcaccaaggc gcgccgcaac tgcagcaaca tcggcgtcgc gcaaatcgtc   1560
gccgcttcgt ggtcgaacaa cagcgacaac tctccggccg ccggggctcc ggcgccgccc   1620
gcggccaccg ccacggacgc cgctacggtg cctctcccg tcgtcgtcgc cgccaacgag   1680
gacgtcgttg tctccgccgc ggcagacgag aacggggctg tacagttaaa cagtagttct   1740
tattcttcat ttttgaaatc cgatgcaagc aaaacgattc atgccgctga aagactgggt   1800
aggggtattg agactgatgg aattaccacc ctgtgttta acacttctgc ctacttttt    1860 aagaaaaccg ctgatctcat tgatttcaag gagaatcgtc aagtgagtta tgaatacggg   1920
cgctatggaa acccaacgac ggtggttctg gaggagaaga taagtgcatt ggaggggcc    1980 gaatcaactg tgataatggc gtctgggatg tgtgctagcg tagtcctgtt tatggcactg   2040
gttccagctg gtggacatct tgtgaccact acgattgtt ataggaagac tagaatattc   2100
attgagactt ttcttccaaa gatggggatc acgaccactg taattgatcc agcagatgtt   2160
ggagccttgg aatctgcatt ggagcagcac aatgtgtctc tattcttcac tgagtctcct   2220
accaatccat tcctgagatg tgttgatatt aagctggttt cagagctttg ccacaagaag   2280
gggactttgc tctgtattga tggtacattt gcaactccat tgaaccagaa ggcccttgcc   2340
cttggcgctg atctgattct gcactcctta acaaaataca tgggtggaca tcatgatgtc   2400
```

-continued

```
cttggtggtt gcataagtgg ttcaattaag gtggtttcgc aaattcggac tttgcaccat  2460
gttttgggtg gtacacttaa cccgaatgct gcatacctat tcatcagagg catgaaaacg  2520
ctgcatctcc gtgtacagca gcagaattca acaggaatga ggatggccaa acttttagag  2580
gcacatccca aggtgaagcg ggtctactat ccaggcttgc cgagtcaccc tgaacatgag  2640
cttgccaaga ggcagatgac tggtttcggt ggtgttgtca gttttgagat tgatggagat  2700
ctacatacca caataaaatt tattgattca ttgaaaatcc catatattgc ggcctcgttt  2760
ggtggctgtg agagcattgt ggatcaacct gctattttgt cttactggga tcttcctcag  2820
tcagaaaggg ccaagtacaa gatttatgac aacctggttc gcttcagctt tggagttgaa  2880
gattttgagg atttgaaggc tgatgtcctg caagctctgg aagctatata gacagttttc  2940
ctgattcacc caagtttttt tcttttataa ttgtgctatt tgtttgttat cacatctggc  3000
gattcaattg aattttgatc gtctaatgtt ctgttggaat tgtgttaaga tgaatggtct  3060
ctaatttgga tgttatgaaa cttgtgatga attgttgaaa ttgaaacctc tatttgatga  3120
aaaaaaaaaa aaaaaaaaaa aaaaaaaaaa actcgagggg gggcccggta cctaatagtg  3180
agatccaaca cttacgtttg caacgtccaa gagcaaatag accacgnacg ccggaaggtt  3240
gccgcagcgt gtggattgcg tctcaattct ctcttgcagg aatgcaatga tgaatatgat  3300
actgactatg aaactttgag ggaatactgc ctagcaccgt cacctcataa cgtgcatcat  3360
gcatgccctg acaacatgga acatcgctat ttttctgaag aattatgctc gttggaggat  3420
gtcgcggcaa ttgcagctat tgccaacatc gaactacccc tcacgcatgc attcatcaat  3480
attattcatg cggggaaagg caagattaat ccaactggca atcatccag cgtgattggt  3540 aacttcagtt ccagcgactt gattcgtttt ggtgctaccc acgttttcaa taaggacgag  3600
atggtggagt aaagaaggag tgcgtcgaag cagatcgttc aaacatttgg caataaagtt  3660
tcttaagatt gaatcctgtt gccggtcttg cgatgattat catataattt ctgttgaatt  3720
acgttaagca tgtaataatt aacatgtaat gcatgacgtt atttatgaga tgggttttta  3780
tgattagagt cccgcaatta tacatttaat acgcgataga aaacaaaata tagcgcgcaa  3840
actaggataa attatcgcgc gcggtgtcat ctatgttact agatcgatca aacttcggta  3900
ctgtgtaatg acgatgagca atcgagaggc tgactaacaa aaggtacatc ggtcgacgag  3960
ctc                                                              3963
```

<210> SEQ ID NO 21
<211> LENGTH: 4827
<212> TYPE: DNA
<213> ORGANISM: Artificial Sequence
<220> FEATURE:
<223> OTHER INFORMATION: Description of Artificial Sequence: chimeric gene
<220> FEATURE:
<221> NAME/KEY: unsure
<222> LOCATION: (459)
<223> OTHER INFORMATION: n = a, c, g or t
<220> FEATURE:
<221> NAME/KEY: unsure
<222> LOCATION: (461)
<223> OTHER INFORMATION: n = a, c, g or t
<220> FEATURE:
<221> NAME/KEY: unsure
<222> LOCATION: (660)
<223> OTHER INFORMATION: n = a, c, g or t
<220> FEATURE:
<221> NAME/KEY: unsure
<222> LOCATION: (729)
<223> OTHER INFORMATION: n = a, c, g or t

```
<220> FEATURE:
<221> NAME/KEY: unsure
<222> LOCATION: (4091)
<223> OTHER INFORMATION: n = a, c, g or t

<400> SEQUENCE: 21
atcgatagag acatgttatt cacaaaccat aaaatgatgg ctaaaattgg tgtgattgga      60
acgatatctg tttattatga tttcagggcg caaaaatgcg agtacttaat aaaattttac     120
atttaaatta gaattttttt tatcaataaa tattaattta ttagttttat tagaaatatt     180
aattagaaaa ttttgaatcc ccgatttctc ctccttttct tcgctattca tcattttcta     240
accaaaccaa tcttatatgt tcttcaaatt agaacttgaa attattaatt ataattaaac     300
tgaaaacaat ttggtatcaa ttcatataca tgcttagtaa taaatgcga taattaattg     360 ataaatctgc aaaagatttt acaaatatct ttcagaaaaa attaataaca aattttgtcg     420
ttttcatggt gttggtctga ggaggatttg gcactatana nctctcctac ggaccattct     480
ttgcacttca actaaacgat ggtcagaatt ggtggggatt ttatattcaa gcatatccct     540
ttcaaaactt cctacttact tcgtgcgttc ggtaatcggt aacattagac tttcaaaatc     600 attttttaacc cctaaacagt aaatttgaag acaaaaata atattttttca aatttgatan    660 actatttttt ttttgtaatt tgacgaacca aaaccagatt tatcctgaat tttaggaacc     720
acagatgtna ctaaaccaat atttatttat tttctaaaac aaaatttcat ggcagcatgc     780
ctcagcccat gaaaaaaacc ttataaaaat atctacacat tgaccattga aaagttcgtt     840
ctcccatggg taaccagatc aaactcacat ccaaacataa catggatatc tccttaccaa     900
tcatactaat tattttgggt taaatattaa tcattatttt taagtatatta attaagaaat     960 taaaagattt tttaaaaaaa tgtataaaat tatattattc atgattttttc atacatttga   1020 ttttgataat aaatatattt tttttaattt cttaaaaaat gttgcaagac acttattaga    1080
catagtcttg ttctgtttac aaaagcattc atcatttaat acattaaaaa atatttaata    1140
ctaacagtag aatcttcttg tgagtggtgt gggagtaggc aacctggcat tgaaacgaga    1200
gaaagagagt cagaaccaga agacaaataa aaagtatgca acaaacaaat caaaatcaaa    1260
gggcaaaggc tggggttggc tcaattggtt gctacattca attttcaact cagtcaacgg    1320
ttgagattca ctctgacttc cccaatctaa gccgcggatg caaacggttg aatctaaccc    1380
acaatccaat ctcgttactt aggggctttt ccgtcattaa ctcacccctg ccacccggtt    1440
tccctataaa ttggaactca atgctcccct ctaaactcgt atcgcttcag agttgagacc    1500
aagacacact cgttcatata tctctctgct cttctcttct cttctacctc tcaaggtact    1560
tttcttctcc ctctaccaaa tcctagattc cgtggttcaa tttcggatct tgcacttctg    1620
gtttgctttg ccttgctttt tcctcaactg ggtccatcta ggatccatgt gaaactctac    1680 tcttcttta atatctgcgg aatacgcgtt ggactttcag atctagtcga aatcatttca    1740
taattgcctt tctttctttt agcttatgag aaataaaatc acttttttttt tatttcaaaa    1800 taaaccttgg gccttgtgct gactgagatg gggtttggtg attacagaat tttagcgaat    1860
tttgtaattg tacttgtttg tctgtagttt tgttttgttt tcttgtttct catacattcc    1920
ttaggcttca attttattcg agtataggtc acaataggaa ttcaaacttt gagcagggga    1980
attaatccct tccttcaaat ccagtttgtt tgtatatatg tttaaaaaat gaaacttttg    2040
ctttaaattc tattataact ttttttatgg ctgaaatttt tgcatgtgtc tttgctctct    2100
gttgtaaatt tactgtttag gtactaactc taggcttgtt gtgcagtttt tgaagtataa    2160
```

```
ccatggtacg tcctgtagaa accccaaccc gtgaaatcaa aaaactcgac ggcctgtggg   2220
cattcagtct ggatcgcgaa aactgtggaa ttgatcagcg ttggtgggaa agcgcgttac   2280
aagaaagccg ggcaattgct gtgccaggca gttttaacga tcagttcgcc gatgcagata   2340
ttcgtaatta tgcgggcaac gtctggtatc agcgcgaagt ctttataccg aaaggttggg   2400
caggccagcg tatcgtgctg cgtttcgatg cggtcactca ttacggcaaa gtgtgggtca   2460
ataatcagga agtgatggag catcagggcg gctatacgcc atttgaagcc gatgtcacgc   2520
cgtatgttat tgccgggaaa agtgtacgta tcaccgtttg tgtgaacaac gaactgaact   2580
ggcagactat cccgccggga atggtgatta ccgacgaaaa cggcaagaaa aagcagtctt   2640
acttccatga tttctttaac tatgccggaa tccatcgcag cgtaatgctc tacaccacgc   2700
cgaacacctg ggtggacgat atcaccgtgg tgacgcatgt cgcgcaagac tgtaaccacg   2760
cgtctgttga ctggcaggtg gtggccaatg gtgatgtcag cgttgaactg cgtgatgcgg   2820
atcaacaggt ggttgcaact ggacaaggca ctagcgggac tttgcaagtg gtgaatccgc   2880
acctctggca accgggtgaa ggttatctct atgaactgtg cgtcacagcc aaaagccaga   2940
cagagtgtga tatctacccg cttcgcgtcg gcatccggtc agtggcagtg aagggccaac   3000
agttcctgat taaccacaaa ccgttctact ttactggctt tggtcgtcat gaagatgcgg   3060
acttacgtgg caaaggattc gataacgtgc tgatggtgca cgaccacgca ttaatggact   3120
ggattggggc caactcctac cgtacctcgc attaccctta cgctgaagag atgctcgact   3180
gggcagatga acatggcatc gtggtgattg atgaaactgc tgctgtcggc tttaacctct   3240
ctttaggcat tggtttcgaa gcgggcaaca agccgaaaga actgtacagc gaagaggcag   3300
tcaacgggga aactcagcaa gcgcacttac aggcgattaa agagctgata gcgcgtgaca   3360
aaaaccaccc aagcgtggtg atgtggagta ttgccaacga accggatacc cgtccgcaag   3420
tgcacgggaa tatttcgcca ctggcggaag caacgcgtaa actcgacccg acgcgtccga   3480
tcacctgcgt caatgtaatg ttctgcgacg ctcacaccga taccatcagc gatctctttg   3540
atgtgctgtg cctgaaccgt tattacggat ggtatgtcca aagcggcgat ttggaaacgg   3600
cagagaaggt actggaaaaa gaacttctgg cctggcagga gaaactgcat cagccgatta   3660
tcatcaccga atacggcgtg gatacgttag ccgggctgca ctcaatgtac accgacatgt   3720
ggagtgaaga gtatcagtgt gcatggctgg atatgtatca ccgcgtcttt gatcgcgtca   3780
gcgccgtcgt cggtgaacag gtatggaatt tcgccgattt tgcgacctcg caaggcatat   3840
tgcgcgttgg cggtaacaag aaagggatct tcactcgcga ccgcaaaccg aagtcggcgg   3900
cttttctgct gcaaaaacgc tggactggca tgaacttcgg tgaaaaaccg cagcagggag   3960
gcaaacaatg aatcaacaac tctcctggcg caccatcgtc ggctacagcc tcggtgggga   4020
attccccggg ggtacctaat agtgagatcc aacacttacg tttgcaacgt ccaagagcaa   4080
atagaccacg nacgccggaa ggttgccgca gcgtgtggat tgcgtctcaa ttctctcttg   4140
caggaatgca atgatgaata tgatactgac tatgaaactt gagggaata ctgcctagca   4200 ccgtcacctc ataacgtgca tcatgcatgc cctgacaaca tggaacatcg ctattttctt   4260
gaagaattat gctcgttgga ggatgtcgcg gcaattgcag ctattgccaa catcgaacta   4320
cccctcacgc atgcattcat caatattatt catgcgggga aaggcaagat taatccaact   4380
ggcaaatcat ccagcgtgat tggtaacttc agttccagcg acttgattcg ttttggtgct   4440
acccacgttt tcaataagga cgagatggtg gagtaaagaa ggagtgcgtc gaagcagatc   4500
gttcaaacat ttggcaataa agtttcttaa gattgaatcc tgttgccggt cttgcgatga   4560
```

-continued

```
ttatcatata atttctgttg aattacgtta agcatgtaat aattaacatg taatgcatga    4620
cgttatttat gagatgggtt tttatgatta gagtcccgca attatacatt taatacgcga    4680
tagaaaacaa aatatagcgc gcaaactagg ataaattatc gcgcgcggtg tcatctatgt    4740
tactagatcg atcaaacttc ggtactgtgt aatgacgatg agcaatcgag aggctgacta    4800
acaaaaggta catcggtcga cgagctc                                         4827
```

<210> SEQ ID NO 22
<211> LENGTH: 3939
<212> TYPE: DNA
<213> ORGANISM: Artificial Sequence
<220> FEATURE:
<223> OTHER INFORMATION: Description of Artificial Sequence: chimeric gene
<220> FEATURE:
<221> NAME/KEY: CDS
<222> LOCATION: (1312)..(3279)
<223> OTHER INFORMATION: herbicide-resistant soybean ALS coding region

<400> SEQUENCE: 22

```
tctagatcaa actcacatcc aaacataaca tggatatctt ccttaccaat catactaatt      60
attttgggtt aaatattaat cattattttt aagatattaa ttaagaaatt aaaagatttt     120
ttaaaaaaat gtataaaatt atattattca tgattttca tacatttgat tttgataata     180
aatatatttt ttttaatttc ttaaaaaatg ttgcaagaca cttattagac atagtcttgt     240
tctgtttaca aaagcattca tcatttaata cattaaaaaa tatttaatac taacagtaga     300
atcttcttgt gagtggtgtg ggagtaggca acctggcatt gaaacgagag aaagagagtc     360
agaaccagaa gacaaataaa aagtatgcaa caaacaaatc aaaatcaaag ggcaaaggct     420
ggggttggct caattggttg ctacattcaa ttttcaactc agtcaacggt tgagattcac     480
tctgacttcc ccaatctaag ccgcggatgc aaacggttga atctaaccca caatccaatc     540
tcgttactta ggggcttttc cgtcattaac tcacccctgc cacccggttt ccctataaat     600
tggaactcaa tgctcccctc taaactcgta tcgcttcaga gttgagacca agacacactc     660
gttcatatat ctctctgctc ttctcttctc ttctacctct caaggtactt tcttctccc      720 tctaccaaat cctagattcc gtggttcaat ttcggatctt gcacttctgg tttgctttgc     780
cttgcttttt cctcaactgg gtccatctag gatccatgtg aaactctact ctttctttaa     840
tatctgcgga atacgcgttg gactttcaga tctagtcgaa atcatttcat aattgccttt     900
cttttcttta gcttatgaga aataaaatca cttttttttt atttcaaaat aaaccttggg     960
ccttgtgctg actgagatgg ggtttggtga ttacagaatt ttagcgaatt ttgtaattgt    1020 acttgttgt ctgtagtttt gttttgtttt cttgtttctc atacattcct taggcttcaa    1080
ttttattcga gtataggtca caataggaat tcaaactttg agcaggggaa ttaatccctt   1140
ccttcaaatc cagtttgttt gtatatatgt ttaaaaatg aaacttttgc tttaaattct    1200
attataactt tttttatggc tgaaattttt gcatgtgtct ttgctctctg ttgtaaattt    1260
actgtttagg tactaactct aggcttgttg tgcagttttt gaagtataac c atg cca    1317
                                                          Met Pro
                                                            1 cac aac aca atg gcg gcc acc gct tcc aga acc acc cga ttc tct tct    1365
His Asn Thr Met Ala Ala Thr Ala Ser Arg Thr Thr Arg Phe Ser Ser
        5                  10                  15 tcc tct tca cac ccc acc ttc ccc aaa cgc att act aga tcc acc ctc    1413
Ser Ser Ser His Pro Thr Phe Pro Lys Arg Ile Thr Arg Ser Thr Leu
    20                  25                  30
```

```
cct ctc tct cat caa acc ctc acc aaa ccc aac cac gct ctc aaa atc      1461
Pro Leu Ser His Gln Thr Leu Thr Lys Pro Asn His Ala Leu Lys Ile
 35                  40                  45                  50 aaa tgt tcc atc tcc aaa ccc ccc acg gcg gcg ccc ttc acc aag gaa      1509
Lys Cys Ser Ile Ser Lys Pro Pro Thr Ala Ala Pro Phe Thr Lys Glu
                 55                  60                  65 gcg ccg acc acg gag ccc ttc gtg tca cgg ttc gcc tcc ggc gaa cct      1557
Ala Pro Thr Thr Glu Pro Phe Val Ser Arg Phe Ala Ser Gly Glu Pro
             70                  75                  80 cgc aag ggc gcg gac atc ctt gtg gag gcg ctg gag agg cag ggc gtg      1605
Arg Lys Gly Ala Asp Ile Leu Val Glu Ala Leu Glu Arg Gln Gly Val
         85                  90                  95 acg acg gtg ttc gcg tac ccc ggc ggt gcg tcg atg gag atc cac cag      1653
Thr Thr Val Phe Ala Tyr Pro Gly Gly Ala Ser Met Glu Ile His Gln
    100                 105                 110 gcg ctc acg cgc tcc gcc gcc atc cgc aac gtg ctc ccg cgc cac gag      1701
Ala Leu Thr Arg Ser Ala Ala Ile Arg Asn Val Leu Pro Arg His Glu
115                 120                 125                 130 cag ggc ggc gtc ttc gcc gcc gaa ggc tac gcg cgt tcc tcc ggc ctc      1749
Gln Gly Gly Val Phe Ala Ala Glu Gly Tyr Ala Arg Ser Ser Gly Leu
                135                 140                 145 ccc ggc gtc tgc att gcc acc tcc ggc ccc ggc gcc acc aac ctc gtg      1797
Pro Gly Val Cys Ile Ala Thr Ser Gly Pro Gly Ala Thr Asn Leu Val
            150                 155                 160 agc ggc ctc gcc gac gct tta atg gac agc gtc cca gtc gtc gcc atc      1845
Ser Gly Leu Ala Asp Ala Leu Met Asp Ser Val Pro Val Val Ala Ile
        165                 170                 175 acc ggc cag gtc gcc cgc cgg atg atc ggc acc gac gcc ttc caa gaa      1893
Thr Gly Gln Val Ala Arg Arg Met Ile Gly Thr Asp Ala Phe Gln Glu
    180                 185                 190 acc ccg atc gtg gag gtg agc aga tcc atc acg aag cac aac tac ctc      1941
Thr Pro Ile Val Glu Val Ser Arg Ser Ile Thr Lys His Asn Tyr Leu
195                 200                 205                 210 atc ctc gac gtc gac gac atc ccc cgc gtc gtc gcc gag gct ttc ttc      1989
Ile Leu Asp Val Asp Asp Ile Pro Arg Val Val Ala Glu Ala Phe Phe
                215                 220                 225 gtc gcc acc tcc ggc cgc ccc ggt ccg gtc ctc atc gac att ccc aaa      2037
Val Ala Thr Ser Gly Arg Pro Gly Pro Val Leu Ile Asp Ile Pro Lys
            230                 235                 240 gac gtt cag cag caa ctc gcc gtg cct aat tgg gac gag ccc gtt aac      2085
Asp Val Gln Gln Gln Leu Ala Val Pro Asn Trp Asp Glu Pro Val Asn
        245                 250                 255 ctc ccc ggt tac ctc gcc agg ctg ccc agg ccc ccc gcc gag gcc caa      2133
Leu Pro Gly Tyr Leu Ala Arg Leu Pro Arg Pro Pro Ala Glu Ala Gln
    260                 265                 270 ttg gaa cac att gtc aga ctc atc atg gag gcc caa aag ccc gtt ctc      2181
Leu Glu His Ile Val Arg Leu Ile Met Glu Ala Gln Lys Pro Val Leu
275                 280                 285                 290 tac gtc ggc ggt ggc agt ttg aat tcc agt gct gaa ttg agg cgc ttt      2229
Tyr Val Gly Gly Gly Ser Leu Asn Ser Ser Ala Glu Leu Arg Arg Phe
                295                 300                 305 gtt gaa ctc act ggt att ccc gtt gct agc act tta atg ggt ctt gga      2277
Val Glu Leu Thr Gly Ile Pro Val Ala Ser Thr Leu Met Gly Leu Gly
            310                 315                 320 act ttt cct att ggt gat gaa tat tcc ctt cag atg ctg ggt atg cat      2325
Thr Phe Pro Ile Gly Asp Glu Tyr Ser Leu Gln Met Leu Gly Met His
        325                 330                 335 ggt act gtt tat gct aac tat gct gtt gac aat agt gat ttg ttg ctt      2373
Gly Thr Val Tyr Ala Asn Tyr Ala Val Asp Asn Ser Asp Leu Leu Leu
```

-continued

|  |  |  | | |
|---|---|---|---|---|
| 340 | | 345 | 350 | |
| gcc ttt ggg gta agg ttt gat gac cgt gtt act ggg aag ctt gag gct<br>Ala Phe Gly Val Arg Phe Asp Asp Arg Val Thr Gly Lys Leu Glu Ala<br>355                  360                  365                  370 | | | | 2421 |
| ttt gct agt agg gct aag att gtt cac att gat att gat tct gcc gag<br>Phe Ala Ser Arg Ala Lys Ile Val His Ile Asp Ile Asp Ser Ala Glu<br>375                  380                  385 | | | | 2469 |
| att ggg aag aac aag cag gcg cac gtg tcg gtt tgc gcg gat ttg aag<br>Ile Gly Lys Asn Lys Gln Ala His Val Ser Val Cys Ala Asp Leu Lys<br>              390                  395                  400 | | | | 2517 |
| ttg gcc ttg aag gga att aat atg att ttg gag gag aaa gga gtg gag<br>Leu Ala Leu Lys Gly Ile Asn Met Ile Leu Glu Glu Lys Gly Val Glu<br>              405                  410                  415 | | | | 2565 |
| ggt aag ttt gat ctt gga ggt tgg aga gaa gag att aat gtg cag aaa<br>Gly Lys Phe Asp Leu Gly Gly Trp Arg Glu Glu Ile Asn Val Gln Lys<br>420                    425                  430 | | | | 2613 |
| cac aag ttt cca ttg ggt tac aag aca ttc cag gac gcg att tct ccg<br>His Lys Phe Pro Leu Gly Tyr Lys Thr Phe Gln Asp Ala Ile Ser Pro<br>435                  440                  445                  450 | | | | 2661 |
| cag cat gct atc gag gtt ctt gat gag ttg act aat gga gat gct att<br>Gln His Ala Ile Glu Val Leu Asp Glu Leu Thr Asn Gly Asp Ala Ile<br>              455                  460                  465 | | | | 2709 |
| gtt agt act ggg gtt ggg cag cat caa atg tgg gct gcg cag ttt tac<br>Val Ser Thr Gly Val Gly Gln His Gln Met Trp Ala Ala Gln Phe Tyr<br>470                    475                  480 | | | | 2757 |
| aag tac aag aga ccg agg cag tgg ttg acc tca ggg ggt ctt gga gcc<br>Lys Tyr Lys Arg Pro Arg Gln Trp Leu Thr Ser Gly Gly Leu Gly Ala<br>485                  490                  495 | | | | 2805 |
| atg ggt ttt gga ttg cct gcg gct att ggt gct gct gtt gct aac cct<br>Met Gly Phe Gly Leu Pro Ala Ala Ile Gly Ala Ala Val Ala Asn Pro<br>500                    505                  510 | | | | 2853 |
| ggg gct gtt gtg gtt gac att gat ggg gat ggt agt ttc atc atg aat<br>Gly Ala Val Val Val Asp Ile Asp Gly Asp Gly Ser Phe Ile Met Asn<br>515                  520                  525                  530 | | | | 2901 |
| gtt cag gag ttg gcc act ata aga gtg gag aat ctc cca gtt aag ata<br>Val Gln Glu Leu Ala Thr Ile Arg Val Glu Asn Leu Pro Val Lys Ile<br>              535                  540                  545 | | | | 2949 |
| ttg ttg ttg aac aat cag cat ttg ggt atg gtg gtt cag ttg gag gat<br>Leu Leu Leu Asn Asn Gln His Leu Gly Met Val Val Gln Leu Glu Asp<br>550                    555                  560 | | | | 2997 |
| agg ttc tac aag tcc aat aga gct cac acc tat ctt gga gat ccg tct<br>Arg Phe Tyr Lys Ser Asn Arg Ala His Thr Tyr Leu Gly Asp Pro Ser<br>565                  570                  575 | | | | 3045 |
| agc gag agc gag ata ttc cca aac atg ctc aag ttt gct gat gct tgt<br>Ser Glu Ser Glu Ile Phe Pro Asn Met Leu Lys Phe Ala Asp Ala Cys<br>              580                  585                  590 | | | | 3093 |
| ggg ata ccg gca gcg cga gtg acg aag aag gaa gag ctt aga gcg gca<br>Gly Ile Pro Ala Ala Arg Val Thr Lys Lys Glu Glu Leu Arg Ala Ala<br>595                    600                  605                  610 | | | | 3141 |
| att cag aga atg ttg gac acc cct ggc ccc tac ctt ctt gat gtc att<br>Ile Gln Arg Met Leu Asp Thr Pro Gly Pro Tyr Leu Leu Asp Val Ile<br>              615                  620                  625 | | | | 3189 |
| gtg ccc cat cag gag cat gtg ttg ccg atg att ccc agt aat gga tcc<br>Val Pro His Gln Glu His Val Leu Pro Met Ile Pro Ser Asn Gly Ser<br>630                    635                  640 | | | | 3237 |
| ttc aag gat gtg ata act gag ggt gat ggt aga acg agg tac<br>Phe Lys Asp Val Ile Thr Glu Gly Asp Gly Arg Thr Arg Tyr<br>645                    650                  655 | | | | 3279 |
| tgattgccta gaccaaatgt tccttgatgc ttgttttgta caatatatat aagataatgc | | | | 3339 |

-continued

```
tgtcctagtt gcaggatttg gcctgtggtg agcatcatag tctgtagtag ttttggtagc    3399
aagacatttt attttccttt tatttaactt actacatgca gtagcatcta tctatctctg    3459
tagtctgata tctcctgttg tctgtattgt gccgttggat tttttgctgt agtgagactg    3519
aaaatgatgt gctagtaata atatttctgt tagaaatcta agtagagaat ctgttgaaga    3579
agtcaaaagc taatggaatc aggttacata tcaatgtttt tctttttta gcggttggta     3639 gacgtgtaga ttcaacttct cttggagctc acctaggcaa tcagtaaaat gcatattcct    3699
tttttaactt gccatttatt tacttttagt ggaaattgtg accaatttgt tcatgtagaa    3759
cggatttgga ccattgcgtc cacaaaacgt ctcttttgct cgatcttcac aaagcgatac    3819
cgaaatccag atagttttt caaaagtcag aaatggcaaa gttataaata gtaaaacaga    3879
atagatgctg taatcgactt caataacaag tggcatcacg tttctagttc tagacccggg    3939
```

<210> SEQ ID NO 23
<211> LENGTH: 656
<212> TYPE: PRT
<213> ORGANISM: Glycine max
<220> FEATURE:
<223> OTHER INFORMATION: herbicide-resistant soybean ALS

<400> SEQUENCE: 23

```
Met Pro His Asn Thr Met Ala Ala Thr Ala Ser Arg Thr Thr Arg Phe
1               5                   10                  15

Ser Ser Ser Ser Ser His Pro Thr Phe Pro Lys Arg Ile Thr Arg Ser
                20                  25                  30

Thr Leu Pro Leu Ser His Gln Thr Leu Thr Lys Pro Asn His Ala Leu
            35                  40                  45

Lys Ile Lys Cys Ser Ile Ser Lys Pro Pro Thr Ala Ala Pro Phe Thr
        50                  55                  60

Lys Glu Ala Pro Thr Thr Glu Pro Phe Val Ser Arg Phe Ala Ser Gly
65                  70                  75                  80

Glu Pro Arg Lys Gly Ala Asp Ile Leu Val Glu Ala Leu Glu Arg Gln
                85                  90                  95

Gly Val Thr Thr Val Phe Ala Tyr Pro Gly Gly Ala Ser Met Glu Ile
            100                 105                 110

His Gln Ala Leu Thr Arg Ser Ala Ala Ile Arg Asn Val Leu Pro Arg
        115                 120                 125

His Glu Gln Gly Gly Val Phe Ala Ala Glu Gly Tyr Ala Arg Ser Ser
    130                 135                 140

Gly Leu Pro Gly Val Cys Ile Ala Thr Ser Gly Pro Gly Ala Thr Asn
145                 150                 155                 160

Leu Val Ser Gly Leu Ala Asp Ala Leu Met Asp Ser Val Pro Val Val
                165                 170                 175

Ala Ile Thr Gly Gln Val Ala Arg Arg Met Ile Gly Thr Asp Ala Phe
            180                 185                 190

Gln Glu Thr Pro Ile Val Glu Val Ser Arg Ser Ile Thr Lys His Asn
        195                 200                 205

Tyr Leu Ile Leu Asp Val Asp Asp Ile Pro Arg Val Val Ala Glu Ala
    210                 215                 220

Phe Phe Val Ala Thr Ser Gly Arg Pro Gly Pro Val Leu Ile Asp Ile
225                 230                 235                 240

Pro Lys Asp Val Gln Gln Gln Leu Ala Val Pro Asn Trp Asp Glu Pro
                245                 250                 255
```

-continued

Val Asn Leu Pro Gly Tyr Leu Ala Arg Leu Pro Arg Pro Pro Ala Glu
            260                 265                 270

Ala Gln Leu Glu His Ile Val Arg Leu Ile Met Glu Ala Gln Lys Pro
        275                 280                 285

Val Leu Tyr Val Gly Gly Ser Leu Asn Ser Ala Glu Leu Arg
290                 295                 300

Arg Phe Val Glu Leu Thr Gly Ile Pro Val Ala Ser Thr Leu Met Gly
305                 310                 315                 320

Leu Gly Thr Phe Pro Ile Gly Asp Glu Tyr Ser Leu Gln Met Leu Gly
                325                 330                 335

Met His Gly Thr Val Tyr Ala Asn Tyr Ala Val Asp Asn Ser Asp Leu
                340                 345                 350

Leu Leu Ala Phe Gly Val Arg Phe Asp Asp Arg Val Thr Gly Lys Leu
            355                 360                 365

Glu Ala Phe Ala Ser Arg Ala Lys Ile Val His Ile Asp Ile Asp Ser
        370                 375                 380

Ala Glu Ile Gly Lys Asn Lys Gln Ala His Val Ser Val Cys Ala Asp
385                 390                 395                 400

Leu Lys Leu Ala Leu Lys Gly Ile Asn Met Ile Leu Glu Glu Lys Gly
                405                 410                 415

Val Glu Gly Lys Phe Asp Leu Gly Gly Trp Arg Glu Glu Ile Asn Val
            420                 425                 430

Gln Lys His Lys Phe Pro Leu Gly Tyr Lys Thr Phe Gln Asp Ala Ile
        435                 440                 445

Ser Pro Gln His Ala Ile Glu Val Leu Asp Glu Leu Thr Asn Gly Asp
    450                 455                 460

Ala Ile Val Ser Thr Gly Val Gly Gln His Gln Met Trp Ala Ala Gln
465                 470                 475                 480

Phe Tyr Lys Tyr Lys Arg Pro Arg Gln Trp Leu Thr Ser Gly Gly Leu
                485                 490                 495

Gly Ala Met Gly Phe Gly Leu Pro Ala Ala Ile Gly Ala Ala Val Ala
            500                 505                 510

Asn Pro Gly Ala Val Val Asp Ile Asp Gly Asp Gly Ser Phe Ile
        515                 520                 525

Met Asn Val Gln Glu Leu Ala Thr Ile Arg Val Glu Asn Leu Pro Val
530                 535                 540

Lys Ile Leu Leu Leu Asn Asn Gln His Leu Gly Met Val Val Gln Leu
545                 550                 555                 560

Glu Asp Arg Phe Tyr Lys Ser Asn Arg Ala His Thr Tyr Leu Gly Asp
                565                 570                 575

Pro Ser Ser Glu Ser Glu Ile Phe Pro Asn Met Leu Lys Phe Ala Asp
            580                 585                 590

Ala Cys Gly Ile Pro Ala Ala Arg Val Thr Lys Lys Glu Glu Leu Arg
        595                 600                 605

Ala Ala Ile Gln Arg Met Leu Asp Thr Pro Gly Pro Tyr Leu Leu Asp
    610                 615                 620

Val Ile Val Pro His Gln Glu His Val Leu Pro Met Ile Pro Ser Asn
625                 630                 635                 640

Gly Ser Phe Lys Asp Val Ile Thr Glu Gly Asp Gly Arg Thr Arg Tyr
                645                 650                 655

<210> SEQ ID NO 24
<211> LENGTH: 5408
<212> TYPE: DNA

```
<213> ORGANISM: Artificial Sequence
<220> FEATURE:
<223> OTHER INFORMATION: Description of Artificial Sequence: chimeric
      gene
<220> FEATURE:
<221> NAME/KEY: unsure
<222> LOCATION: (459)
<223> OTHER INFORMATION: n = a, c, g or t
<220> FEATURE:
<221> NAME/KEY: CDS
<222> LOCATION: (2163)..(4172)
<223> OTHER INFORMATION: herbicide-resistant Arabidopsis ALS coding
      region
<220> FEATURE:
<221> NAME/KEY: unsure
<222> LOCATION: (461)
<223> OTHER INFORMATION: n = a, c, g or t
<220> FEATURE:
<221> NAME/KEY: unsure
<222> LOCATION: (660)
<223> OTHER INFORMATION: n = a, c, g or t
<220> FEATURE:
<221> NAME/KEY: unsure
<222> LOCATION: (729)
<223> OTHER INFORMATION: n = a, c, g or t

<400> SEQUENCE: 24
atcgatagag acatgttatt cacaaaccat aaaatgatgg ctaaaattgg tgtgattgga      60
acgatatctg tttattatga tttcagggcg caaaaatgcg agtacttaat aaaattttac     120
atttaaatta gaattttttt tatcaataaa tattaattta ttagttttat tagaaatatt     180
aattagaaaa ttttgaatcc ccgatttctc ctccttttct tcgctattca tcattttcta     240
accaaaccaa tcttatatgt tcttcaaatt agaacttgaa attattaatt ataattaaac     300
tgaaaacaat ttggtatcaa ttcatataca tgcttagtaa taaatgcga taattaattg      360 ataaatctgc aaaagatttt acaaatatct ttcagaaaaa attaataaca aattttgtcg     420
ttttcatggt gttggtctga ggaggatttg gcactatana nctctcctac ggaccattct     480
ttgcacttca actaaacgat ggtcagaatt ggtggggatt ttatattcaa gcatatccct     540
ttcaaaactt cctacttact tcgtgcgttc ggtaatcggt aacattagac tttcaaaatc     600
atttttaacc cctaaacagt aaatttgaag gacaaaaata atattttttca aatttgatan     660 actatttttt ttttgtaatt tgacgaacca aaaccagatt tatcctgaat tttaggaacc     720
acagatgtna ctaaaccaat atttatttat tttctaaaac aaaatttcat ggcagcatgc     780
ctcagcccat gaaaaaaacc ttataaaaat atctacacat tgaccattga aaagttcgtt     840
ctcccatggg taaccagatc aaactcacat ccaaacataa catggatatc tccttaccaa     900
tcatactaat tatttttgggt taaatattaa tcattatttt taagtatatta attaagaaat     960 taaaagattt tttaaaaaaa tgtataaaat tatattattc atgattttttc atacatttga    1020 ttttgataat aaatatattt tttttaattt cttaaaaaat gttgcaagac acttattaga    1080
catagtcttg ttctgtttac aaaagcattc atcatttaat acattaaaaa atatttaata    1140
ctaacagtag aatcttcttg tgagtggtgt gggagtaggc aacctggcat tgaaacgaga    1200
gaaagagagt cagaaccaga agacaaataa aagtatgca acaaacaaat caaaatcaaa    1260
gggcaaaggc tggggttggc tcaattggtt gctacattca attttcaact cagtcaacgg    1320
ttgagattca ctctgacttc cccaatctaa gccgcggatg caaacggttg aatctaaccc    1380
acaatccaat ctcgttactt agggcttttt ccgtcattaa ctcaccccctg ccacccggtt    1440 tccctataaa ttgaactca atgctcccct ctaaactcgt atcgcttcag agttgagacc    1500
aagacacact cgttcatata tctctctgct cttctcttct cttctacctc tcaaggtact    1560
```

```
tttcttctcc ctctaccaaa tcctagattc cgtggttcaa tttcggatct tgcacttctg    1620
gtttgctttg ccttgctttt tcctcaactg ggtccatcta ggatccatgt gaaactctac    1680
tctttcttta atatctgcgg aatacgcgtt ggactttcag atctagtcga aatcatttca    1740
taattgcctt tctttctttt agcttatgag aaataaaatc actttttttt tatttcaaaa    1800
taaaccttgg gccttgtgct gactgagatg gggtttggtg attacagaat tttagcgaat    1860
tttgtaattg tacttgtttg tctgtagttt tgttttgttt tcttgtttct catacattcc    1920
ttaggcttca attttattcg agtataggtc acaataggaa ttcaaacttt gagcagggga    1980
attaatccct tccttcaaat ccagtttgtt tgtatatatg tttaaaaaat gaaacttttg    2040
ctttaaattc tattataact ttttttatgg ctgaaatttt tgcatgtgtc tttgctctct    2100
gttgtaaatt tactgtttag gtactaactc taggcttgtt gtgcagtttt tgaagtataa    2160
```

```
cc atg gcg gcg gca aca aca aca aca aca aca tct tct tcg atc tcc       2207
   Met Ala Ala Ala Thr Thr Thr Thr Thr Thr Ser Ser Ser Ile Ser
   1               5                   10                  15 ttc tcc acc aaa cca tct cct tcc tcc tcc aaa tca cca tta cca atc       2255
Phe Ser Thr Lys Pro Ser Pro Ser Ser Ser Lys Ser Pro Leu Pro Ile
                20                  25                  30 tcc aga ttc tcc ctc cca ttc tcc cta aac ccc aac aaa tca tcc tcc       2303
Ser Arg Phe Ser Leu Pro Phe Ser Leu Asn Pro Asn Lys Ser Ser Ser
            35                  40                  45 tcc tcc cgc cgc cgc ggt atc aaa tcc agc tct ccc tcc tcc atc tcc       2351
Ser Ser Arg Arg Arg Gly Ile Lys Ser Ser Ser Pro Ser Ser Ile Ser
        50                  55                  60 gcc gtg ctc aac aca acc acc aat gtc aca acc act ccc tct cca acc       2399
Ala Val Leu Asn Thr Thr Thr Asn Val Thr Thr Thr Pro Ser Pro Thr
    65                  70                  75 aaa cct acc aaa ccc gaa aca ttc atc tcc cga ttc gct cca gat caa       2447
Lys Pro Thr Lys Pro Glu Thr Phe Ile Ser Arg Phe Ala Pro Asp Gln
80                  85                  90                  95 ccc cgc aaa ggc gct gat atc ctc gtc gaa gct tta gaa cgt caa ggc       2495
Pro Arg Lys Gly Ala Asp Ile Leu Val Glu Ala Leu Glu Arg Gln Gly
                100                 105                 110 gta gaa acc gta ttc gct tac cct gga ggt gca tca atg gag att cac       2543
Val Glu Thr Val Phe Ala Tyr Pro Gly Gly Ala Ser Met Glu Ile His
            115                 120                 125 caa gcc tta acc cgc tct tcc tca atc cgt aac gtc ctt cct cgt cac       2591
Gln Ala Leu Thr Arg Ser Ser Ser Ile Arg Asn Val Leu Pro Arg His
        130                 135                 140 gaa caa gga ggt gta ttc gca gca gaa gga tac gct cga tcc tca ggt       2639
Glu Gln Gly Gly Val Phe Ala Ala Glu Gly Tyr Ala Arg Ser Ser Gly
    145                 150                 155 aaa cca ggt atc tgt ata gcc act tca ggt ccc gga gct aca aat ctc       2687
Lys Pro Gly Ile Cys Ile Ala Thr Ser Gly Pro Gly Ala Thr Asn Leu
160                 165                 170                 175 gtt agc gga tta gcc gat gcg ttg tta gat agt gtt cct ctt gta gca       2735
Val Ser Gly Leu Ala Asp Ala Leu Leu Asp Ser Val Pro Leu Val Ala
                180                 185                 190 atc aca gga caa gtc gct cgt cgt atg att ggt aca gat gcg ttt caa       2783
Ile Thr Gly Gln Val Ala Arg Arg Met Ile Gly Thr Asp Ala Phe Gln
            195                 200                 205 gag act ccg att gtt gag gta acg cgt tcg att acg aag cat aac tat       2831
Glu Thr Pro Ile Val Glu Val Thr Arg Ser Ile Thr Lys His Asn Tyr
        210                 215                 220 ctt gtg atg gat gtt gaa gat atc cct agg att att gag gaa gct ttc       2879
Leu Val Met Asp Val Glu Asp Ile Pro Arg Ile Ile Glu Glu Ala Phe
```

```
            225                 230                 235
ttt tta gct act tct ggt aga cct gga cct gtt ttg gtt gat gtt cct      2927
Phe Leu Ala Thr Ser Gly Arg Pro Gly Pro Val Leu Val Asp Val Pro
240                 245                 250                 255 aaa gat att caa caa cag ctt gcg att cct aat tgg gaa cag gct atg      2975
Lys Asp Ile Gln Gln Gln Leu Ala Ile Pro Asn Trp Glu Gln Ala Met
                260                 265                 270 aga tta cct ggt tat atg tct agg atg cct aaa cct ccg gaa gat tct      3023
Arg Leu Pro Gly Tyr Met Ser Arg Met Pro Lys Pro Pro Glu Asp Ser
            275                 280                 285 cat ttg gag cag att gtt agg ttg att tct gag tct aag aag cct gtg      3071
His Leu Glu Gln Ile Val Arg Leu Ile Ser Glu Ser Lys Lys Pro Val
        290                 295                 300 ttg tat gtt ggt ggt ggt tgt ttg aat tct agc gat gaa ttg ggt agg      3119
Leu Tyr Val Gly Gly Gly Cys Leu Asn Ser Ser Asp Glu Leu Gly Arg
    305                 310                 315 ttt gtt gag ctt acg ggg atc cct gtt gcg agt acg ttg atg ggg ctg      3167
Phe Val Glu Leu Thr Gly Ile Pro Val Ala Ser Thr Leu Met Gly Leu
320                 325                 330                 335 gga tct tat cct tgt gat gat gag ttg tcg tta cat atg ctt gga atg      3215
Gly Ser Tyr Pro Cys Asp Asp Glu Leu Ser Leu His Met Leu Gly Met
                340                 345                 350 cat ggg act gtg tat gca aat tac gct gtg gag cat agt gat ttg ttg      3263
His Gly Thr Val Tyr Ala Asn Tyr Ala Val Glu His Ser Asp Leu Leu
            355                 360                 365 ttg gcg ttt ggg gta agg ttt gat gat cgt gtc acg ggt aag ctt gag      3311
Leu Ala Phe Gly Val Arg Phe Asp Asp Arg Val Thr Gly Lys Leu Glu
        370                 375                 380 gct ttt gct agt agg gct aag att gtt cat att gat att gac tcg gct      3359
Ala Phe Ala Ser Arg Ala Lys Ile Val His Ile Asp Ile Asp Ser Ala
    385                 390                 395 gag att ggg aag aat aag act cct cat gtg tct gtg tgt ggt gat gtt      3407
Glu Ile Gly Lys Asn Lys Thr Pro His Val Ser Val Cys Gly Asp Val
400                 405                 410                 415 aag ctg gct ttg caa ggg atg aat aag gtt ctt gag aac cga gcg gag      3455
Lys Leu Ala Leu Gln Gly Met Asn Lys Val Leu Glu Asn Arg Ala Glu
                420                 425                 430 gag ctt aag ctt gat ttt gga gtt tgg agg aat gag ttg aac gta cag      3503
Glu Leu Lys Leu Asp Phe Gly Val Trp Arg Asn Glu Leu Asn Val Gln
            435                 440                 445 aaa cag aag ttt ccg ttg agc ttt aag acg ttt ggg gaa gct att cct      3551
Lys Gln Lys Phe Pro Leu Ser Phe Lys Thr Phe Gly Glu Ala Ile Pro
        450                 455                 460 cca cag tat gcg att aag gtc ctt gat gag ttg act gat gga aaa gcc      3599
Pro Gln Tyr Ala Ile Lys Val Leu Asp Glu Leu Thr Asp Gly Lys Ala
    465                 470                 475 ata ata agt act ggt gtc ggg caa cat caa atg tgg gcg gcg cag ttc      3647
Ile Ile Ser Thr Gly Val Gly Gln His Gln Met Trp Ala Ala Gln Phe
480                 485                 490                 495 tac aat tac aag aaa cca agg cag tgg cta tca tca gga ggc ctt gga      3695
Tyr Asn Tyr Lys Lys Pro Arg Gln Trp Leu Ser Ser Gly Gly Leu Gly
                500                 505                 510 gct atg gga ttt gga ctt cct gct gcg att gga gcg tct gtt gct aac      3743
Ala Met Gly Phe Gly Leu Pro Ala Ala Ile Gly Ala Ser Val Ala Asn
            515                 520                 525 cct gat gcg ata gtt gtg gat att gac gga gat gga agc ttt ata atg      3791
Pro Asp Ala Ile Val Val Asp Ile Asp Gly Asp Gly Ser Phe Ile Met
        530                 535                 540 aat gtg caa gag cta gcc act att cgt gta gag aat ctt cca gtg aag      3839
```

```
           Asn Val Gln Glu Leu Ala Thr Ile Arg Val Glu Asn Leu Pro Val Lys
              545                 550                 555 gta ctt tta tta aac aac cag cat ctt ggc atg gtt atg caa ttg gaa            3887
Val Leu Leu Leu Asn Asn Gln His Leu Gly Met Val Met Gln Leu Glu
560                 565                 570                 575 gat cgg ttc tac aaa gct aac cga gct cac aca ttt ctc ggg gat ccg            3935
Asp Arg Phe Tyr Lys Ala Asn Arg Ala His Thr Phe Leu Gly Asp Pro
                580                 585                 590 gct cag gag gac gag ata ttc ccg aac atg ttg ctg ttt gca gca gct            3983
Ala Gln Glu Asp Glu Ile Phe Pro Asn Met Leu Leu Phe Ala Ala Ala
            595                 600                 605 tgc ggg att cca gcg gcg agg gtg aca aag aaa gca gat ctc cga gaa            4031
Cys Gly Ile Pro Ala Ala Arg Val Thr Lys Lys Ala Asp Leu Arg Glu
        610                 615                 620 gct att cag aca atg ctg gat aca cca gga cct tac ctg ttg gat gtg            4079
Ala Ile Gln Thr Met Leu Asp Thr Pro Gly Pro Tyr Leu Leu Asp Val
625                 630                 635 att tgt ccg cac caa gaa cat gtg ttg ccg atg atc ccg agt ggt ggc            4127
Ile Cys Pro His Gln Glu His Val Leu Pro Met Ile Pro Ser Gly Gly
640                 645                 650                 655 act ttc aac gat gtc ata acg gaa gga gat ggc cgg att aaa tac                4172
Thr Phe Asn Asp Val Ile Thr Glu Gly Asp Gly Arg Ile Lys Tyr
                660                 665                 670 tgagagatga aaccggtgat tatcagaacc ttttatggtc tttgtatgca tatggtaaaa          4232
aaacttagtt tgcaatttcc tgtttgtttt ggtaatttga gtttcttta gttgttgatc           4292 tgcctgcttt ttggtttacg tcagactact actgctgttg ttgtttggtt tccttctctt          4352
cattttataa ataaataatc cggttcggtt tactccttgt gactggctca gtttggttat          4412
tgcgaaatgc gaatggtaaa ttgagtaatt gaaattcgtt attagggttc taagctgttt          4472
taacagtcac tgggttaata tctctcgaat cttgcatgga aaatgctctt accattggtt          4532
tttaattgaa atgtgctcat atgggccgtg gtttccaaat taaataaaac tacgatgtca          4592
tcgagaagta aaatcaactg tgtccacatt atcagttttg tgtatacgat gaaatagggt          4652
aattcaaaat ctagcttgat atgccttttg gttcatttta accttctgta aacatttttt          4712
cagattttga acaagtaaat ccaaaaaaaa aaaaaaaaa atctcaactc aacactaaat           4772
tattttaatg tataaaagat gcttaaaaca tttggcttaa aagaaagaag ctaaaaacat          4832
agagaactct tgtaaattga agtatgaaaa tatactgaat tgggtattat atgaattttt          4892
ctgatttagg attcacatga tccaaaaagg aaatccagaa gcactaatca gacattggaa         4952
gtaggaatat ttcaaaaagt ttttttttt taagtaagtg acaaaagctt ttaaaaaata          5012
gaaaagaaac tagtattaaa gttgtaaatt taataaacaa agaaatttt ttatatttt           5072 tcatttcttt ttccagcatg aggttatgat ggcaggatgt ggatttcatt ttttttcctt          5132
tgatagcctt ttaattgatc tattataatt gacgaaaaaa tattagttaa ttatagatat          5192
attttaggta gtattagcaa tttacacttc caaaagacta tgtaagttgt aaatatgatg          5252
cgttgatctc ttcatcattc aatggttagt caaaaaaata aaagcttaac tagtaaacta          5312
aagtagtcaa aaattgtact ttagtttaaa atattacatg aataatccaa aacgacattt          5372
atgtgaaaca aaaacaatat ctagaggatc cccggg                                    5408

<210> SEQ ID NO 25
<211> LENGTH: 670
<212> TYPE: PRT
<213> ORGANISM: Arabidopsis thaliana
<220> FEATURE:
```

<223> OTHER INFORMATION: herbicide-resistant Arabidopsis ALS

<400> SEQUENCE: 25

```
Met Ala Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
            20                  25                  30

Arg Phe Ser Leu Pro Phe Ser Leu Asn Pro Asn Lys Ser Ser Ser
        35                  40                  45

Ser Arg Arg Arg Gly Ile Lys Ser Ser Pro Ser Ser Ile Ser Ala
    50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
        115                 120                 125

Ala Leu Thr Arg Ser Ser Ile Arg Asn Val Leu Pro Arg His Glu
    130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
            180                 185                 190

Thr Gly Gln Val Ala Arg Arg Met Ile Gly Thr Asp Ala Phe Gln Glu
        195                 200                 205

Thr Pro Ile Val Glu Val Thr Arg Ser Ile Thr Lys His Asn Tyr Leu
    210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
            260                 265                 270

Leu Pro Gly Tyr Met Ser Arg Met Pro Lys Pro Pro Glu Asp Ser His
        275                 280                 285

Leu Glu Gln Ile Val Arg Leu Ile Ser Glu Ser Lys Lys Pro Val Leu
    290                 295                 300

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
                325                 330                 335

Ser Tyr Pro Cys Asp Asp Glu Leu Ser Leu His Met Leu Gly Met His
            340                 345                 350

Gly Thr Val Tyr Ala Asn Tyr Ala Val Glu His Ser Asp Leu Leu Leu
        355                 360                 365

Ala Phe Gly Val Arg Phe Asp Asp Arg Val Thr Gly Lys Leu Glu Ala
    370                 375                 380

Phe Ala Ser Arg Ala Lys Ile Val His Ile Asp Ile Asp Ser Ala Glu
385                 390                 395                 400
```

```
Ile Gly Lys Asn Lys Thr Pro His Val Ser Val Cys Gly Asp Val Lys
            405                 410                 415

Leu Ala Leu Gln Gly Met Asn Lys Val Leu Glu Asn Arg Ala Glu Glu
        420                 425                 430

Leu Lys Leu Asp Phe Gly Val Trp Arg Asn Glu Leu Asn Val Gln Lys
            435                 440                 445

Gln Lys Phe Pro Leu Ser Phe Lys Thr Phe Gly Glu Ala Ile Pro Pro
450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
                485                 490                 495

Asn Tyr Lys Lys Pro Arg Gln Trp Leu Ser Gly Gly Leu Gly Ala
                500                 505                 510

Met Gly Phe Gly Leu Pro Ala Ala Ile Gly Ala Ser Val Ala Asn Pro
            515                 520                 525

Asp Ala Ile Val Val Asp Ile Asp Gly Asp Gly Ser Phe Ile Met Asn
530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Leu Glu Asp
                565                 570                 575

Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
            595                 600                 605

Gly Ile Pro Ala Ala Arg Val Thr Lys Lys Ala Asp Leu Arg Glu Ala
610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
                645                 650                 655

Phe Asn Asp Val Ile Thr Glu Gly Asp Gly Arg Ile Lys Tyr
            660                 665                 670

<210> SEQ ID NO 26
<211> LENGTH: 667
<212> TYPE: PRT
<213> ORGANISM: Nicotiana tabacum

<400> SEQUENCE: 26

Met Ala Ala Ala Pro Ser Pro Ser Ser Ala Phe Ser Lys Thr
1               5                   10                  15

Leu Ser Pro Ser Ser Thr Ser Thr Leu Leu Pro Arg Ser Thr
            20                  25                  30

Phe Pro Phe Pro His His Pro His Lys Thr Thr Pro Pro Leu His
        35                  40                  45

Leu Thr His Thr His Ile His Ile His Ser Gln Arg Arg Phe Thr
    50                  55                  60

Ile Ser Asn Val Ile Ser Thr Asn Gln Lys Val Ser Gln Thr Glu Lys
65                  70                  75                  80

Thr Glu Thr Phe Val Ser Arg Phe Ala Pro Asp Glu Pro Arg Lys Gly
                85                  90                  95

Ser Asp Val Leu Val Glu Ala Leu Glu Arg Glu Gly Val Thr Asp Val
                100                 105                 110
```

```
Phe Ala Tyr Pro Gly Gly Ala Ser Met Glu Ile His Gln Ala Leu Thr
        115                 120                 125
Arg Ser Ser Ile Ile Arg Asn Val Leu Pro Arg His Glu Gln Gly Gly
    130                 135                 140
Val Phe Ala Ala Glu Gly Tyr Ala Arg Ala Thr Gly Phe Pro Gly Val
145                 150                 155                 160
Cys Ile Ala Thr Ser Gly Pro Gly Ala Thr Asn Leu Val Ser Gly Leu
                165                 170                 175
Ala Asp Ala Leu Leu Asp Ser Val Pro Ile Val Ala Ile Thr Gly Gln
            180                 185                 190
Val Pro Arg Arg Met Ile Gly Thr Asp Ala Phe Gln Glu Thr Pro Ile
        195                 200                 205
Val Glu Val Thr Arg Ser Ile Thr Lys His Asn Tyr Leu Val Met Asp
    210                 215                 220
Val Glu Asp Ile Pro Arg Val Val Arg Glu Ala Phe Phe Leu Ala Arg
225                 230                 235                 240
Ser Gly Arg Pro Gly Pro Ile Leu Ile Asp Val Pro Lys Asp Ile Gln
                245                 250                 255
Gln Gln Leu Val Ile Pro Asp Trp Asp Gln Pro Met Arg Leu Pro Gly
            260                 265                 270
Tyr Met Ser Arg Leu Pro Lys Leu Pro Asn Glu Met Leu Leu Glu Gln
        275                 280                 285
Ile Val Arg Leu Ile Ser Glu Ser Lys Lys Pro Val Leu Tyr Val Gly
    290                 295                 300
Gly Gly Cys Ser Gln Ser Ser Glu Asp Leu Arg Arg Phe Val Glu Leu
305                 310                 315                 320
Thr Gly Ile Pro Val Ala Ser Thr Leu Met Gly Leu Gly Ala Phe Pro
                325                 330                 335
Thr Gly Asp Glu Leu Ser Leu Ser Met Leu Gly Met His Gly Thr Val
            340                 345                 350
Tyr Ala Asn Tyr Ala Val Asp Ser Ser Asp Leu Leu Leu Ala Phe Gly
        355                 360                 365
Val Arg Phe Asp Asp Arg Val Thr Gly Lys Leu Glu Ala Phe Ala Ser
    370                 375                 380
Arg Ala Lys Ile Val His Ile Asp Ile Asp Ser Ala Glu Ile Gly Lys
385                 390                 395                 400
Asn Lys Gln Pro His Val Ser Ile Cys Ala Asp Ile Lys Leu Ala Leu
                405                 410                 415
Gln Gly Leu Asn Ser Ile Leu Glu Ser Lys Glu Gly Lys Leu Lys Leu
            420                 425                 430
Asp Phe Ser Ala Trp Arg Gln Glu Leu Thr Glu Gln Lys Val Lys His
        435                 440                 445
Pro Leu Asn Phe Lys Thr Phe Gly Asp Ala Ile Pro Pro Gln Tyr Ala
        450                 455                 460
Ile Gln Val Leu Asp Glu Leu Thr Asn Gly Asn Ala Ile Ile Ser Thr
465                 470                 475                 480
Gly Val Gly Gln His Gln Met Trp Ala Ala Gln Tyr Tyr Lys Tyr Arg
                485                 490                 495
Lys Pro Arg Gln Trp Leu Thr Ser Gly Gly Leu Gly Ala Met Gly Phe
            500                 505                 510
Gly Leu Pro Ala Ala Ile Gly Ala Ala Val Gly Arg Pro Asp Glu Val
        515                 520                 525
```

```
Val Val Asp Ile Asp Gly Asp Gly Ser Phe Ile Met Asn Val Gln Glu
        530                 535                 540

Leu Ala Thr Ile Lys Val Glu Asn Leu Pro Val Lys Ile Met Leu Leu
545                 550                 555                 560

Asn Asn Gln His Leu Gly Met Val Val Gln Trp Glu Asp Arg Phe Tyr
                565                 570                 575

Lys Ala Asn Arg Ala His Thr Tyr Leu Gly Asn Pro Ser Asn Glu Ala
                580                 585                 590

Glu Ile Phe Pro Asn Met Leu Lys Phe Ala Glu Ala Cys Gly Val Pro
            595                 600                 605

Ala Ala Arg Val Thr His Arg Asp Asp Leu Arg Ala Ile Gln Lys
            610                 615                 620

Met Leu Asp Thr Pro Gly Pro Tyr Leu Leu Asp Val Ile Val Pro His
625                 630                 635                 640

Gln Glu His Val Leu Pro Met Ile Pro Ser Gly Gly Ala Phe Lys Asp
                645                 650                 655

Val Ile Thr Glu Gly Asp Gly Arg Ser Ser Tyr
                660                 665

<210> SEQ ID NO 27
<211> LENGTH: 664
<212> TYPE: PRT
<213> ORGANISM: Nicotiana tabacum

<400> SEQUENCE: 27

Met Ala Ala Ala Ala Ala Pro Ser Pro Ser Phe Ser Lys Thr Leu
1               5                   10                  15

Ser Ser Ser Ser Ser Lys Ser Ser Thr Leu Leu Pro Arg Ser Thr Phe
                20                  25                  30

Pro Phe Pro His His Pro His Lys Thr Thr Pro Pro Leu His Leu
            35                  40                  45

Thr Pro Thr His Ile His Ser Gln Arg Arg Phe Thr Ile Ser Asn
    50                  55                  60

Val Ile Ser Thr Thr Gln Lys Val Ser Glu Thr Gln Lys Ala Glu Thr
65                  70                  75                  80

Phe Val Ser Arg Phe Ala Pro Asp Glu Pro Arg Lys Gly Ser Asp Val
                85                  90                  95

Leu Val Glu Ala Leu Glu Arg Glu Gly Val Thr Asp Val Phe Ala Tyr
            100                 105                 110

Pro Gly Gly Ala Ser Met Glu Ile His Gln Ala Leu Thr Arg Ser Ser
            115                 120                 125

Ile Ile Arg Asn Val Leu Pro Arg His Glu Gln Gly Gly Val Phe Ala
130                 135                 140

Ala Glu Gly Tyr Ala Arg Ala Thr Gly Phe Pro Gly Val Cys Ile Ala
145                 150                 155                 160

Thr Ser Gly Pro Gly Ala Thr Asn Leu Val Ser Gly Leu Ala Asp Ala
                165                 170                 175

Leu Leu Asp Ser Val Pro Ile Val Ala Ile Thr Gly Gln Val Pro Arg
            180                 185                 190

Arg Met Ile Gly Thr Asp Ala Phe Gln Glu Thr Pro Ile Val Glu Val
        195                 200                 205

Thr Arg Ser Ile Thr Lys His Asn Tyr Leu Val Met Asp Val Glu Asp
    210                 215                 220

Ile Pro Arg Val Val Arg Glu Ala Phe Phe Leu Ala Arg Ser Gly Arg
225                 230                 235                 240
```

```
Pro Gly Pro Val Leu Ile Asp Val Pro Lys Asp Ile Gln Gln Leu
            245                 250                 255

Val Ile Pro Asp Trp Asp Gln Pro Met Arg Leu Pro Gly Tyr Met Ser
        260                 265                 270

Arg Leu Pro Lys Leu Pro Asn Glu Met Leu Leu Glu Gln Ile Val Arg
        275                 280                 285

Leu Ile Ser Glu Ser Lys Lys Pro Val Leu Tyr Val Gly Gly Gly Cys
        290                 295                 300

Ser Gln Ser Ser Glu Glu Leu Arg Arg Phe Val Glu Leu Thr Gly Ile
305                 310                 315                 320

Pro Val Ala Ser Thr Leu Met Gly Leu Gly Ala Phe Pro Thr Gly Asp
                325                 330                 335

Glu Leu Ser Leu Ser Met Leu Gly Met His Gly Thr Val Tyr Ala Asn
                340                 345                 350

Tyr Ala Val Asp Ser Ser Asp Leu Leu Leu Ala Phe Gly Val Arg Phe
            355                 360                 365

Asp Asp Arg Val Thr Gly Lys Leu Glu Ala Phe Ala Ser Arg Ala Lys
    370                 375                 380

Ile Val His Ile Asp Ile Asp Ser Ala Glu Ile Gly Lys Asn Lys Gln
385                 390                 395                 400

Pro His Val Ser Ile Cys Ala Asp Ile Lys Leu Ala Leu Gln Gly Leu
                405                 410                 415

Asn Ser Ile Leu Glu Ser Lys Glu Gly Lys Leu Lys Leu Asp Phe Ser
                420                 425                 430

Ala Trp Arg Gln Glu Leu Thr Val Gln Lys Val Lys Tyr Pro Leu Asn
            435                 440                 445

Phe Lys Thr Phe Gly Asp Ala Ile Pro Pro Gln Tyr Ala Ile Gln Val
        450                 455                 460

Leu Asp Glu Leu Thr Asn Gly Ser Ala Ile Ile Ser Thr Gly Val Gly
465                 470                 475                 480

Gln His Gln Met Trp Ala Ala Gln Tyr Tyr Lys Tyr Arg Lys Pro Arg
                485                 490                 495

Gln Trp Leu Thr Ser Gly Gly Leu Gly Ala Met Gly Phe Gly Leu Pro
            500                 505                 510

Ala Ala Ile Gly Ala Ala Val Gly Arg Pro Asp Glu Val Val Val Asp
            515                 520                 525

Ile Asp Gly Asp Gly Ser Phe Ile Met Asn Val Gln Glu Leu Ala Thr
530                 535                 540

Ile Lys Val Glu Asn Leu Pro Val Lys Ile Met Leu Leu Asn Asn Gln
545                 550                 555                 560

His Leu Gly Met Val Val Gln Trp Glu Asp Arg Phe Tyr Lys Ala Asn
                565                 570                 575

Arg Ala His Thr Tyr Leu Gly Asn Pro Ser Asn Glu Ala Glu Ile Phe
            580                 585                 590

Pro Asn Met Leu Lys Phe Ala Glu Ala Cys Gly Val Pro Ala Ala Arg
        595                 600                 605

Val Thr His Arg Asp Asp Leu Arg Ala Ala Ile Gln Lys Met Leu Asp
        610                 615                 620

Thr Pro Gly Pro Tyr Leu Leu Asp Val Ile Val Pro His Gln Glu His
625                 630                 635                 640

Val Leu Pro Met Ile Pro Ser Gly Gly Ala Phe Lys Asp Val Ile Thr
                645                 650                 655
```

Glu Gly Asp Gly Arg Ser Ser Tyr
            660

<210> SEQ ID NO 28
<211> LENGTH: 652
<212> TYPE: PRT
<213> ORGANISM: Brassica napus

<400> SEQUENCE: 28

Met Ala Ala Ala Thr Ser Ser Pro Ile Ser Leu Thr Ala Lys Pro
 1               5                  10                  15

Ser Ser Lys Ser Pro Leu Pro Ile Ser Arg Phe Ser Leu Pro Phe Ser
                20                  25                  30

Leu Thr Pro Gln Lys Pro Ser Ser Arg Leu His Arg Pro Leu Ala Ile
                35                  40                  45

Ser Ala Val Leu Asn Ser Pro Val Asn Val Ala Pro Glu Lys Thr Asp
            50                  55                  60

Lys Ile Lys Thr Phe Ile Ser Arg Tyr Ala Pro Asp Glu Pro Arg Lys
65                  70                  75                  80

Gly Ala Asp Ile Leu Val Glu Ala Leu Glu Arg Gln Gly Val Glu Thr
                85                  90                  95

Val Phe Ala Tyr Pro Gly Gly Ala Ser Met Glu Ile His Gln Ala Leu
                100                 105                 110

Thr Arg Ser Ser Thr Ile Arg Asn Val Leu Pro Arg His Glu Gln Gly
                115                 120                 125

Gly Val Phe Ala Ala Glu Gly Tyr Ala Arg Ser Ser Gly Lys Pro Gly
                130                 135                 140

Ile Cys Ile Ala Thr Ser Gly Pro Gly Ala Thr Asn Leu Val Ser Gly
145                 150                 155                 160

Leu Ala Asp Ala Met Leu Asp Ser Val Pro Leu Val Ala Ile Thr Gly
                165                 170                 175

Gln Val Pro Arg Arg Met Ile Gly Thr Asp Ala Phe Gln Glu Thr Pro
                180                 185                 190

Ile Val Glu Val Thr Arg Ser Ile Thr Lys His Asn Tyr Leu Val Met
                195                 200                 205

Asp Val Asp Asp Ile Pro Arg Ile Val Gln Glu Ala Phe Phe Leu Ala
            210                 215                 220

Thr Ser Gly Arg Pro Gly Pro Val Leu Val Asp Val Pro Lys Asp Ile
225                 230                 235                 240

Gln Gln Gln Leu Ala Ile Pro Asn Trp Asp Gln Pro Met Arg Leu Pro
                245                 250                 255

Gly Tyr Met Ser Arg Leu Pro Gln Pro Pro Glu Val Ser Gln Leu Gly
                260                 265                 270

Gln Ile Val Arg Leu Ile Ser Glu Ser Lys Arg Pro Val Leu Tyr Val
                275                 280                 285

Gly Gly Gly Ser Leu Asn Ser Ser Glu Glu Leu Gly Arg Phe Val Glu
            290                 295                 300

Leu Thr Gly Ile Pro Val Ala Ser Thr Leu Met Gly Leu Gly Ser Tyr
305                 310                 315                 320

Pro Cys Asn Asp Glu Leu Ser Leu Gln Met Leu Gly Met His Gly Thr
                325                 330                 335

Val Tyr Ala Asn Tyr Ala Val Glu His Ser Asp Leu Leu Leu Ala Phe
                340                 345                 350

Gly Val Arg Phe Asp Asp Arg Val Thr Gly Lys Leu Glu Ala Phe Ala
                355                 360                 365

```
Ser Arg Ala Lys Ile Val His Ile Asp Ile Asp Ser Ala Glu Ile Gly
    370                 375                 380

Lys Asn Lys Thr Pro His Val Ser Val Cys Gly Asp Val Lys Leu Ala
385                 390                 395                 400

Leu Gln Gly Met Asn Lys Val Leu Glu Asn Arg Ala Glu Glu Leu Lys
            405                 410                 415

Leu Asp Phe Gly Val Trp Arg Ser Glu Leu Ser Glu Gln Lys Gln Lys
        420                 425                 430

Phe Pro Leu Ser Phe Lys Thr Phe Gly Glu Ala Ile Pro Pro Gln Tyr
            435                 440                 445

Ala Ile Gln Val Leu Asp Glu Leu Thr Gln Gly Lys Ala Ile Ile Ser
    450                 455                 460

Thr Gly Val Gly Gln His Gln Met Trp Ala Ala Gln Phe Tyr Lys Tyr
465                 470                 475                 480

Arg Lys Pro Arg Gln Trp Leu Ser Ser Ser Gly Leu Gly Ala Met Gly
                485                 490                 495

Phe Gly Leu Pro Ala Ala Ile Gly Ala Ser Val Ala Asn Pro Asp Ala
            500                 505                 510

Ile Val Val Asp Ile Asp Gly Asp Gly Ser Phe Ile Met Asn Val Gln
        515                 520                 525

Glu Leu Ala Thr Ile Arg Val Glu Asn Leu Pro Val Lys Ile Leu Leu
    530                 535                 540

Leu Asn Asn Gln His Leu Gly Met Val Met Gln Trp Glu Asp Arg Phe
545                 550                 555                 560

Tyr Lys Ala Asn Arg Ala His Thr Tyr Leu Gly Asp Pro Ala Arg Glu
                565                 570                 575

Asn Glu Ile Phe Pro Asn Met Leu Gln Phe Ala Gly Ala Cys Gly Ile
            580                 585                 590

Pro Ala Ala Arg Val Thr Lys Lys Glu Glu Leu Arg Glu Ala Ile Gln
        595                 600                 605

Thr Met Leu Asp Thr Pro Gly Pro Tyr Leu Leu Asp Val Ile Cys Pro
    610                 615                 620

His Gln Glu His Val Leu Pro Met Ile Pro Ser Gly Gly Thr Phe Lys
625                 630                 635                 640

Asp Val Ile Thr Glu Gly Asp Gly Arg Thr Lys Tyr
                645                 650

<210> SEQ ID NO 29
<211> LENGTH: 670
<212> TYPE: PRT
<213> ORGANISM: Arabidopsis thaliana

<400> SEQUENCE: 29

Met Ala Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
                20                  25                  30

Arg Phe Ser Leu Pro Phe Ser Leu Asn Pro Asn Lys Ser Ser Ser
            35                  40                  45

Ser Arg Arg Arg Gly Ile Lys Ser Ser Ser Pro Ser Ser Ile Ser Ala
    50                  55                  60

Val Leu Asn Thr Thr Thr Asn Val Thr Thr Pro Ser Pro Thr Lys
65                  70                  75                  80

Pro Thr Lys Pro Glu Thr Phe Ile Ser Arg Phe Ala Pro Asp Gln Pro
```

```
                85                  90                  95
Arg Lys Gly Ala Asp Ile Leu Val Glu Ala Leu Glu Arg Gln Gly Val
            100                 105                 110
Glu Thr Val Phe Ala Tyr Pro Gly Gly Ala Ser Met Glu Ile His Gln
            115                 120                 125
Ala Leu Thr Arg Ser Ser Ile Arg Asn Val Leu Pro Arg His Glu
        130                 135                 140
Gln Gly Gly Val Phe Ala Ala Glu Gly Tyr Ala Arg Ser Ser Gly Lys
145                 150                 155                 160
Pro Gly Ile Cys Ile Ala Thr Ser Gly Pro Gly Ala Thr Asn Leu Val
                165                 170                 175
Ser Gly Leu Ala Asp Ala Leu Leu Asp Ser Val Pro Leu Val Ala Ile
            180                 185                 190
Thr Gly Gln Val Pro Arg Arg Met Ile Gly Thr Asp Ala Phe Gln Glu
        195                 200                 205
Thr Pro Ile Val Glu Val Thr Arg Ser Ile Thr Lys His Asn Tyr Leu
    210                 215                 220
Val Met Asp Val Glu Asp Ile Pro Arg Ile Ile Glu Glu Ala Phe Phe
225                 230                 235                 240
Leu Ala Thr Ser Gly Arg Pro Gly Pro Val Leu Val Asp Val Pro Lys
                245                 250                 255
Asp Ile Gln Gln Gln Leu Ala Ile Pro Asn Trp Glu Gln Ala Met Arg
            260                 265                 270
Leu Pro Gly Tyr Met Ser Arg Met Pro Lys Pro Pro Glu Asp Ser His
        275                 280                 285
Leu Glu Gln Ile Val Arg Leu Ile Ser Glu Ser Lys Lys Pro Val Leu
    290                 295                 300
Tyr Val Gly Gly Gly Cys Leu Asn Ser Ser Asp Glu Leu Gly Arg Phe
305                 310                 315                 320
Val Glu Leu Thr Gly Ile Pro Val Ala Ser Thr Leu Met Gly Leu Gly
                325                 330                 335
Ser Tyr Pro Cys Asp Asp Glu Leu Ser Leu His Met Leu Gly Met His
            340                 345                 350
Gly Thr Val Tyr Ala Asn Tyr Ala Val Glu His Ser Asp Leu Leu Leu
        355                 360                 365
Ala Phe Gly Val Arg Phe Asp Asp Arg Val Thr Gly Lys Leu Glu Ala
    370                 375                 380
Phe Ala Ser Arg Ala Lys Ile Val His Ile Asp Ile Asp Ser Ala Glu
385                 390                 395                 400
Ile Gly Lys Asn Lys Thr Pro His Val Ser Val Cys Gly Asp Val Lys
                405                 410                 415
Leu Ala Leu Gln Gly Met Asn Lys Val Leu Glu Asn Arg Ala Glu Glu
            420                 425                 430
Leu Lys Leu Asp Phe Gly Val Trp Arg Asn Glu Leu Asn Val Gln Lys
        435                 440                 445
Gln Lys Phe Pro Leu Ser Phe Lys Thr Phe Gly Glu Ala Ile Pro Pro
    450                 455                 460
Gln Tyr Ala Ile Lys Val Leu Asp Glu Leu Thr Asp Gly Lys Ala Ile
465                 470                 475                 480
Ile Ser Thr Gly Val Gly Gln His Gln Met Trp Ala Ala Gln Phe Tyr
                485                 490                 495
Asn Tyr Lys Lys Pro Arg Gln Trp Leu Ser Ser Gly Gly Leu Gly Ala
            500                 505                 510
```

Met Gly Phe Gly Leu Pro Ala Ala Ile Gly Ala Ser Val Ala Asn Pro
            515                 520                 525

Asp Ala Ile Val Val Asp Ile Asp Gly Asp Gly Ser Phe Ile Met Asn
        530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Trp Glu Asp
                565                 570                 575

Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
        595                 600                 605

Gly Ile Pro Ala Ala Arg Val Thr Lys Lys Ala Asp Leu Arg Glu Ala
    610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
                645                 650                 655

Phe Asn Asp Val Ile Thr Glu Gly Asp Gly Arg Ile Lys Tyr
            660                 665                 670

<210> SEQ ID NO 30
<211> LENGTH: 651
<212> TYPE: PRT
<213> ORGANISM: Glycine max

<400> SEQUENCE: 30

Met Ala Ala Thr Ala Ser Arg Thr Thr Arg Phe Ser Ser Ser Ser Ser
1               5                   10                  15

His Pro Thr Phe Pro Lys Arg Ile Thr Arg Ser Thr Leu Pro Leu Ser
            20                  25                  30

His Gln Thr Leu Thr Lys Pro Asn His Ala Leu Lys Ile Lys Cys Ser
        35                  40                  45

Ile Ser Lys Pro Pro Thr Ala Ala Pro Phe Thr Lys Glu Ala Pro Thr
    50                  55                  60

Thr Glu Pro Phe Val Ser Arg Phe Ala Ser Gly Glu Pro Arg Lys Gly
65                  70                  75                  80

Ala Asp Ile Leu Val Glu Ala Leu Glu Arg Gln Gly Val Thr Thr Val
                85                  90                  95

Phe Ala Tyr Pro Gly Gly Ala Ser Met Glu Ile His Gln Ala Leu Thr
            100                 105                 110

Arg Ser Ala Ala Ile Arg Asn Val Leu Pro Arg His Glu Gln Gly Gly
        115                 120                 125

Val Phe Ala Ala Glu Gly Tyr Ala Arg Ser Ser Gly Leu Pro Gly Val
    130                 135                 140

Cys Ile Ala Thr Ser Gly Pro Gly Ala Thr Asn Leu Val Ser Gly Leu
145                 150                 155                 160

Ala Asp Ala Leu Met Asp Ser Val Pro Val Val Ala Ile Thr Gly Gln
                165                 170                 175

Val Pro Arg Arg Met Ile Gly Thr Asp Ala Phe Gln Glu Thr Pro Ile
            180                 185                 190

Val Glu Val Ser Arg Ser Ile Thr Lys His Asn Tyr Leu Ile Leu Asp
        195                 200                 205

Val Asp Asp Ile Pro Arg Val Val Ala Glu Ala Phe Phe Val Ala Thr

-continued

```
            210                 215                 220
Ser Gly Arg Pro Gly Pro Val Leu Ile Asp Ile Pro Lys Asp Val Gln
225                 230                 235                 240

Gln Gln Leu Ala Val Pro Asn Trp Asp Glu Pro Val Asn Leu Pro Gly
                245                 250                 255

Tyr Leu Ala Arg Leu Pro Arg Pro Ala Glu Ala Gln Leu Glu His
                260                 265                 270

Ile Val Arg Leu Ile Met Glu Ala Gln Lys Pro Val Leu Tyr Val Gly
                275                 280                 285

Gly Gly Ser Leu Asn Ser Ser Ala Glu Leu Arg Arg Phe Val Glu Leu
                290                 295                 300

Thr Gly Ile Pro Val Ala Ser Thr Leu Met Gly Leu Gly Thr Phe Pro
305                 310                 315                 320

Ile Gly Asp Glu Tyr Ser Leu Gln Met Leu Gly Met His Gly Thr Val
                325                 330                 335

Tyr Ala Asn Tyr Ala Val Asp Asn Ser Asp Leu Leu Leu Ala Phe Gly
                340                 345                 350

Val Arg Phe Asp Asp Arg Val Thr Gly Lys Leu Glu Ala Phe Ala Ser
                355                 360                 365

Arg Ala Lys Ile Val His Ile Asp Ile Asp Ser Ala Glu Ile Gly Lys
                370                 375                 380

Asn Lys Gln Ala His Val Ser Val Cys Ala Asp Leu Lys Leu Ala Leu
385                 390                 395                 400

Lys Gly Ile Asn Met Ile Leu Glu Glu Lys Gly Val Glu Gly Lys Phe
                405                 410                 415

Asp Leu Gly Gly Trp Arg Glu Glu Ile Asn Val Gln Lys His Lys Phe
                420                 425                 430

Pro Leu Gly Tyr Lys Thr Phe Gln Asp Ala Ile Ser Pro Gln His Ala
                435                 440                 445

Ile Glu Val Leu Asp Glu Leu Thr Asn Gly Asp Ala Ile Val Ser Thr
                450                 455                 460

Gly Val Gly Gln His Gln Met Trp Ala Ala Gln Phe Tyr Lys Tyr Lys
465                 470                 475                 480

Arg Pro Arg Gln Trp Leu Thr Ser Gly Gly Leu Gly Ala Met Gly Phe
                485                 490                 495

Gly Leu Pro Ala Ala Ile Gly Ala Ala Val Ala Asn Pro Gly Ala Val
                500                 505                 510

Val Val Asp Ile Asp Gly Asp Gly Ser Phe Ile Met Asn Val Gln Glu
                515                 520                 525

Leu Ala Thr Ile Arg Val Glu Asn Leu Pro Val Lys Ile Leu Leu Leu
530                 535                 540

Asn Asn Gln His Leu Gly Met Val Val Gln Trp Glu Asp Arg Phe Tyr
545                 550                 555                 560

Lys Ser Asn Arg Ala His Thr Tyr Leu Gly Asp Pro Ser Ser Glu Ser
                565                 570                 575

Glu Ile Phe Pro Asn Met Leu Lys Phe Ala Asp Ala Cys Gly Ile Pro
                580                 585                 590

Ala Ala Arg Val Thr Lys Lys Glu Glu Leu Arg Ala Ala Ile Gln Arg
                595                 600                 605

Met Leu Asp Thr Pro Gly Pro Tyr Leu Leu Asp Val Ile Val Pro His
                610                 615                 620

Gln Glu His Val Leu Pro Met Ile Pro Ser Asn Gly Ser Phe Lys Asp
625                 630                 635                 640
```

```
Val Ile Thr Glu Gly Asp Gly Arg Thr Arg Tyr
                645                 650

<210> SEQ ID NO 31
<211> LENGTH: 4
<212> TYPE: PRT
<213> ORGANISM: Artificial
<220> FEATURE:
<223> OTHER INFORMATION: ALS conserved subsequence B

<400> SEQUENCE: 31

Gly Gln Val Pro
1

<210> SEQ ID NO 32
<211> LENGTH: 10
<212> TYPE: PRT
<213> ORGANISM: Artificial
<220> FEATURE:
<223> OTHER INFORMATION: ALS conserved subsequence F
<220> FEATURE:
<221> NAME/KEY: UNSURE
<222> LOCATION: (4)..(4)
<220> FEATURE:
<221> NAME/KEY: UNSURE
<222> LOCATION: (4)..(4)
<223> OTHER INFORMATION: Xaa is Val or Met

<400> SEQUENCE: 32

Gly Met Val Xaa Gln Trp Glu Asp Arg Phe
1               5                   10

<210> SEQ ID NO 33
<211> LENGTH: 5
<212> TYPE: PRT
<213> ORGANISM: Artificial
<220> FEATURE:
<223> OTHER INFORMATION: Artificial amino-terminal extension

<400> SEQUENCE: 33

Met Pro His Asn Thr
1               5
```